(12) United States Patent
Parham et al.

(10) Patent No.: US 9,985,220 B2
(45) Date of Patent: May 29, 2018

(54) MATERIALS FOR ELECTRONIC DEVICES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Christof Pflumm, Darmstadt (DE); Jonas Valentin Kroeber, Frankfurt am Main (DE); Rémi Manouk Anèmian, Seoul (KR)

(73) Assignee: Merck Patent GmbH (DE)

( * ) Notice: Subject to any disclaimer, the term of this patent is extended or adjusted under 35 U.S.C. 154(b) by 394 days.

(21) Appl. No.: 14/651,453

(22) PCT Filed: Nov. 15, 2013

(86) PCT No.: PCT/EP2013/003456
§ 371 (c)(1),
(2) Date: Jun. 11, 2015

(87) PCT Pub. No.: WO2014/090368
PCT Pub. Date: Jun. 19, 2014

(65) Prior Publication Data
US 2015/0333274 A1 Nov. 19, 2015

(30) Foreign Application Priority Data
Dec. 14, 2012 (EP) .................................... 12008332

(51) Int. Cl.
| | | |
|---|---|---|
| *H01L 51/00* | (2006.01) | |
| *C09K 11/02* | (2006.01) | |
| *C08G 73/06* | (2006.01) | |
| *C07D 405/14* | (2006.01) | |
| *C07D 403/04* | (2006.01) | |
| *C07D 403/14* | (2006.01) | |
| *C09K 11/06* | (2006.01) | |
| *H01L 51/50* | (2006.01) | |

(52) U.S. Cl.
CPC ........ *H01L 51/0072* (2013.01); *C07D 403/04* (2013.01); *C07D 403/14* (2013.01); *C07D 405/14* (2013.01); *C08G 73/0672* (2013.01); *C09K 11/025* (2013.01); *C09K 11/06* (2013.01); *H01L 51/0035* (2013.01); *H01L 51/0067* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0073* (2013.01); *H01L 51/0085* (2013.01); *H01L 51/5012* (2013.01); *H01L 51/5072* (2013.01); *H01L 51/5092* (2013.01); *H01L 51/5096* (2013.01); *Y02E 10/549* (2013.01)

(58) Field of Classification Search
CPC ............ H01L 51/0072; H01L 51/0035; H01L 51/0067; H01L 51/5012; H01L 51/5072; H01L 51/5092; H01L 51/5096; C09K 11/025; C09K 2211/1011; C09K 2211/1044; C09K 2211/1029; C09K 2211/1059; C07D 403/04; C07D 403/14; C08G 73/0677; C08G 73/0672
USPC ................... 428/690, 917; 252/301.16, 500; 544/180, 212; 585/26
See application file for complete search history.

(56) References Cited

U.S. PATENT DOCUMENTS

| | | | |
|---|---|---|---|
| 2012/0013247 A1 | 1/2012 | Yi et al. | |
| 2012/0068170 A1 | 3/2012 | Pflumm et al. | |
| 2013/0126856 A1 | 5/2013 | Yokoyama et al. | |
| 2013/0200359 A1 | 8/2013 | Stoessel et al. | |
| 2014/0077179 A1* | 3/2014 | Shin ..................... | C07D 403/04 257/40 |

FOREIGN PATENT DOCUMENTS

| | | | |
|---|---|---|---|
| DE | 102009023155 A1 | 12/2010 | |
| JP | 201225745 A | 2/2012 | |
| JP | 201262450 A | 3/2012 | |
| JP | 2012528088 A | 11/2012 | |
| KR | 20120072787 A | 7/2012 | |
| TW | 201114742 A1 | 5/2011 | |
| WO | WO-2012014500 A1 | 2/2012 | |
| WO | WO-2012048781 A1 | 4/2012 | |
| WO | WO 2012067425 A1 * | 5/2012 | ........... C07D 403/04 |

OTHER PUBLICATIONS

International Search Report for PCT/EP2013/003456 dated Mar. 7, 2014.
English Translation of Japanese Office Action for Japanese Patent Application No. 2015-546882, dated Sep. 19, 2017.

* cited by examiner

Primary Examiner — Ruiyun Zhang
(74) Attorney, Agent, or Firm — Drinker Biddle & Reath LLP

(57) ABSTRACT

The present application relates to a compound of a formula (I) which contains an indenocarbazole group, a carbazole group and an electron-deficient group bonded to the indenocarbazole group. The compound is suitable for use in electronic devices, in particular in organic electroluminescent devices.

13 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2013/003456, filed Nov. 15, 2013, which claims benefit of European Application No. 12008332.4, filed Dec. 14, 2012, both of which are incorporated herein by reference in their entirety.

The present application relates to a compound of a formula (I) which contains an indenocarbazole group, a carbazole group and an electron-deficient heteroaryl group in one molecule. The compound can be used in an electronic device.

Electronic devices in the sense of this application are taken to mean, in particular, so-called organic electronic devices which comprise organic semiconductor materials as functional materials. Again in particular, these are taken to mean organic electroluminescent devices (OLEDs) and other electronic devices which are indicated below in the detailed description of the invention.

In general, the term OLED is taken to mean an electronic device which comprises at least one organic material and emits light on application of an electrical voltage. The precise structure of OLEDs is described, inter alia, in U.S. Pat. Nos. 4,539,507, 5,151,629, EP 0676461 and WO 98/27136.

There is major interest in improving the performance data of electronic devices, in particular OLEDs, in particular lifetime and efficiency and operating voltage. An important role is played here by organic emitter layers, in particular the matrix materials present therein, and organic layers having an electron-transporting function.

In order to achieve this technical object, there is a continuous search for novel materials which are suitable for use as matrix materials in emitting layers, in particular phosphorescent emitting layers. Furthermore, materials having electron-transporting and/or hole-blocking properties are sought for use in corresponding functional layers.

Phosphorescent emitting layers in the sense of the present application are organic layers which comprise at least one phosphorescent emitter compound.

Emitter compounds of an emitting layer are typically compounds which emit light on operation of the electronic device.

The term phosphorescent emitters in accordance with the present application encompasses compounds in which the light emission takes place through a spin-forbidden transition, for example a transition from an excited triplet state or a state having a relatively high spin quantum number, such as a quintet state.

A matrix material in a system comprising two or more materials is taken to mean the component whose proportion in the mixture is the greater. Correspondingly, a dopant in a system comprising two or more materials is taken to mean the component whose proportion in the mixture is the smaller. Instead of the term matrix material, the term host material is also used in many cases.

If an emitter compound is used in combination with one or more further compounds in an emitting layer, its proportion in the mixture is typically the relatively smaller. In this case, it may also be referred to as dopant compound. The one or more further compounds are typically present in the mixture in relatively larger proportion and can therefore be referred to in accordance with the above definition as matrix materials.

The use of compounds containing one or more carbazole groups in electronic devices is known from the prior art, for example from WO 2005/039246, US 2005/0069729, JP 2004/288381, EP 1205527 or WO 2008/086851.

The use of compounds containing one or more indenocarbazole groups in electronic devices is furthermore known from the prior art, for example from WO 2010/136109 and WO 2011/000455.

The use of compounds containing one or more electron-deficient hetero-aromatic six-membered rings in electronic devices is furthermore known from the prior art, for example from WO 2010/015306, WO 2007/063754 and WO 2008/056746.

However, there continues to be a demand for alternative compounds for use in electronic devices, in particular for use as matrix materials for phosphorescent emitting layers of organic electroluminescent devices.

The prior art again furthermore discloses the use of compounds which contain both one or more electron-deficient heteroaromatic six-membered rings, one or more carbazole groups and one or more indenocarbazole groups in electronic devices. Such compounds and their use in electronic devices are disclosed, for example, in WO 2010/136109, WO 2011/000455, WO 2012/069121 and WO 2012/014500.

However, there continues to be a need for improvement over these compounds, in particular in the respects of operating voltage, power efficiency and lifetime of devices comprising the compounds.

Surprisingly, it has now been found that excellent performance data can be achieved with a certain isomeric indenocarbazole compound which is connected to an electron-deficient six-membered heteroaromatic ring via its N atom and which carries a carbazole substituent bonded via one of its carbon atoms. In particular, an excellent lifetime and power efficiency are achieved on use in organic electroluminescent devices.

The present application thus relates to a compound of a formula (I)

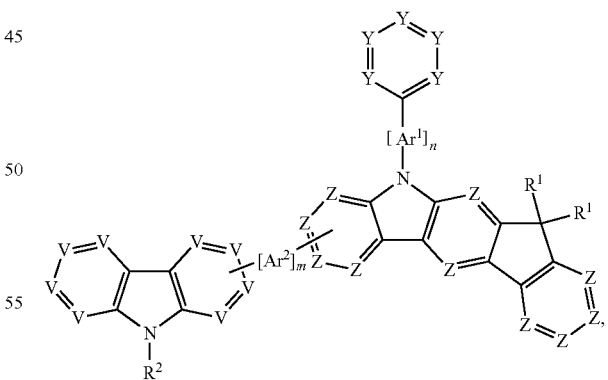

formula (I)

where:
Y is equal to N or $CR^1$, where at least two groups Y in the six-membered ring must be equal to N;
Z is equal to $CR^1$ or N;
V is equal to $CR^2$ or N;
$Ar^1$ is an aromatic or heteroaromatic ring system having 6 to 40 aromatic ring atoms, which may be substituted by one or more radicals $R^1$;

Ar$^2$ is an aromatic or heteroaromatic ring system having 6 to 40 aromatic ring atoms, which may be substituted by one or more radicals R$^1$;

R$^1$ is on each occurrence, identically or differently, H, D, F, Br, Cl, I, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$, or an aromatic or heteroaromatic ring system having 5 to 30 aromatic ring atoms, which may in each case be substituted by one or more radicals R$^3$, or an aryloxy or heteroaryloxy group having 5 to 30 aromatic ring atoms, which may be substituted by one or more radicals R$^3$, where two or more radicals R$^1$ may be linked to one another and may form a ring;

R$^2$ is on each occurrence, identically or differently, H, D, F, Br, Cl, I, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$, or an aromatic or heteroaromatic ring system having 5 to 30 aromatic ring atoms, which may in each case be substituted by one or more radicals R$^3$, or an aryloxy or heteroaryloxy group having 5 to 30 aromatic ring atoms, which may be substituted by one or more radicals R$^3$;

R$^3$ is on each occurrence, identically or differently, H, D, F, Br, Cl, I, C(=O)R$^4$, CN, Si(R$^4$)$_3$, N(R$^4$)$_2$, P(=O)(R$^4$)$_2$, S(=O)R$^4$, S(=O)$_2$R$^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$, or an aromatic or heteroaromatic ring system having 5 to 30 aromatic ring atoms, which may in each case be substituted by one or more radicals R$^4$, or an aryloxy or heteroaryloxy group having 5 to 30 aromatic ring atoms, which may be substituted by one or more radicals R$^4$, where two or more radicals R$^3$ may be linked to one another and may form a ring;

R$^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents R$^4$ here may be linked to one another and may form a ring;

n is equal to 0 or 1;

m is equal to 0 or 1;

where the index n is equal to 0 if, in formula (I), both
a) not more than two groups Y which are equal to N are present and also
b) these two groups Y which are equal to N are located in the meta-position to one another on the six-membered ring.

The expression that groups Y which are equal to N are located in the meta-position to one another on the six-membered ring is, for the purposes of the present application, taken to mean that the groups Y which are equal to N are not adjacent in the six-membered ring, but instead that precisely one other group Y is located between them. The groups Y which are equal to N are thus arranged in the six-membered ring in such a way that the next group Y but one is in each case the group which is equal to N and the next group Y is equal to CR$^1$.

For the purposes of the present application, the following definitions of chemical groups apply:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or hetero-aromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spiro-truxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromehylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octenylthio.

The formulation that two or more radicals may form a ring with one another is, for the purposes of the present application, intended to be taken to mean, inter alia, that the two radicals are linked to one another by a chemical bond. This is illustrated by the following scheme:

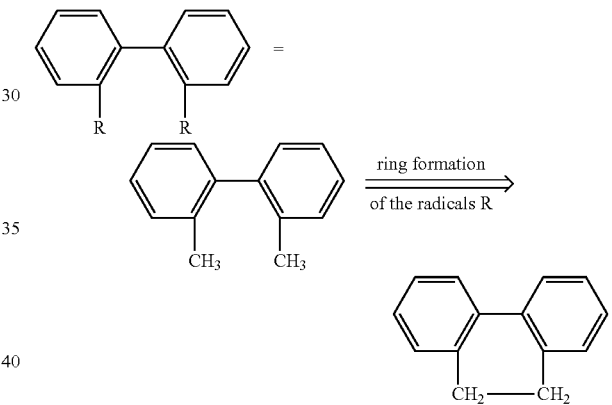

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

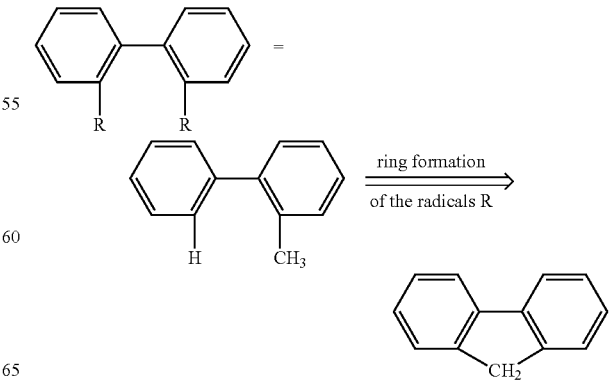

In accordance with a preferred embodiment, the index m is equal to 0.

In accordance with a further preferred embodiment, the index n is equal to 0 if not more than two groups Y in the six-membered ring are equal to N. In accordance with a particularly preferred embodiment, the index n is equal to 0 or 1 if precisely three groups Y in the six-membered ring are equal to N, and in all other cases the index n is equal to 0.

In accordance with a further preferred embodiment, a maximum of three groups Z in an aromatic ring are equal to N, particularly preferably a maximum of two groups Z in an aromatic ring are equal to N, and very particularly preferably a maximum of one group Z in an aromatic ring is equal to N.

It is furthermore preferred for not more than two adjacent groups Z in a six-membered ring to be equal to N.

It is especially preferred for Z to be equal to $CR^1$.

In accordance with a further preferred embodiment, a maximum of three groups V in an aromatic ring are equal to N, particularly preferably a maximum of two groups V in an aromatic ring are equal to N, and very particularly preferably a maximum of one group V in an aromatic ring is equal to N.

It is furthermore preferred for not more than two adjacent groups V in a six-membered ring to be equal to N.

It is especially preferred for V to be equal to $CR^2$.

For the group Y, it is preferred for precisely two or precisely three groups Y in the ring to be equal to N, and for the remaining groups Y to be equal to $CR^1$. It is particularly preferred for precisely three groups Y in the ring to be equal to N, and for the remaining groups Y to be equal to $CR^1$. For the group Y, it is furthermore preferred for not more than two adjacent groups Y to be equal to N, particularly preferably no adjacent groups Y are equal to N.

In accordance with a further preferred embodiment, radicals $R^1$ in groups Y which represent $CR^1$ form a ring with one another. These are preferably radicals $R^1$ in adjacent groups Y which represent $CR^1$. In this case, the radicals $R^1$ in adjacent groups Y which represent $CR^1$ particularly preferably form a condensed-on benzene ring. In this case, it is very particularly preferred for precisely two groups Y to be equal to N.

For the group $Ar^1$, it is preferred for it to represent a group of the following formula ($Ar^1$—I)

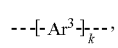

formula ($Ar^1$-I)

where the dashed lines represent the bonds to the indenocarbazole group and the six-membered ring containing the groups Y, $Ar^3$ is on each occurrence, identically or differently, an aryl or heteroaryl group having 6 to 18 aromatic ring atoms, which may be substituted by one or more radicals $R^1$, where $R^1$ is defined as above; and k is 1, 2, 3 or 4, where the index k is selected so that the number of aromatic ring atoms in the entire group $Ar^1$ does not exceed the number 40.

$Ar^3$ is preferably on each occurrence, identically or differently, an aryl or heteroaryl group having 6 to 14 aromatic ring atoms, particularly preferably an aryl or heteroaryl group having 6 to 10 aromatic ring atoms, and very particularly preferably an aryl or heteroaryl group having 6 aromatic ring atoms, where the said groups may be substituted by one or more radicals $R^1$.

In accordance with a preferred embodiment, radicals $R^1$ here form rings between the aryl or heteroaryl groups $Ar^3$ to which they are bonded. Especially preferably, two groups $Ar^3$ which represent phenyl are connected to form a fluorenyl group.

The index k is preferably 1, 2 or 3, particularly preferably 1 or 2.

Preferred embodiments of the group $Ar^1$ conform to the formulae ($Ar^1$—I-1) to ($Ar^1$—I-26) indicated below:

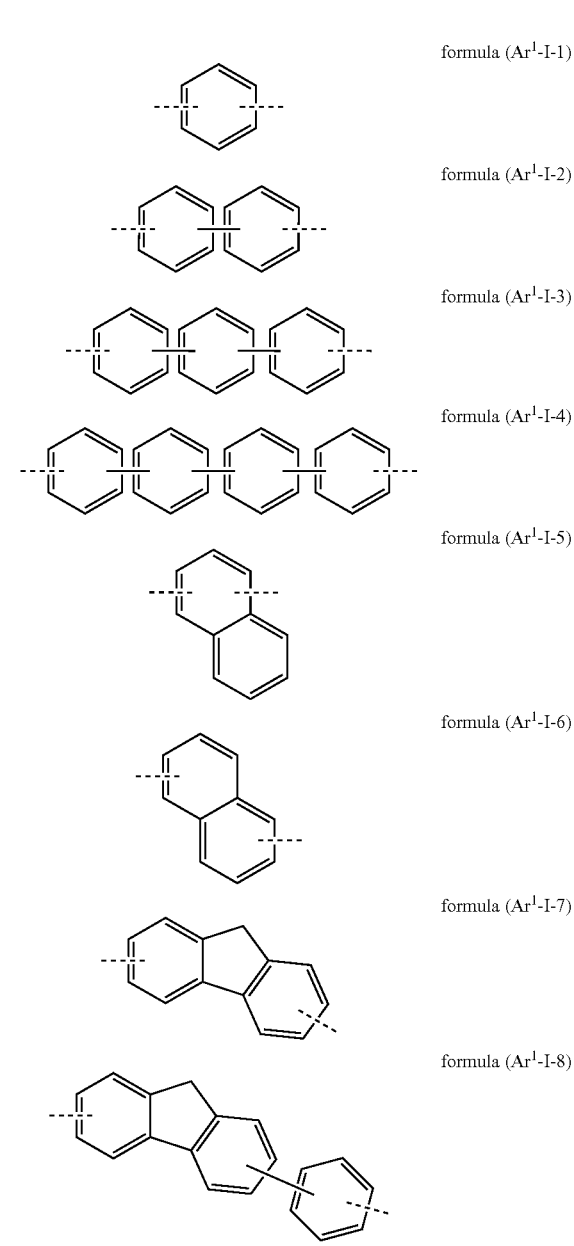

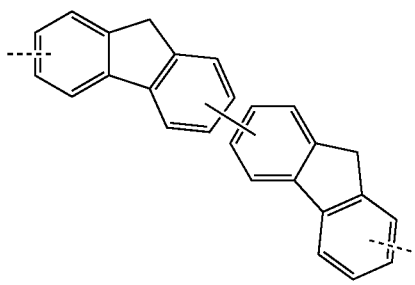 formula (Ar¹-I-9)

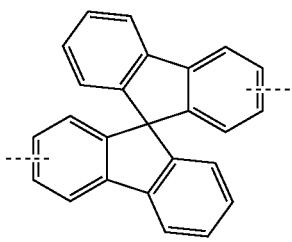 formula (Ar¹-I-10)

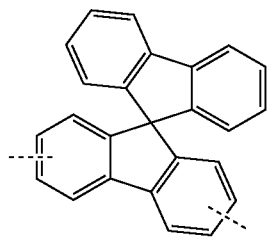 formula (Ar¹-I-11)

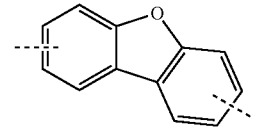 formula (Ar¹-I-12)

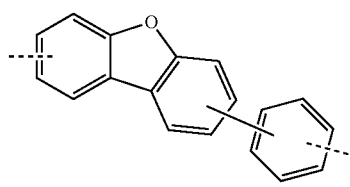 formula (Ar¹-I-13)

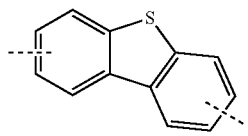 formula (Ar¹-I-14)

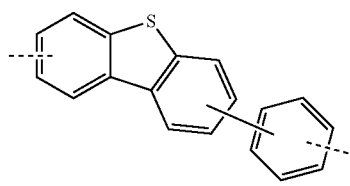 formula (Ar¹-I-15)

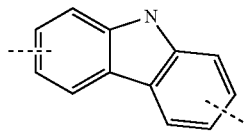 formula (Ar¹-I-16)

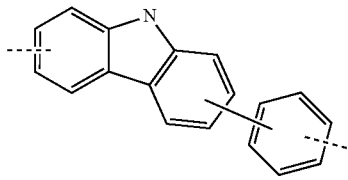 formula (Ar¹-I-17)

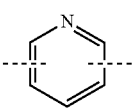 formula (Ar¹-I-18)

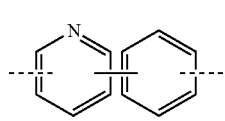 formula (Ar¹-I-19)

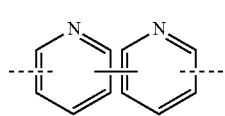 formula (Ar¹-I-20)

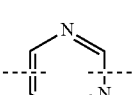 formula (Ar¹-I-21)

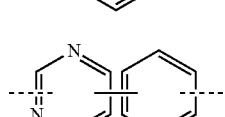 formula (Ar¹-I-22)

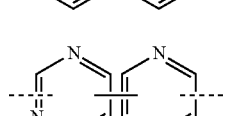 formula (Ar¹-I-23)

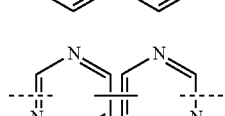 formula (Ar¹-I-24)

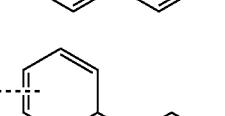 formula (Ar¹-I-25)

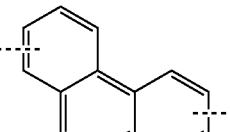 formula (Ar¹-I-26)

where the dashed lines represent the bonds to the indeno-carbazole group and the six-membered ring containing the groups Y,
and where the groups may be substituted by radicals $R^1$ at all free positions.

For the group $Ar^2$, it is preferred for it to be selected from an aromatic or heteroaromatic ring system having 6 to 30 aromatic ring atoms, particularly preferably 6 to 24 aromatic ring atoms, which may be substituted by one or more radicals $R^1$.

Preferred embodiments of the group of the formula (Y)

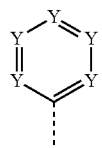

formula (Y)

as constituent of the formula (I) conform to the following formulae (Y-1) to (Y-6):

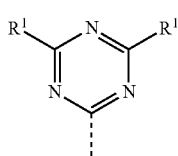

formula (Y-1)

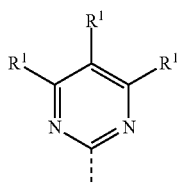

formula (Y-2)

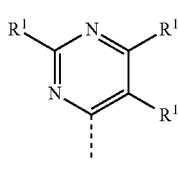

formula (Y-3)

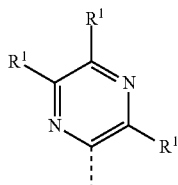

formula (Y-4)

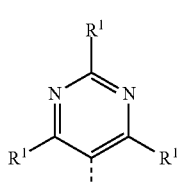

formula (Y-5)

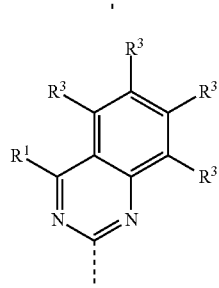

formula (Y-6)

where the dashed line denotes the bond to the remainder of the compound and where $R^1$ and $R^3$ are as defined above.

Of these, formula (Y-1) is particularly preferred.

The radical $R^1$ is preferably on each occurrence, identically or differently, H, D, F, CN, $Si(R^3)_3$, $N(R^3)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$ and where one or more $CH_2$ groups in the above-mentioned groups may be replaced by —C≡C—, —$R^3$C=C$R^3$—, $Si(R^3)_2$, C=O, C=N$R^3$, —N$R^3$—, —O—, —S—, —C(=O)O— or —C(=O)N$R^3$—, or an aromatic or heteroaromatic ring system having 5 to 20 aromatic ring atoms, which may in each case be substituted by one or more radicals $R^3$, where two or more radicals $R^1$ may be linked to one another and may form a ring.

The radical $R^2$ is preferably on each occurrence, identically or differently, H, D, F, CN, $Si(R^3)_3$, $N(R^3)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$ and where one or more $CH_2$ groups in the above-mentioned groups may be replaced by —C≡C—, —$R^3$C=C$R^3$—, $Si(R^3)_2$, C=O, C=N$R^3$, —N$R^3$—, —O—, —S—, —C(=O)O— or —C(=O)N$R^3$—, or an aromatic or heteroaromatic ring system having 5 to 20 aromatic ring atoms, which may in each case be substituted by one or more radicals $R^3$.

The radical $R^3$ is preferably on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more $CH_2$ groups in the above-mentioned groups may be replaced by —C≡C—, $R^4$C=C$R^4$—, $Si(R^4)_2$, C=O, C=N$R^4$, —N$R^4$—, —O—, —S—, —C(=O)O— or —C(=O)N$R^4$—, or an aromatic or heteroaromatic ring system having 5 to 20 aromatic ring atoms, which may in each case be substituted by one or more radicals $R^4$, where two or more radicals $R^3$ may be linked to one another and may form a ring.

Regarding the bonding of the group $Ar^2$ to the indenocarbazole, it is preferred for this to be in the positions denoted by "a" and "b", particularly preferably in the position denoted by "a", in formula (I-A) below. A corresponding situation applies, if the index m is equal to 0, to the carbazole group bonded instead of $Ar^2$.

In the formula (I-A),

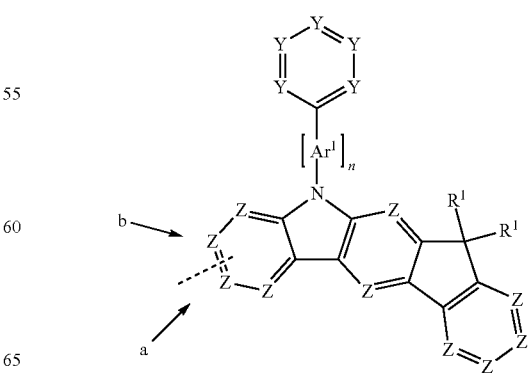

the dashed line denotes the bond to the remainder of the formula (I), and the above-mentioned positions "a" and "b" are denoted by arrows.

Regarding the bonding of the group $Ar^2$ to the carbazole, it is preferred for this to be in the positions denoted by "c" and "d", particularly preferably in the position denoted by "c", in formula (I-B) below. A corresponding situation applies, if the index m is equal to 0, for the indenocarbazole group bonded instead of $Ar^2$.

In the formula (I-B),

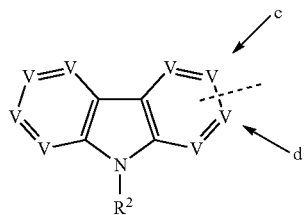

the dashed line denotes the bond to the remainder of the formula (I), and the above-mentioned positions "c" and "d" are denoted by arrows.

Preferred embodiments of the compound of the formula (I) conform to one of the following formulae (I-1) and (I-2):

formula (I-1)

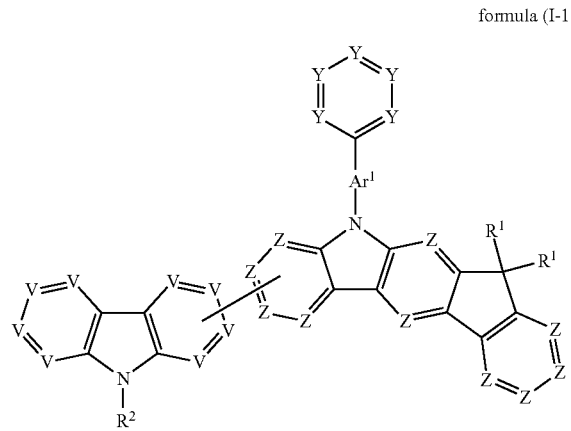

formula (I-2)

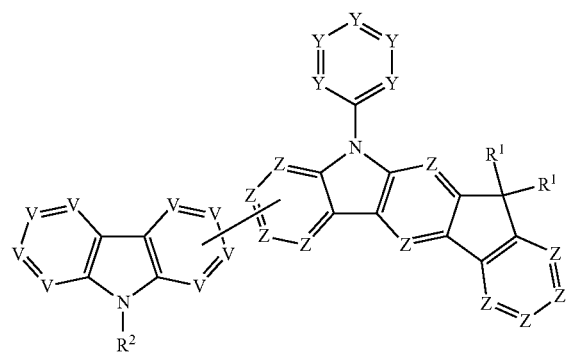

where the symbols occurring are as defined above, and, for formula (I-1), the case must not occur where not more than two groups Y which are equal to N are present and these two groups Y which are equal to N are located in the meta-position to one another on the six-membered ring.

For formula (I-1), it is preferred for more than two, particularly preferably precisely three, groups Y in the six-membered ring to be equal to N.

For the formulae (I-1) and (I-2), preference is furthermore given to the above-mentioned preferred embodiments of the groups $Ar^1$, Z, V, $R^1$ and $R^2$.

Furthermore, preference is likewise given to the above-mentioned preferred embodiments regarding the position of the bond between indenocarbazole and carbazole.

Furthermore preferably, the six-membered ring containing the groups Y in the formulae (I-1) and (I-2) preferably conforms to one of the above-mentioned formulae (Y-1) to (Y-6), particularly preferably to the formula (Y-1).

Particularly preferred embodiments of compounds of the formula (I) conform to the following formulae (I-1-1) to (I-1-3) and (I-2-1) to (I-2-3):

formula (I-1-1)

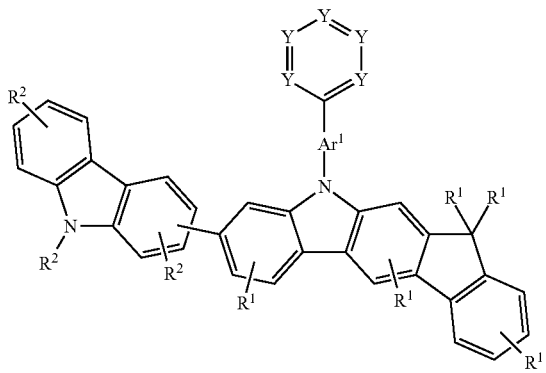

formula (I-1-2)

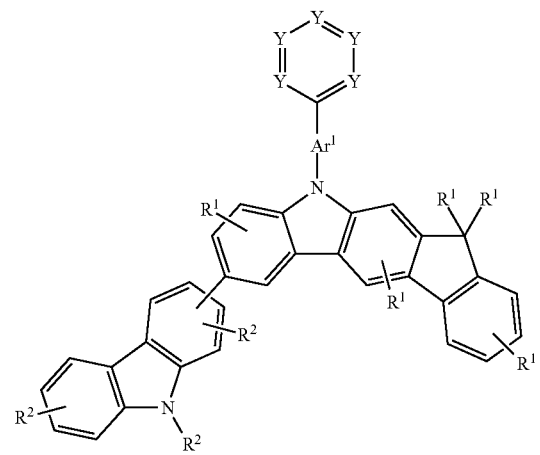

-continued formula (I-1-3)

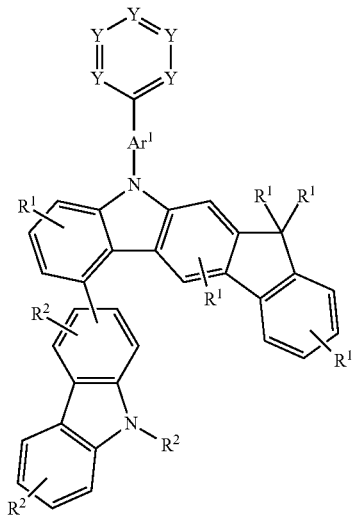

formula (I-2-3)

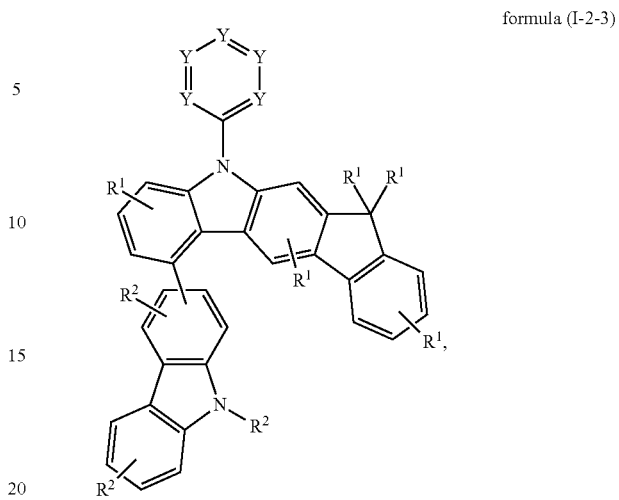

formula (I-2-1)

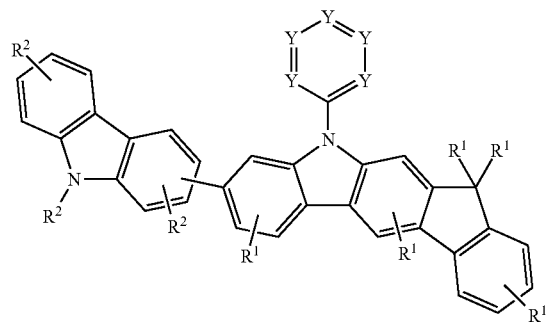

formula (I-2-2)

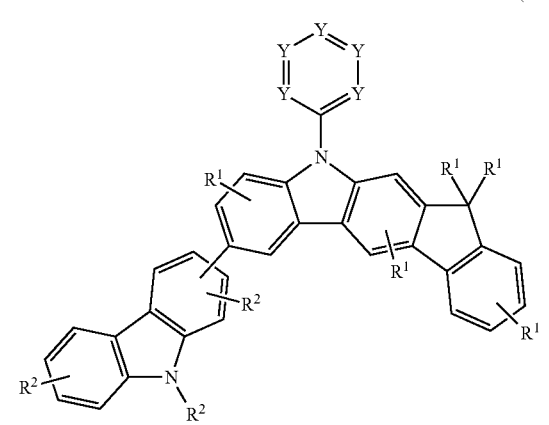

where the groups occurring are as defined above, and where a bonded radical $R^1$ or $R^2$ on a six-membered ring means that all free positions of the six-membered ring may each be substituted by radicals $R^1$ or $R^2$, and where, for the formulae (I-1-1) to (I-1-3), more than two, preferably precisely three, groups Y in the six-membered ring are equal to N.

For the formulae (I-1-1) to (I-1-3) and (I-2-1) to (I-2-3), preference is furthermore given to the above-mentioned preferred embodiments of the groups $Ar^1$, $R^1$ and $R^2$.

It is furthermore preferred for the carbazole in the above-mentioned formulae to be bonded in one of positions "c" and "d", as indicated above for formula (I-B), particularly preferably in position "c".

Furthermore, the six-membered ring containing the groups Y in the above-mentioned formulae preferably conforms to one of the above-mentioned formulae (Y-1) to (Y-6), particularly preferably to the formula (Y-1).

Of the formulae (I-1-1) to (I-1-3) and (I-2-1) to (I-2-3), particular preference is given to the two formulae (I-1-2) and (I-2-2), in particular in combination with the above-mentioned preferred embodiments of the groups $R^1$ and $R^2$ and $Ar^1$.

The following table shows examples of compounds of the formula (I):

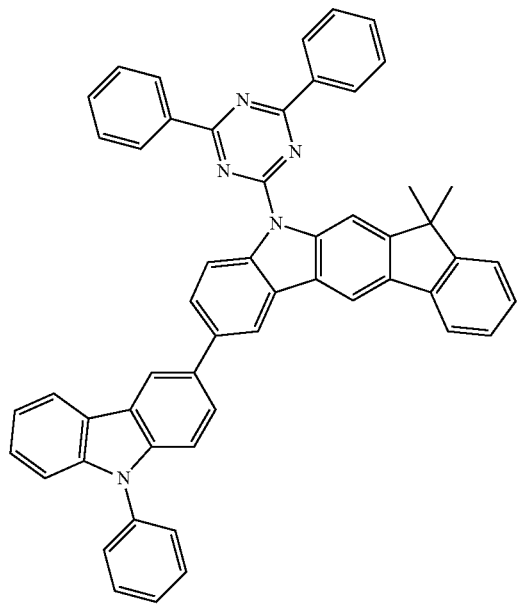 [SMILES: CC1(C)c2ccccc2-c2cc3c4cc(-c5ccc6c(c5)c5ccccc5n6-c5ccccc5)ccc4n(-c4nc(-c5ccccc5)nc(-c5ccccc5)n4)c3cc21]
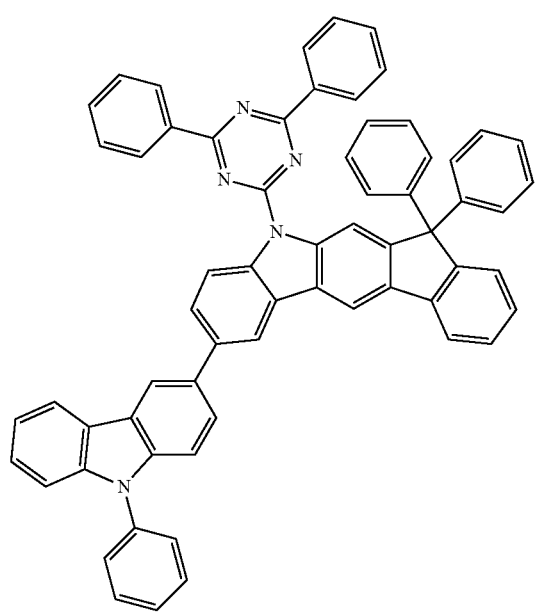 [SMILES: c1ccc(-c2nc(-c3ccccc3)nc(-n3c4ccc(-c5ccc6c(c5)c5ccccc5n6-c5ccccc5)cc4c4cc5c(cc43)C(c3ccccc3)(c3ccccc3)c3ccccc3-5)n2)cc1]

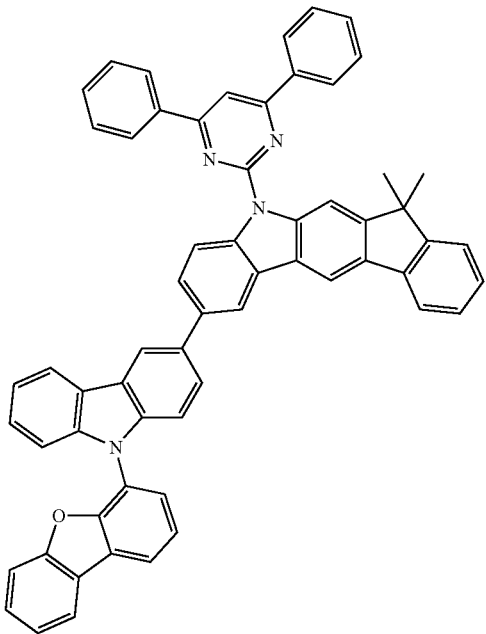 [SMILES: CC1(C)c2ccccc2-c2cc3c4cc(-c5ccc6c(c5)c5ccccc5n6-c5cccc6c5oc5ccccc56)ccc4n(-c4nc(-c5ccccc5)cc(-c5ccccc5)n4)c3cc21]
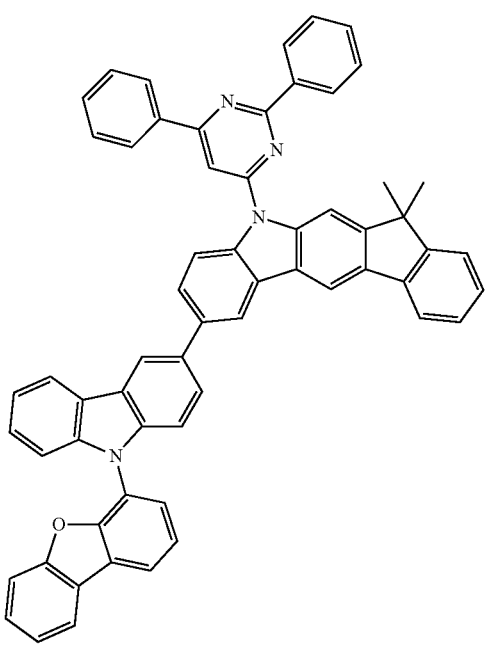 [SMILES: CC1(C)c2ccccc2-c2cc3c4cc(-c5ccc6c(c5)c5ccccc5n6-c5cccc6c5oc5ccccc56)ccc4n(-c4cc(-c5ccccc5)nc(-c5ccccc5)n4)c3cc21]

-continued
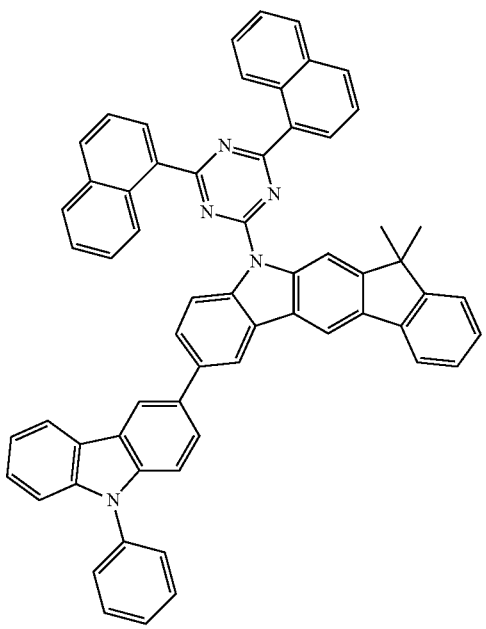 [SMILES: CC1(C)c2ccccc2-c2cc3c4cc(-c5ccc6c(c5)c5ccccc5n6-c5ccccc5)ccc4n(-c4nc(-c5cccc6ccccc56)nc(-c5cccc6ccccc56)n4)c3cc21]
5
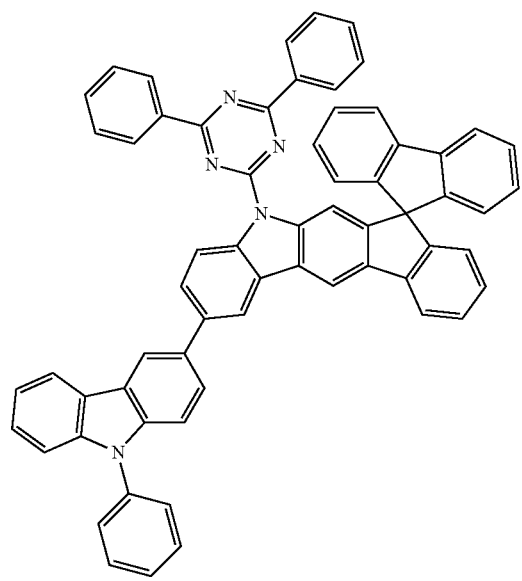 [SMILES: c1ccc(-c2nc(-c3ccccc3)nc(-n3c4ccc(-c5ccc6c(c5)c5ccccc5n6-c5ccccc5)cc4c4cc5c(cc43)C3(c4ccccc4-c4ccccc43)c3ccccc3-5)n2)cc1]
6

-continued
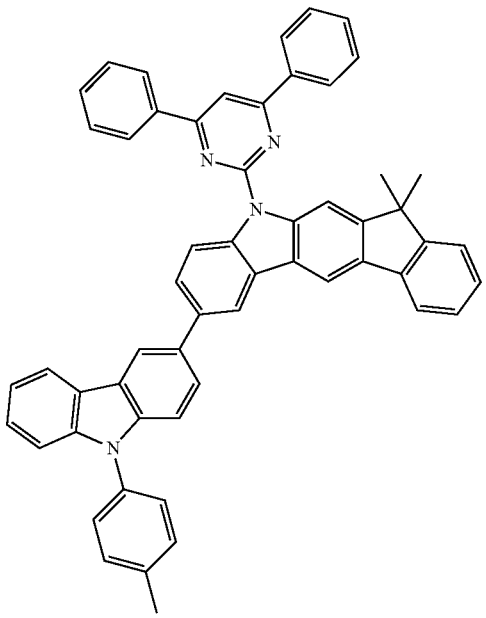 [SMILES: Cc1ccc(-n2c3ccccc3c3cc(-c4ccc5c(c4)c4cc6c(cc4n5-c4nc(-c5ccccc5)cc(-c5ccccc5)n4)C(C)(C)c4ccccc4-6)ccc32)cc1]
7
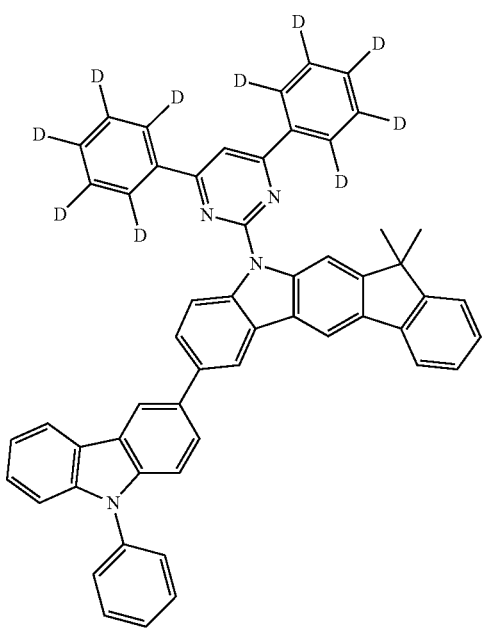 [SMILES: [2H]c1c([2H])c([2H])c(-c2cc(-c3c([2H])c([2H])c([2H])c([2H])c3[2H])nc(-n3c4ccc(-c5ccc6c(c5)c5ccccc5n6-c5ccccc5)cc4c4cc5c(cc43)C(C)(C)c3ccccc3-5)n2)c([2H])c1[2H]]
8

-continued
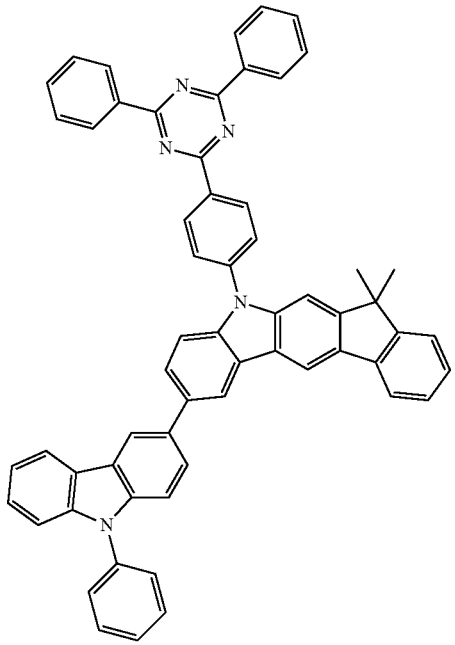
9
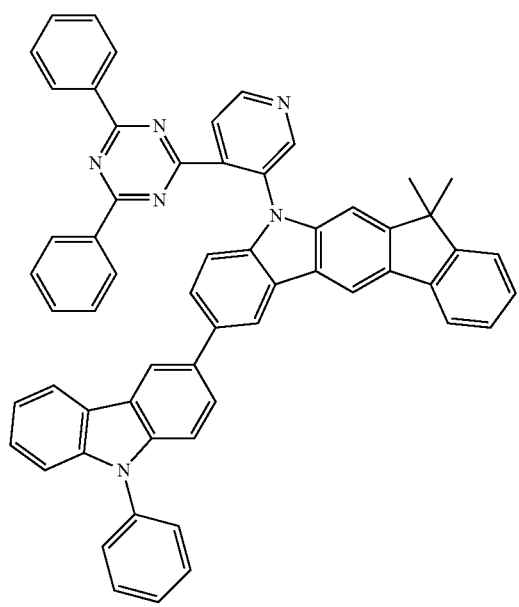 [SMILES: CC1(C)c2ccccc2-c2cc3c4cc(-c5ccc6c(c5)c5ccccc5n6-c5ccccc5)ccc4n(-c4cnccc4-c4nc(-c5ccccc5)nc(-c5ccccc5)n4)c3cc21]
10

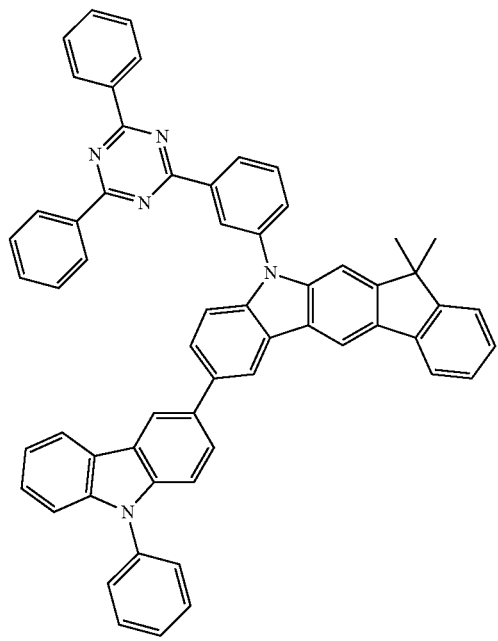 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21]
11
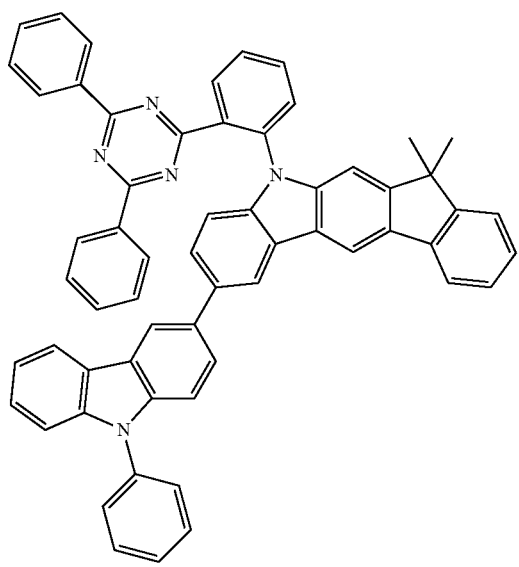 [SMILES: CC1(C)c2ccccc2-c2cc3c4cc(-c5ccc6c(c5)c5ccccc5n6-c5ccccc5)ccc4n(-c4ccccc4-c4nc(-c5ccccc5)nc(-c5ccccc5)n4)c3cc21]
12

-continued
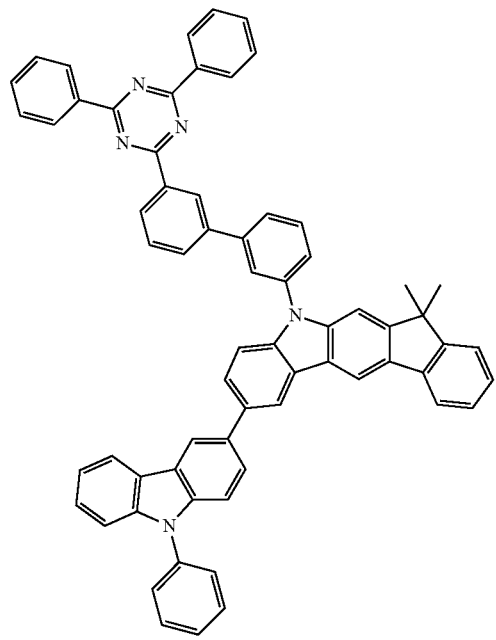 [SMILES: CC1(C)c2ccccc2-c2cc3c4cc(-c5ccc6c(c5)c5ccccc5n6-c5ccccc5)ccc4n(-c4cccc(-c5cccc(-c6nc(-c7ccccc7)nc(-c7ccccc7)n6)c5)c4)c3cc21]
13
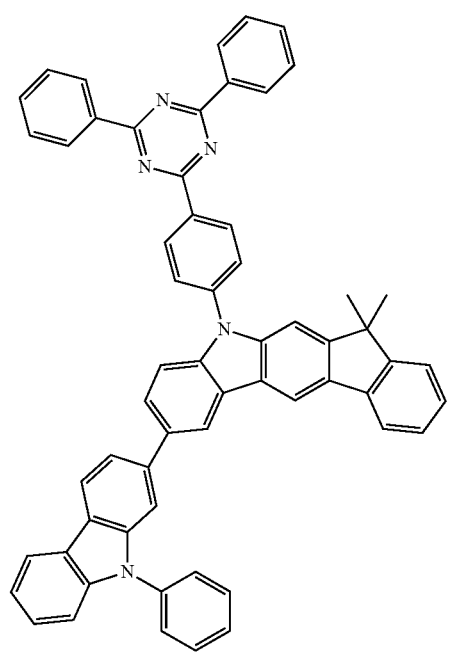 [SMILES: CC1(C)c2ccccc2-c2cc3c4cc(-c5ccc6c7ccccc7n(-c7ccccc7)c6c5)ccc4n(-c4ccc(-c5nc(-c6ccccc6)nc(-c6ccccc6)n5)cc4)c3cc21]
14

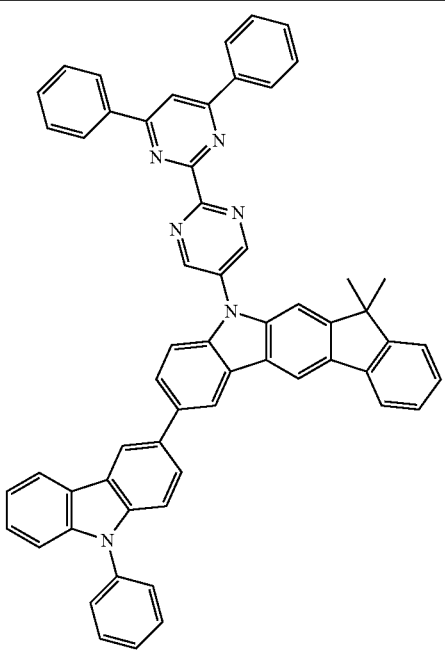
15
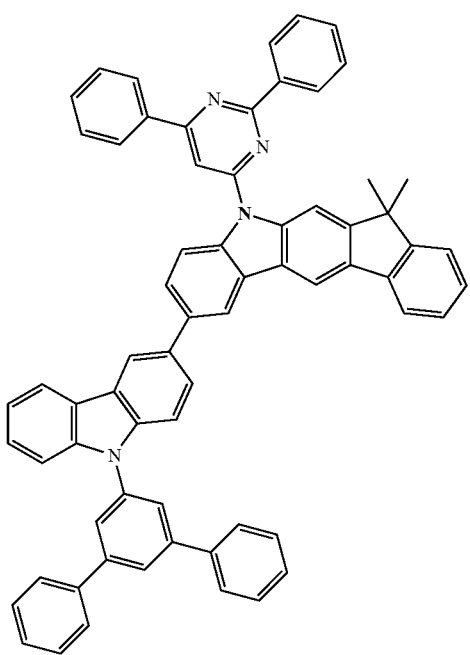 [SMILES: CC1(C)c2ccccc2-c2cc3c4cc(-c5ccc6c(c5)c5ccccc5n6-c5cc(-c6ccccc6)cc(-c6ccccc6)c5)ccc4n(-c4cc(-c5ccccc5)nc(-c5ccccc5)n4)c3cc21]
16

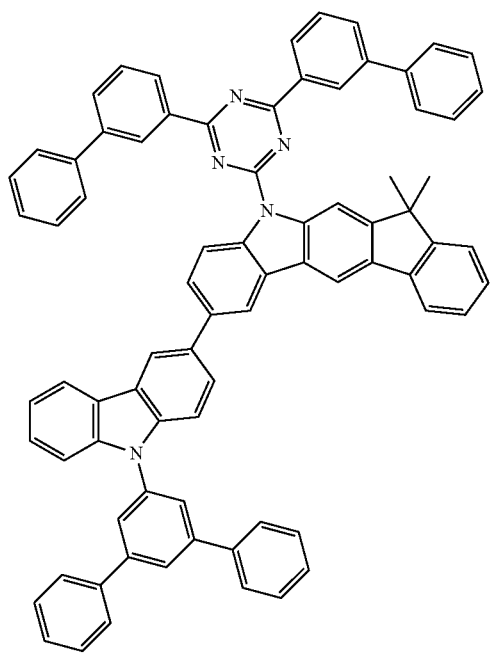 [SMILES: CC1(C)c2ccccc2-c2cc3c4cc(-c5ccc6c(c5)c5ccccc5n6-c5cc(-c6ccccc6)cc(-c6ccccc6)c5)ccc4n(-c4nc(-c5cccc(-c6ccccc6)c5)nc(-c5cccc(-c6ccccc6)c5)n4)c3cc21]
17
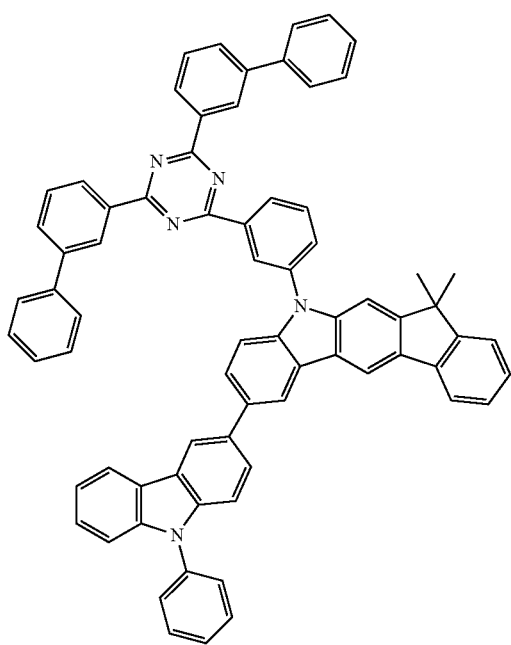 [SMILES: CC1(C)c2ccccc2-c2cc3c4cc(-c5ccc6c(c5)c5ccccc5n6-c5ccccc5)ccc4n(-c4cccc(-c5nc(-c6cccc(-c7ccccc7)c6)nc(-c6cccc(-c7ccccc7)c6)n5)c4)c3cc21]
18

-continued
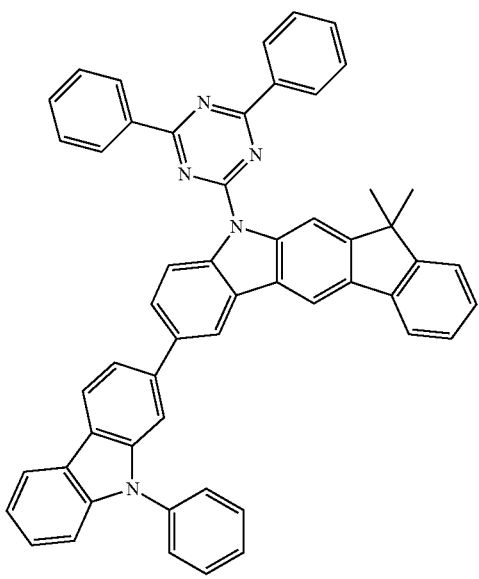 [SMILES: CC1(C)c2ccccc2-c2cc3c4cc(-c5ccc6c7ccccc7n(-c7ccccc7)c6c5)ccc4n(-c4nc(-c5ccccc5)nc(-c5ccccc5)n4)c3cc21]
19
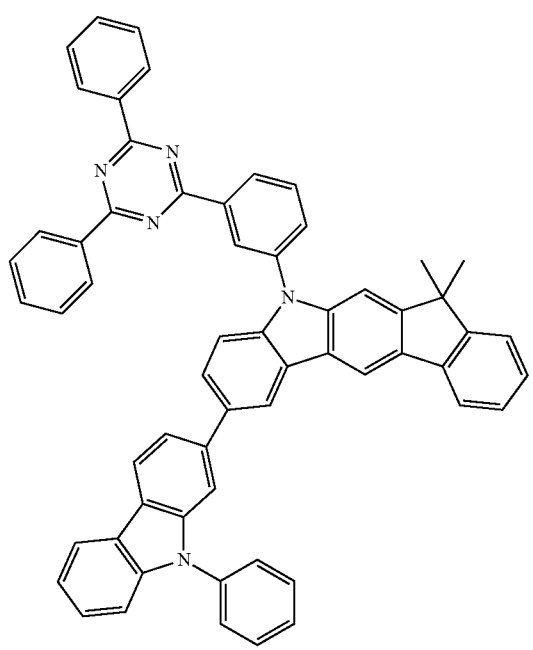 [SMILES: CC1(C)c2ccccc2-c2cc3c4cc(-c5ccc6c7ccccc7n(-c7ccccc7)c6c5)ccc4n(-c4cccc(-c5nc(-c6ccccc6)nc(-c6ccccc6)n5)c4)c3cc21]
20

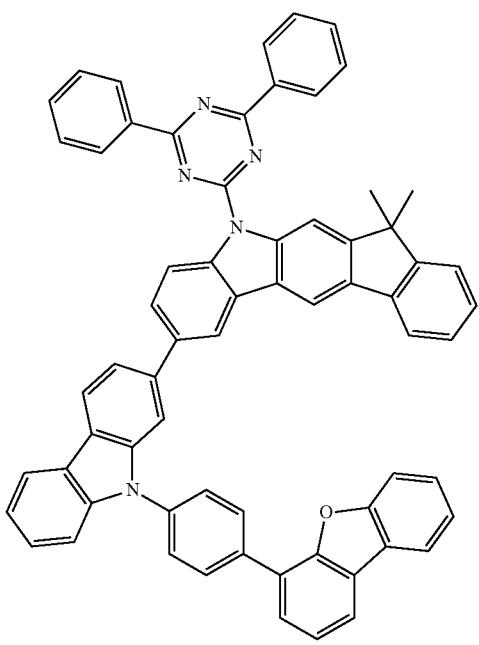 [SMILES: CC1(C)c2ccccc2-c2cc3c4cc(-c5ccc6c7ccccc7n(-c7ccc(-c8cccc9c8oc8ccccc89)cc7)c6c5)ccc4n(-c4nc(-c5ccccc5)nc(-c5ccccc5)n4)c3cc21]
21
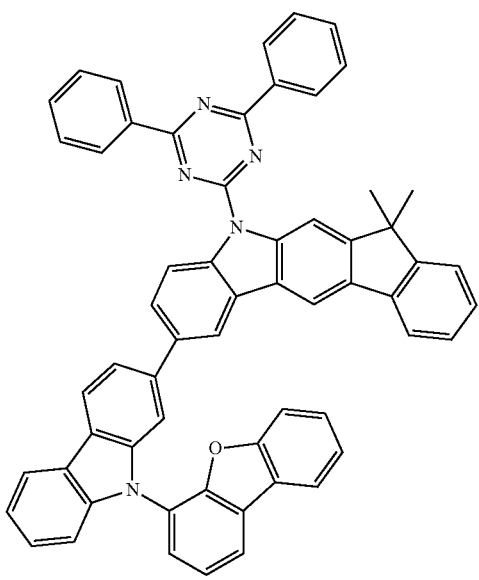 [SMILES: CC1(C)c2ccccc2-c2cc3c4cc(-c5ccc6c7ccccc7n(-c7cccc8c7oc7ccccc78)c6c5)ccc4n(-c4nc(-c5ccccc5)nc(-c5ccccc5)n4)c3cc21]
22

-continued
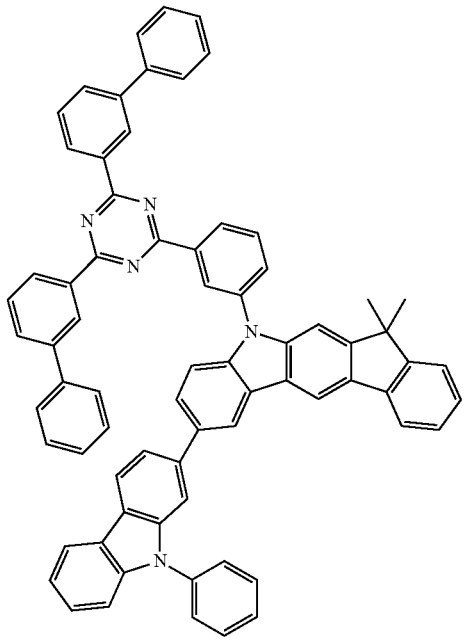 [SMILES: CC1(C)c2ccccc2-c2cc3c4cc(-c5ccc6c7ccccc7n(-c7ccccc7)c6c5)ccc4n(-c4cccc(-c5nc(-c6cccc(-c7ccccc7)c6)nc(-c6cccc(-c7ccccc7)c6)n5)c4)c3cc21]
23
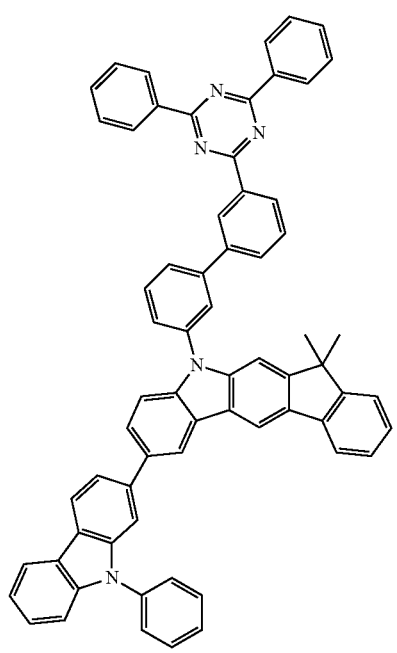 [SMILES: CC1(C)c2ccccc2-c2cc3c4cc(-c5ccc6c7ccccc7n(-c7ccccc7)c6c5)ccc4n(-c4cccc(-c5cccc(-c6nc(-c7ccccc7)nc(-c7ccccc7)n6)c5)c4)c3cc21]
24

-continued
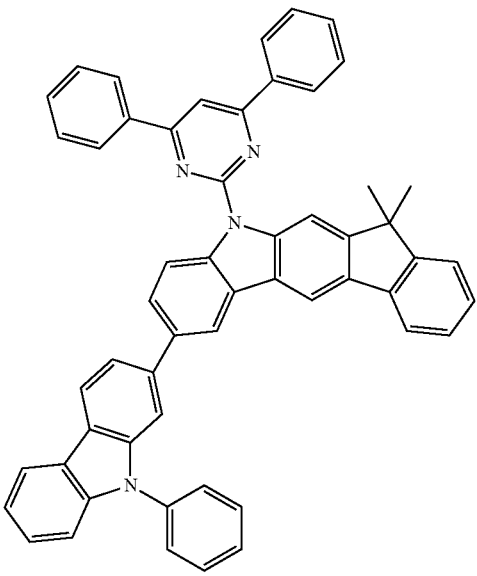 [SMILES: CC1(C)c2ccccc2-c2cc3c4cc(-c5ccc6c7ccccc7n(-c7ccccc7)c6c5)ccc4n(-c4nc(-c5ccccc5)cc(-c5ccccc5)n4)c3cc21]
25
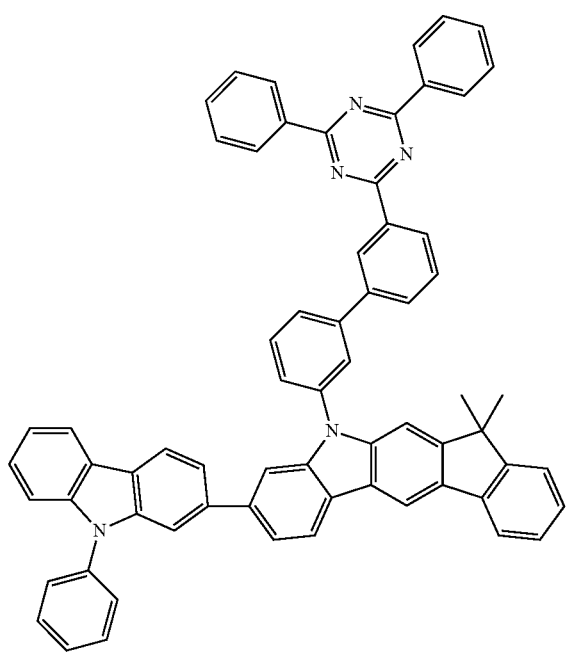 [SMILES: CC1(C)c2ccccc2-c2cc3c4ccc(-c5ccc6c7ccccc7n(-c7ccccc7)c6c5)cc4n(-c4cccc(-c5cccc(-c6nc(-c7ccccc7)nc(-c7ccccc7)n6)c5)c4)c3cc21]
26
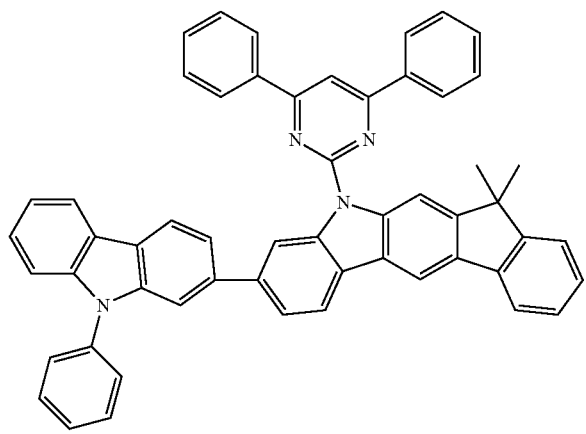 [SMILES: CC1(C)c2ccccc2-c2cc3c4ccc(-c5ccc6c7ccccc7n(-c7ccccc7)c6c5)cc4n(-c4nc(-c5ccccc5)cc(-c5ccccc5)n4)c3cc21]
27

-continued
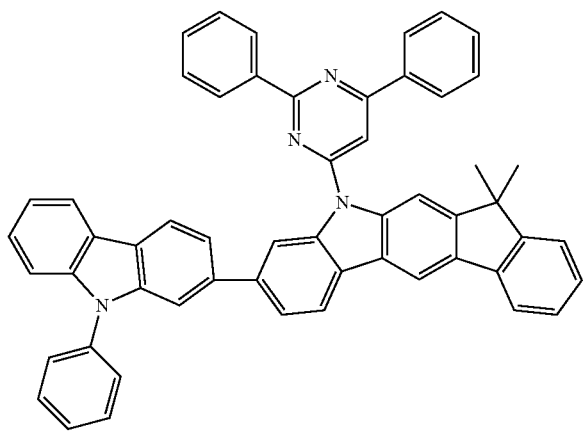 [SMILES: CC1(C)c2ccccc2-c2cc3c4ccc(-c5ccc6c7ccccc7n(-c7ccccc7)c6c5)cc4n(-c4cc(-c5ccccc5)nc(-c5ccccc5)n4)c3cc21]
28
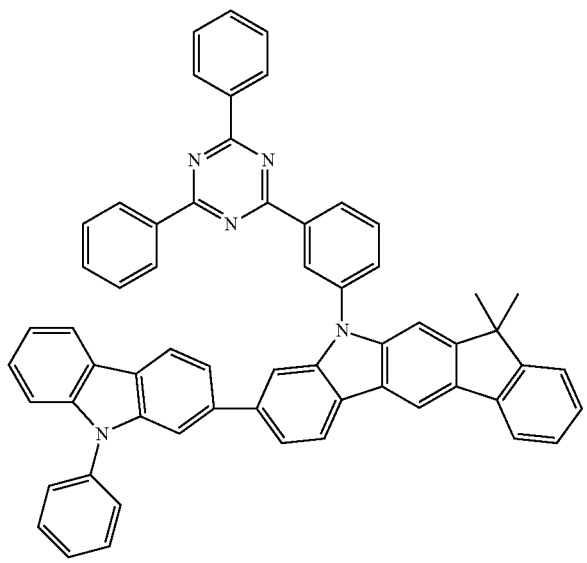 [SMILES: CC1(C)c2ccccc2-c2cc3c4ccc(-c5ccc6c7ccccc7n(-c7ccccc7)c6c5)cc4n(-c4cccc(-c5nc(-c6ccccc6)nc(-c6ccccc6)n5)c4)c3cc21]
29
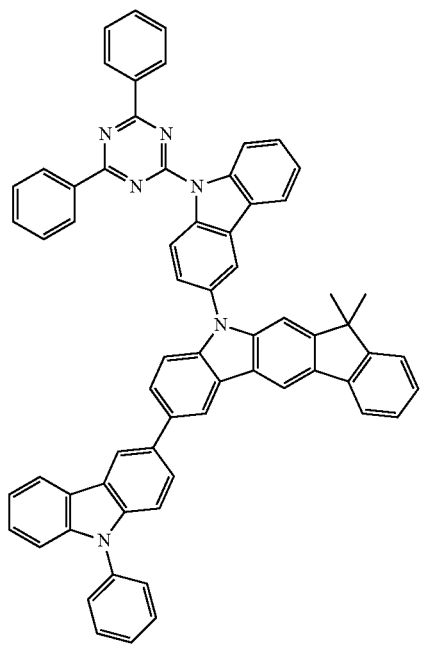 [SMILES: CC1(C)c2ccccc2-c2cc3c4cc(-c5ccc6c(c5)c5ccccc5n6-c5ccccc5)ccc4n(-c4ccc5c(c4)c4ccccc4n5-c4nc(-c5ccccc5)nc(-c5ccccc5)n4)c3cc21]
30

-continued
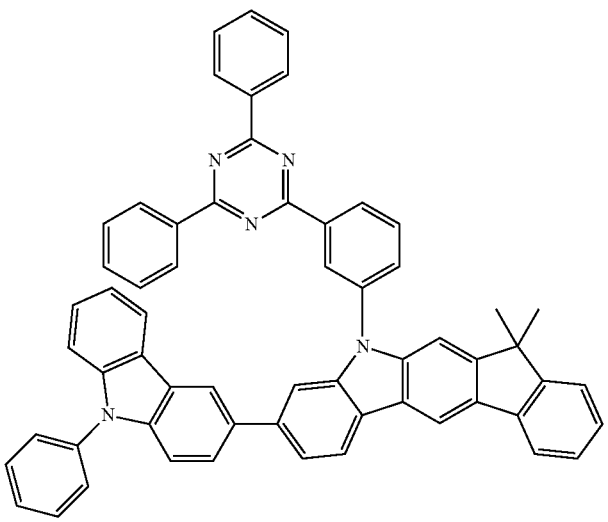 [SMILES: CC1(C)c2ccccc2-c2cc3c4ccc(-c5ccc6c(c5)c5ccccc5n6-c5ccccc5)cc4n(-c4cccc(-c5nc(-c6ccccc6)nc(-c6ccccc6)n5)c4)c3cc21]
31
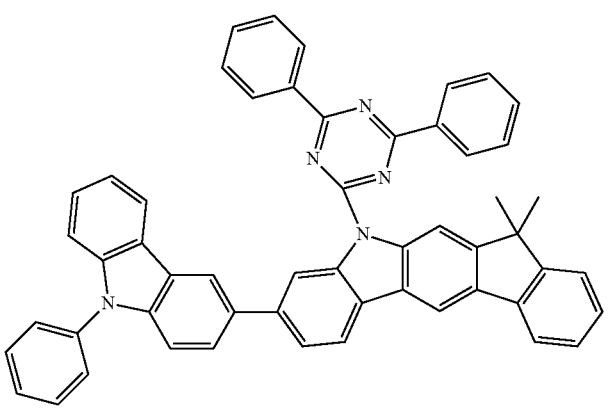 [SMILES: CC1(C)c2ccccc2-c2cc3c4ccc(-c5ccc6c(c5)c5ccccc5n6-c5ccccc5)cc4n(-c4nc(-c5ccccc5)nc(-c5ccccc5)n4)c3cc21]
32
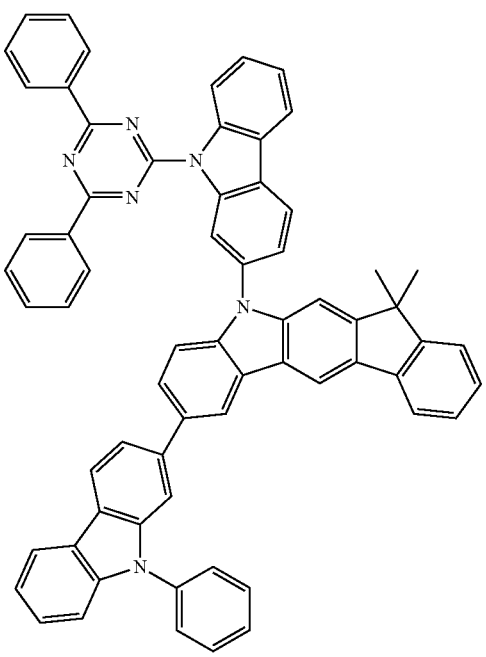 [SMILES: CC1(C)c2ccccc2-c2cc3c4cc(-c5ccc6c7ccccc7n(-c7ccccc7)c6c5)ccc4n(-c4ccc5c6ccccc6n(-c6nc(-c7ccccc7)nc(-c7ccccc7)n6)c5c4)c3cc21]
33

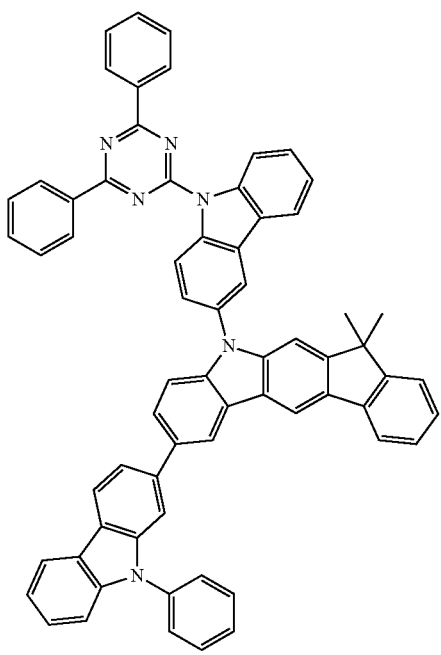 [SMILES: CC1(C)c2ccccc2-c2cc3c4cc(-c5ccc6c7ccccc7n(-c7ccccc7)c6c5)ccc4n(-c4ccc5c(c4)c4ccccc4n5-c4nc(-c5ccccc5)nc(-c5ccccc5)n4)c3cc21]
34
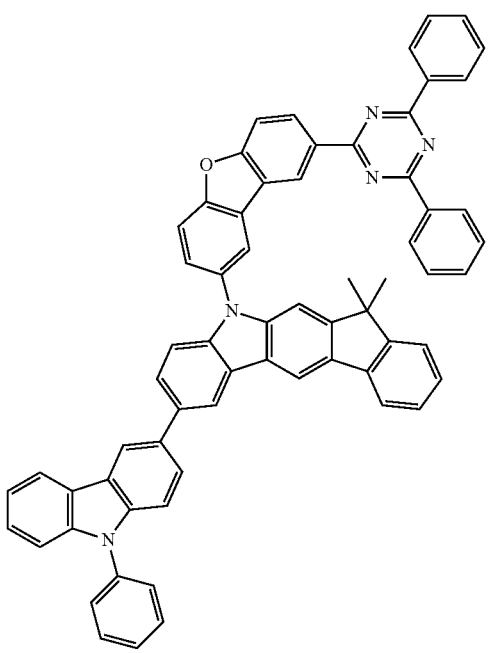
35

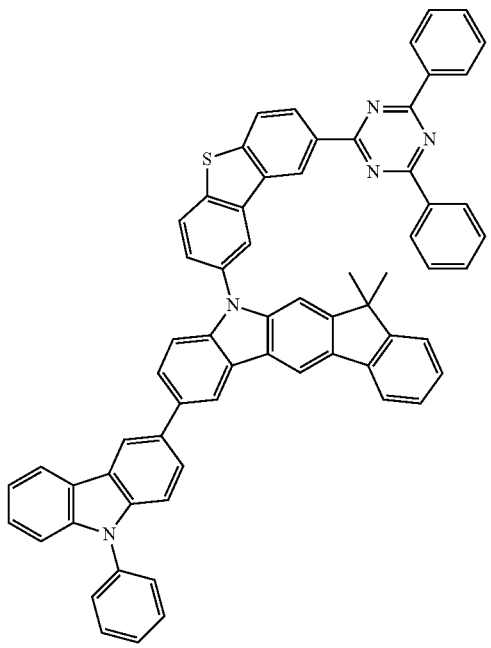 [SMILES: CC1(C)c2ccccc2-c2cc3c4cc(-c5ccc6c(c5)c5ccccc5n6-c5ccccc5)ccc4n(-c4ccc5sc6ccc(-c7nc(-c8ccccc8)nc(-c8ccccc8)n7)cc6c5c4)c3cc21]
36
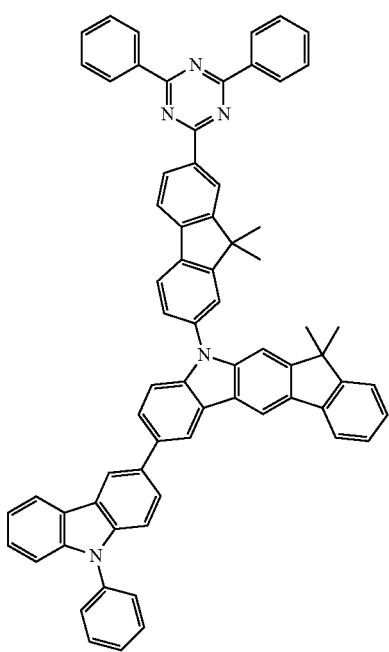 [SMILES: CC1(C)c2cc(-c3nc(-c4ccccc4)nc(-c4ccccc4)n3)ccc2-c2ccc(-n3c4ccc(-c5ccc6c(c5)c5ccccc5n6-c5ccccc5)cc4c4cc5c(cc43)C(C)(C)c3ccccc3-5)cc21]
37

-continued
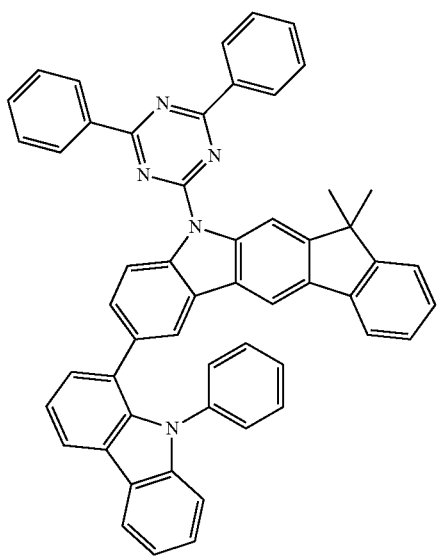 [SMILES: CC1(C)c2ccccc2-c2cc3c4cc(-c5cccc6c7ccccc7n(-c7ccccc7)c56)ccc4n(-c4nc(-c5ccccc5)nc(-c5ccccc5)n4)c3cc21]
38
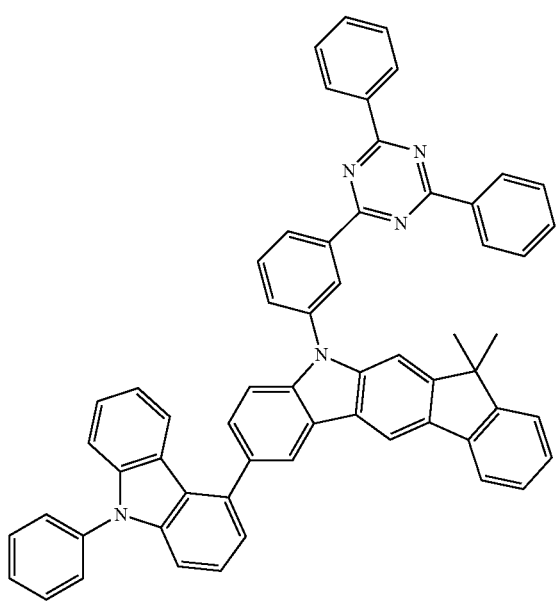
39
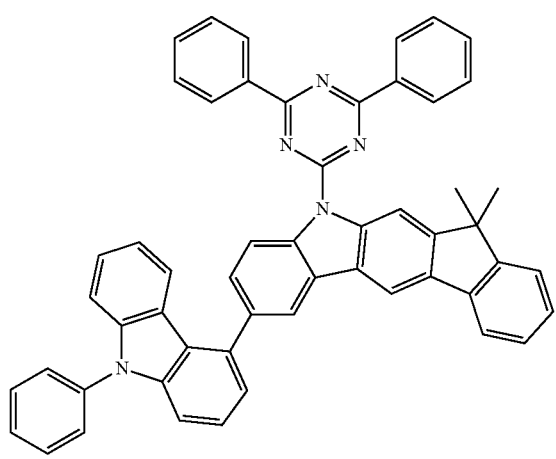 [SMILES: CC1(C)c2ccccc2-c2cc3c4cc(-c5cccc6c5c5ccccc5n6-c5ccccc5)ccc4n(-c4nc(-c5ccccc5)nc(-c5ccccc5)n4)c3cc21]
40

-continued
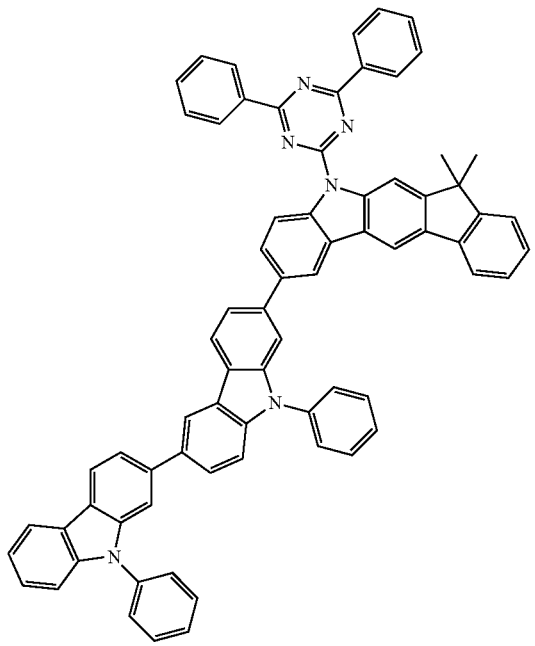 [SMILES: CC1(C)c2ccccc2-c2cc3c4cc(-c5ccc6c7cc(-c8ccc9c%10ccccc%10n(-c%10ccccc%10)c9c8)ccc7n(-c7ccccc7)c6c5)ccc4n(-c4nc(-c5ccccc5)nc(-c5ccccc5)n4)c3cc21]
41
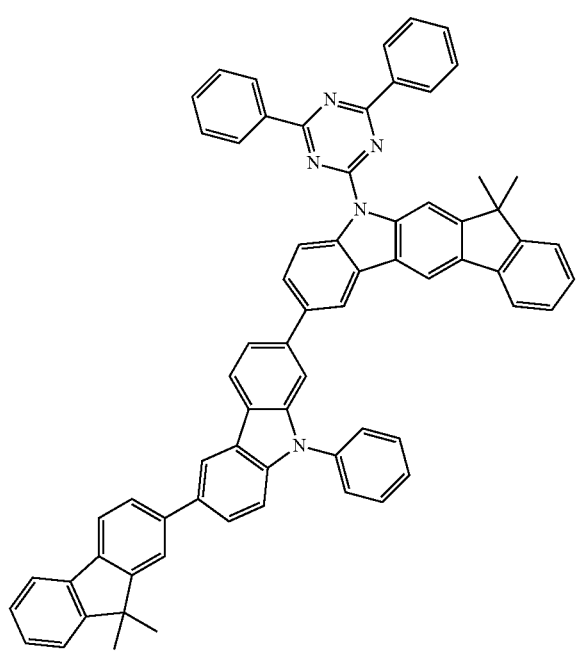 [SMILES: CC1(C)c2ccccc2-c2ccc(-c3ccc4c(c3)c3ccc(-c5ccc6c(c5)c5cc7c(cc5n6-c5nc(-c6ccccc6)nc(-c6ccccc6)n5)C(C)(C)c5ccccc5-7)cc3n4-c3ccccc3)cc21]
42

-continued
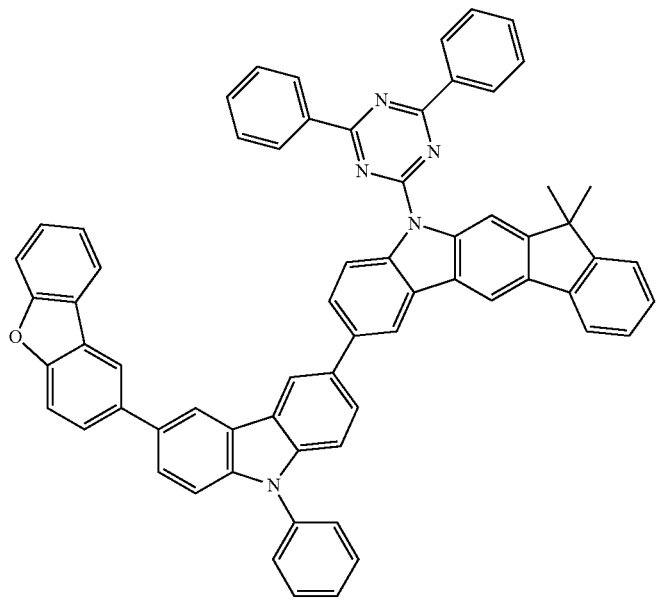 [SMILES: CC1(C)c2ccccc2-c2cc3c4cc(-c5ccc6c(c5)c5cc(-c7ccc8oc9ccccc9c8c7)ccc5n6-c5ccccc5)ccc4n(-c4nc(-c5ccccc5)nc(-c5ccccc5)n4)c3cc21]
43
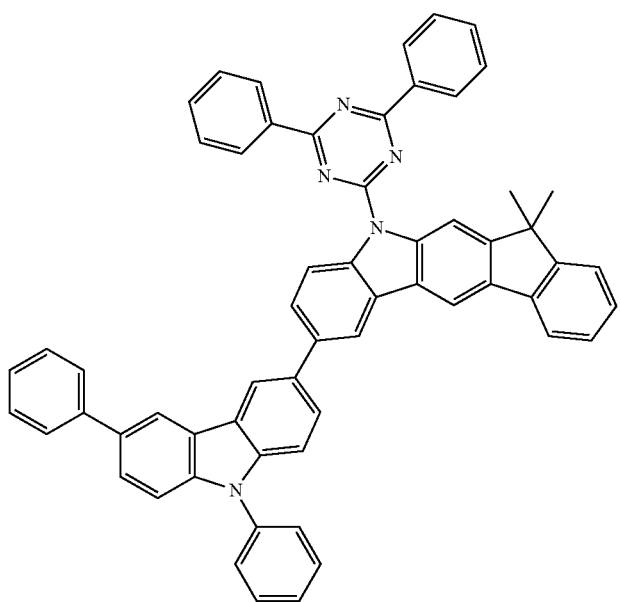 [SMILES: CC1(C)c2ccccc2-c2cc3c4cc(-c5ccc6c(c5)c5cc(-c7ccccc7)ccc5n6-c5ccccc5)ccc4n(-c4nc(-c5ccccc5)nc(-c5ccccc5)n4)c3cc21]
44

-continued
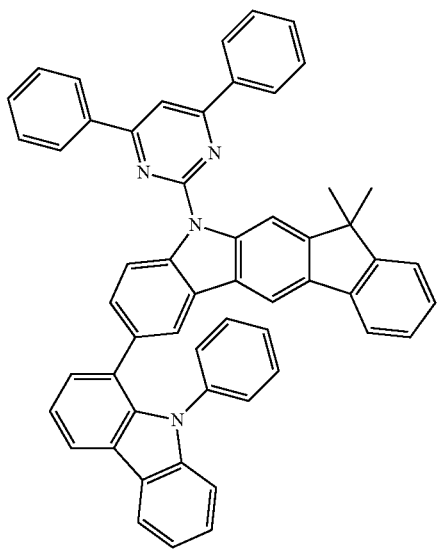 [SMILES: CC1(C)c2ccccc2-c2cc3c4cc(-c5cccc6c7ccccc7n(-c7ccccc7)c56)ccc4n(-c4nc(-c5ccccc5)cc(-c5ccccc5)n4)c3cc21]
45
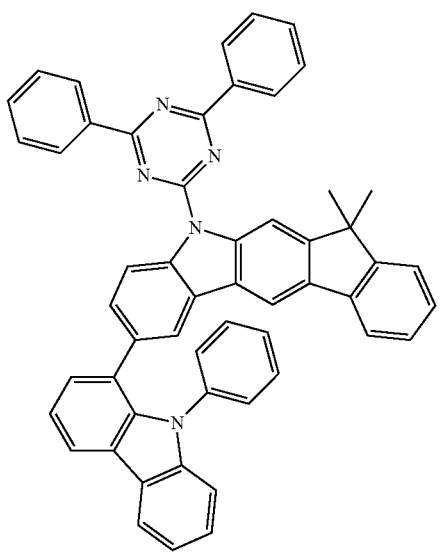
46

-continued
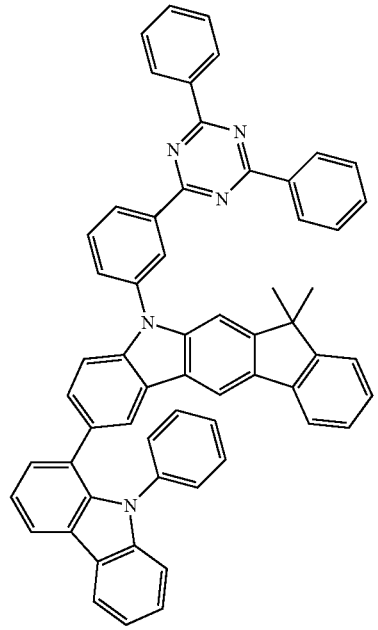 [SMILES: CC1(C)c2ccccc2-c2cc3c4cc(-c5cccc6c7ccccc7n(-c7ccccc7)c56)ccc4n(-c4cccc(-c5nc(-c6ccccc6)nc(-c6ccccc6)n5)c4)c3cc21]
47
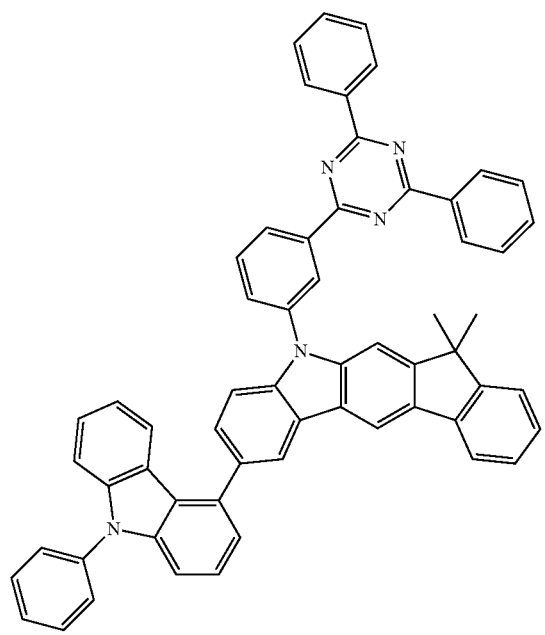 [SMILES: CC1(C)c2ccccc2-c2cc3c4cc(-c5cccc6c5c5ccccc5n6-c5ccccc5)ccc4n(-c4cccc(-c5nc(-c6ccccc6)nc(-c6ccccc6)n5)c4)c3cc21]
48

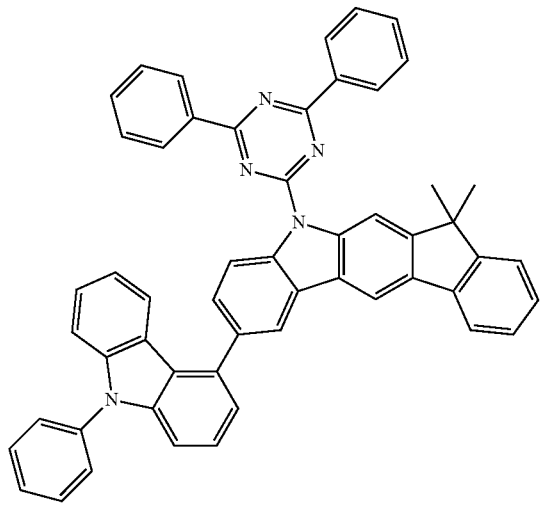 [SMILES: CC1(C)c2ccccc2-c2cc3c4cc(-c5cccc6c5c5ccccc5n6-c5ccccc5)ccc4n(-c4nc(-c5ccccc5)nc(-c5ccccc5)n4)c3cc21]
49
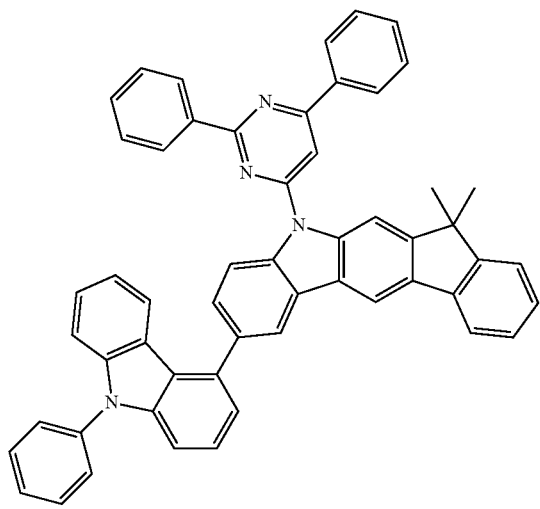 [SMILES: CC1(C)c2ccccc2-c2cc3c4cc(-c5cccc6c5c5ccccc5n6-c5ccccc5)ccc4n(-c4cc(-c5ccccc5)nc(-c5ccccc5)n4)c3cc21]
50
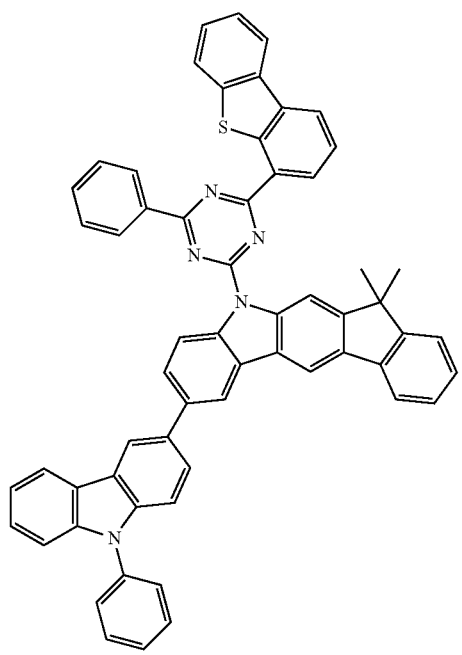 [SMILES: CC1(C)c2ccccc2-c2cc3c4cc(-c5ccc6c(c5)c5ccccc5n6-c5ccccc5)ccc4n(-c4nc(-c5ccccc5)nc(-c5cccc6c5sc5ccccc56)n4)c3cc21]
51

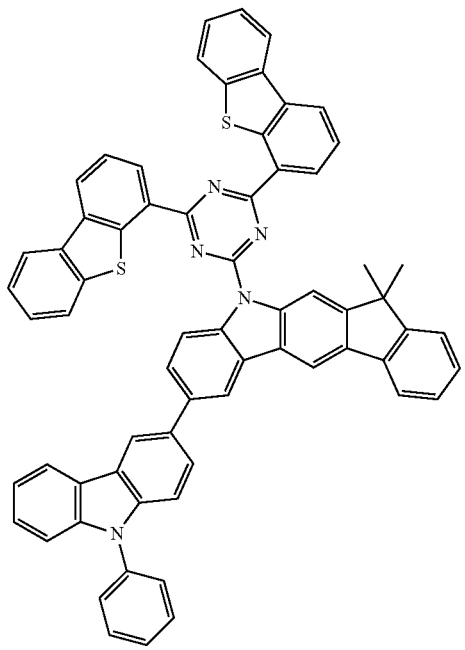 [SMILES: CC1(C)c2ccccc2-c2cc3c4cc(-c5ccc6c(c5)c5ccccc5n6-c5ccccc5)ccc4n(-c4nc(-c5cccc6c5sc5ccccc56)nc(-c5cccc6c5sc5ccccc56)n4)c3cc21]
52
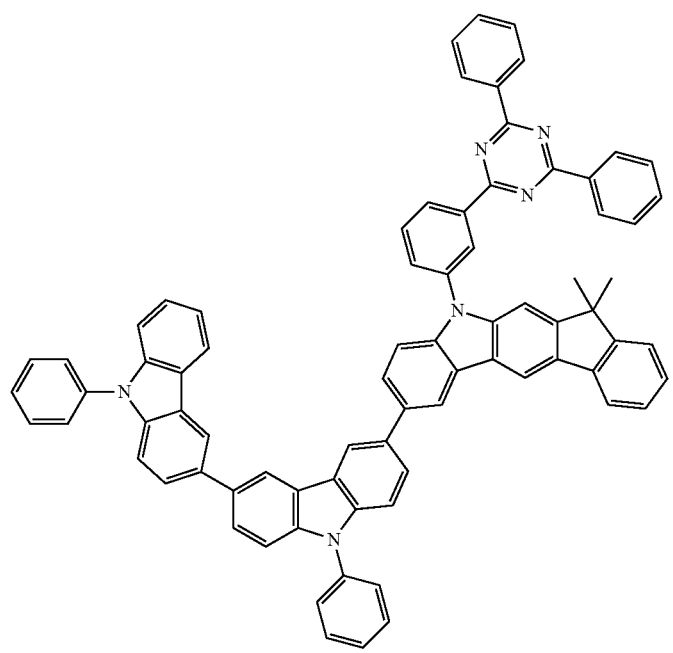 [SMILES: CC1(C)c2ccccc2-c2cc3c4cc(-c5ccc6c(c5)c5cc(-c7ccc8c(c7)c7ccccc7n8-c7ccccc7)ccc5n6-c5ccccc5)ccc4n(-c4cccc(-c5nc(-c6ccccc6)nc(-c6ccccc6)n5)c4)c3cc21]
53

-continued
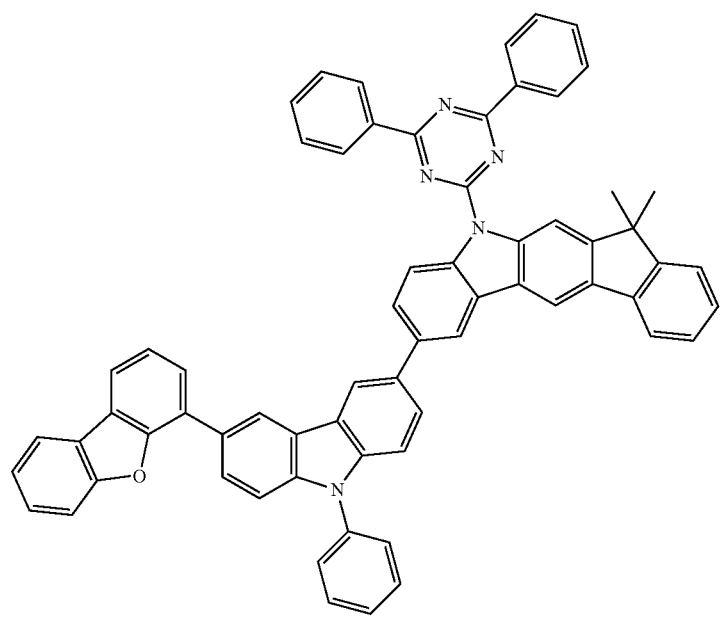 [SMILES: CC1(C)c2ccccc2-c2cc3c4cc(-c5ccc6c(c5)c5cc(-c7cccc8c7oc7ccccc78)ccc5n6-c5ccccc5)ccc4n(-c4nc(-c5ccccc5)nc(-c5ccccc5)n4)c3cc21]
54
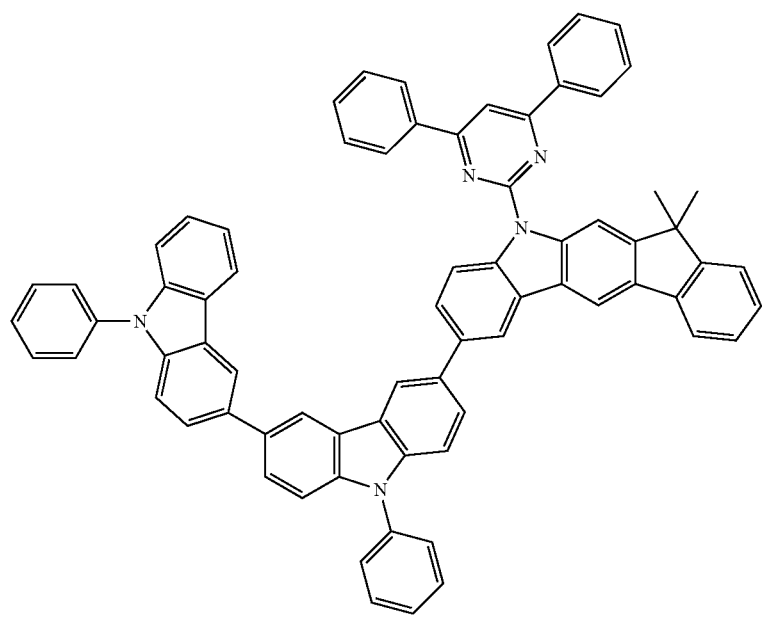 [SMILES: CC1(C)c2ccccc2-c2cc3c4cc(-c5ccc6c(c5)c5cc(-c7ccc8c(c7)c7ccccc7n8-c7ccccc7)ccc5n6-c5ccccc5)ccc4n(-c4nc(-c5ccccc5)cc(-c5ccccc5)n4)c3cc21]
55

-continued
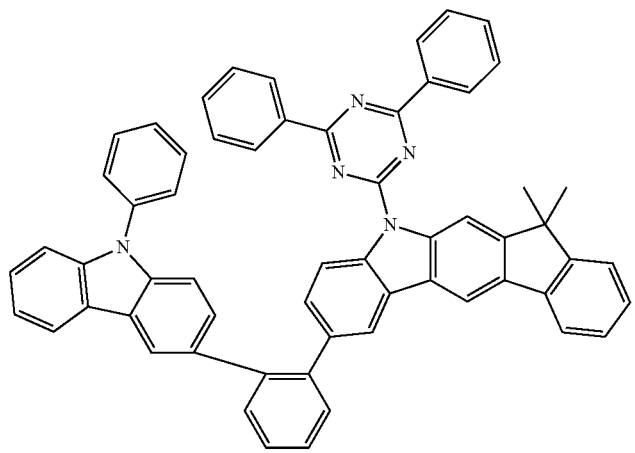 [SMILES: CC1(C)c2ccccc2-c2cc3c4cc(-c5ccccc5-c5ccc6c(c5)c5ccccc5n6-c5ccccc5)ccc4n(-c4nc(-c5ccccc5)nc(-c5ccccc5)n4)c3cc21]
56
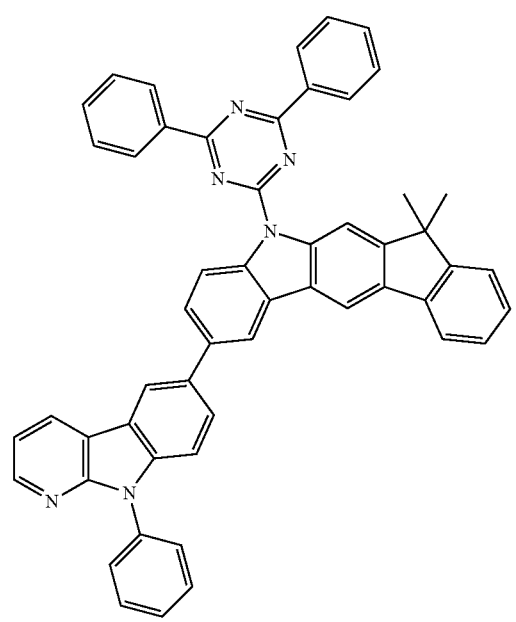 [SMILES: CC1(C)c2ccccc2-c2cc3c4cc(-c5ccc6c(c5)c5cccnc5n6-c5ccccc5)ccc4n(-c4nc(-c5ccccc5)nc(-c5ccccc5)n4)c3cc21]
57

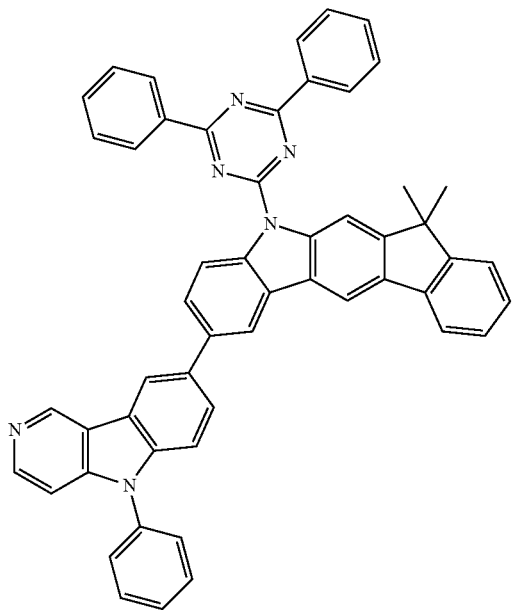 [SMILES: CC1(C)c2ccccc2-c2cc3c4cc(-c5ccc6c(c5)c5cnccc5n6-c5ccccc5)ccc4n(-c4nc(-c5ccccc5)nc(-c5ccccc5)n4)c3cc21]
58
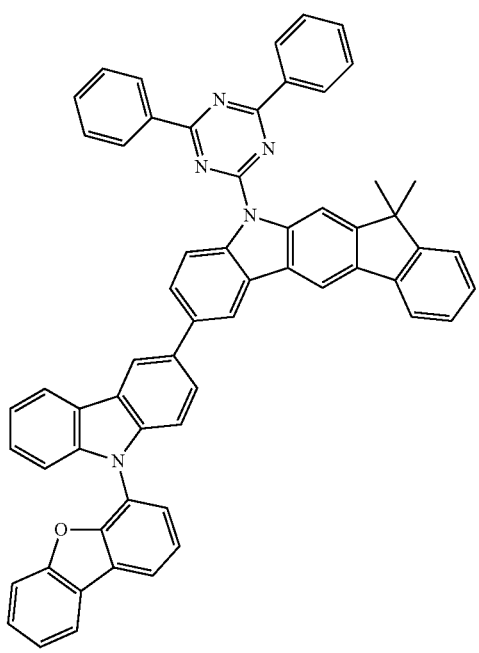 [SMILES: CC1(C)c2ccccc2-c2cc3c4cc(-c5ccc6c(c5)c5ccccc5n6-c5cccc6c5oc5ccccc56)ccc4n(-c4nc(-c5ccccc5)nc(-c5ccccc5)n4)c3cc21]
59

-continued
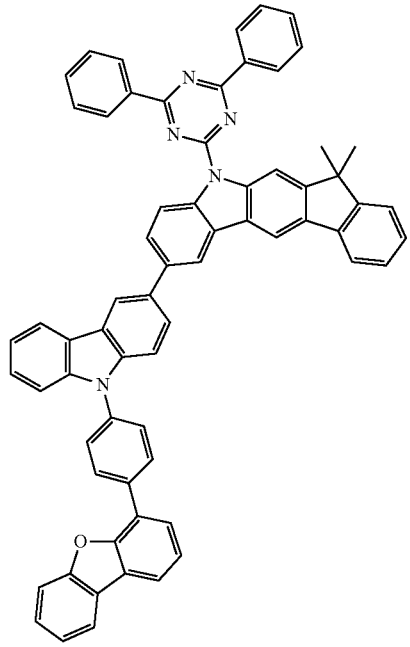 [SMILES: CC1(C)c2ccccc2-c2cc3c4cc(-c5ccc6c(c5)c5ccccc5n6-c5ccc(-c6cccc7c6oc6ccccc67)cc5)ccc4n(-c4nc(-c5ccccc5)nc(-c5ccccc5)n4)c3cc21]
60
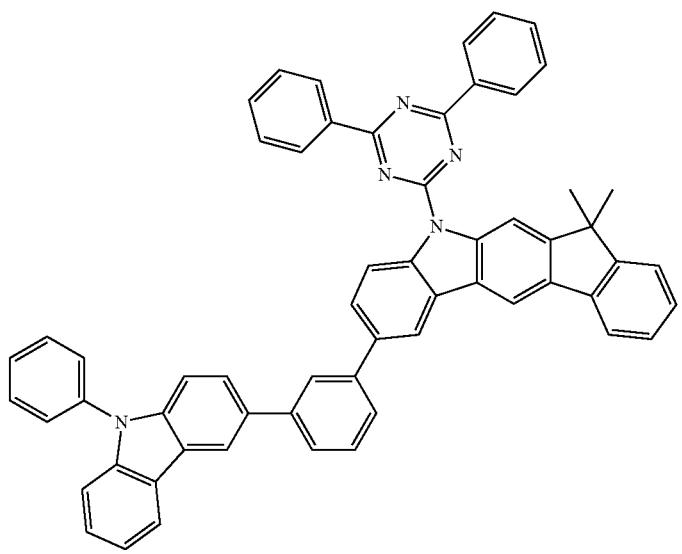 [SMILES: CC1(C)c2ccccc2-c2cc3c4cc(-c5cccc(-c6ccc7c(c6)c6ccccc6n7-c6ccccc6)c5)ccc4n(-c4nc(-c5ccccc5)nc(-c5ccccc5)n4)c3cc21]
61

-continued
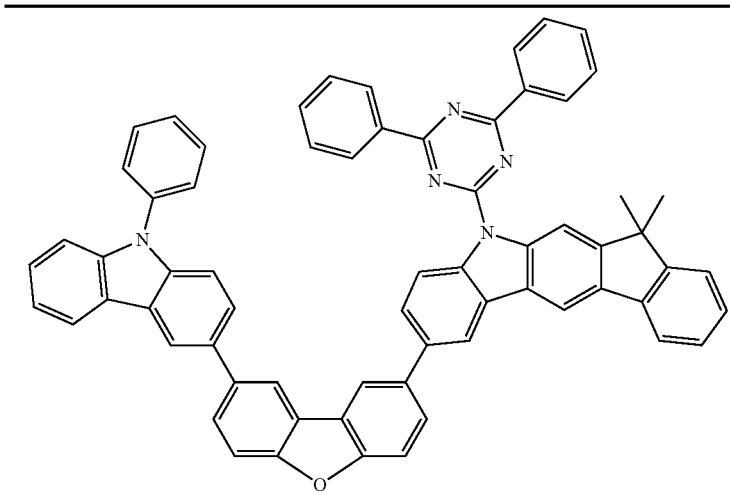
62
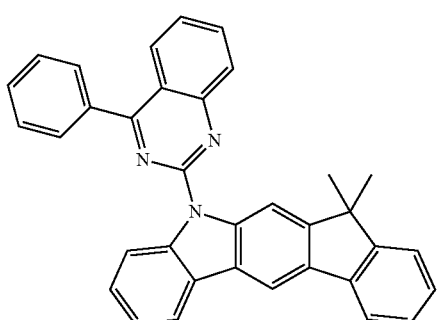
63
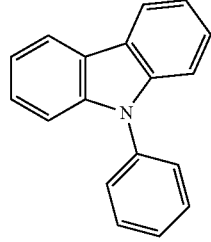
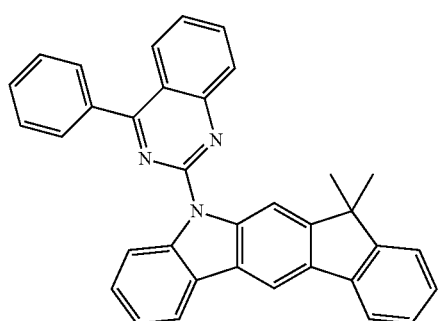
64
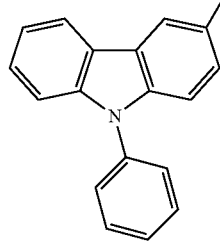

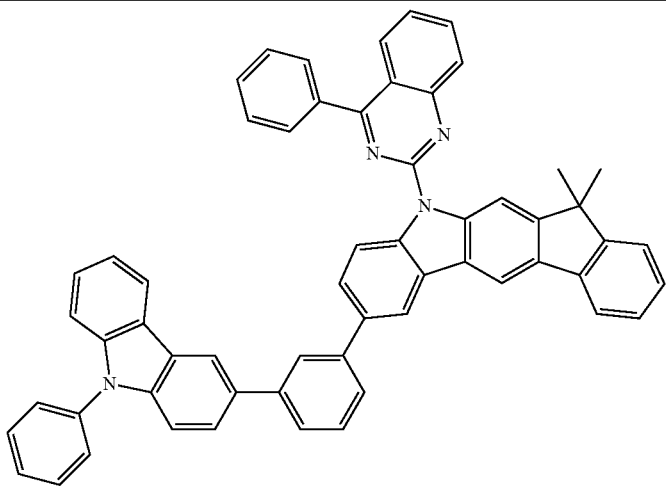

65

The compounds according to the invention can be prepared by means of known synthetic steps of organic chemistry. These include, for example, transition metal-catalysed coupling reactions, such as Suzuki and Buchwald coupling, brominations and halogenations.

Illustrative processes for the preparation of the compounds according to the invention are presented below. The processes shown are particularly suitable for the preparation of the compounds according to the invention. However, alternative processes are conceivable and possibly preferable in certain cases. Accordingly, the person skilled in the art will be able to modify the processes shown below within the scope of his general expert knowledge.

The compounds according to the invention are preferably synthesised as shown in Scheme 1. The compounds in Scheme 1 may be substituted at free positions by any desired organic radicals R.

An indenocarbazole compound is reacted in a first step here with a halo-genated aryl compound containing an electron-deficient heteroaryl group. The way in which indenocarbazole compounds of this type can be prepared is known from the prior art and is illustrated by the working examples in this application. The first step is preferably carried out under the conditions of a Buchwald coupling. A halogenation on the indenocarbazole skeleton is subsequently carried out. This is preferably a bromination, particularly preferably using the reagent NBS.

This step may be followed by a Suzuki coupling to a carbazole derivative which carries a boronic acid substituent. Alternatively, the halogenated product from the second step may itself be converted into a boronic acid and then reacted with a halogenated carbazole derivative in a Suzuki coupling.

The product obtained may already represent the target compound and conforms to formula (I). However, further steps may follow, for example in order to introduce further functional groups or radicals.

Scheme 1

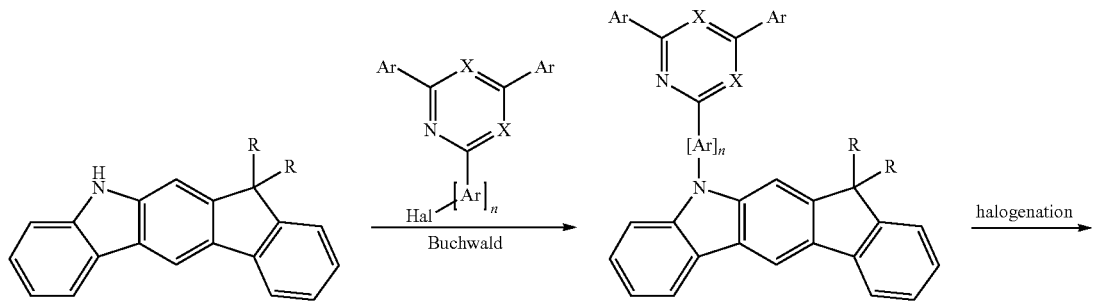

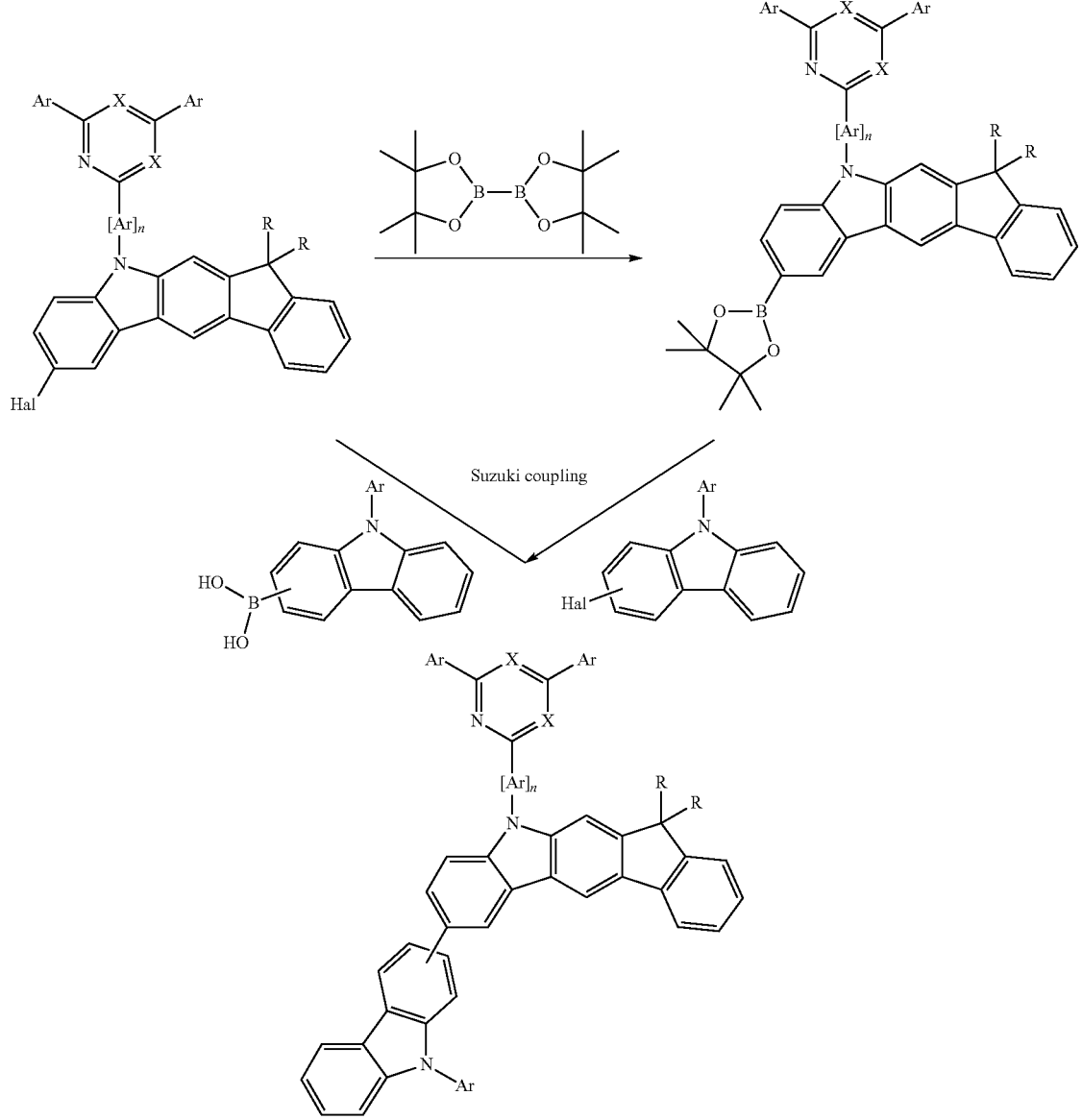

n = 0 or 1
X = N or CR
Hal = halogen
R = organic radical
Ar = aromatic or heteroaromatic ring system The invention thus furthermore relates to a process for the preparation of a compound of the formula (I), characterised in that an indenocarbazole compound is reacted with an aromatic or heteroaromatic ring system which contains an electron-deficient heteroaryl group, where the aromatic or heteroaromatic ring system is coupled to the nitrogen atom of the indenocarbazole. The reaction is preferably a Buchwald coupling between an indenocarbazole and a halogenated aromatic or heteroaromatic ring system.

Furthermore, the reaction product is preferably subsequently provided with a reactive functional group, for example by halogenation or by conversion into a boronic acid. Furthermore, a Suzuki coupling to a carbazole derivative is preferably subsequently carried out.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (I), where the bond(s) to the polymer, oligomer or dendrimer may be localised at any desired positions in formula (I) which are substituted by $R^1$ or $R^2$.

Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), paraphenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THE, THP, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecyl-benzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compound of the formula (I) is suitable for use in an electronic device, in particular an organic electroluminescent device (OLED). Depending on the substitution, the compound of the formula (I) can be employed in different functions and layers. Preference is given to the use as matrix material in an emitting layer, particularly preferably in combination with a phosphorescent emitter, and/or the use as electron-transporting material, and/or the use as hole-blocking material.

The invention therefore furthermore relates to the use of a compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I). The electronic device here is preferably selected from the devices mentioned above.

Particular preference is given to an organic electroluminescent device comprising anode, cathode and at least one emitting layer, characterised in that the device comprises at least one organic layer which comprises at least one compound of the formula (I). Preference is given to an organic electroluminescent device comprising anode, cathode and at least one emitting layer, characterised in that at least one layer in the device, selected from emitting layers, electron-transport layers, electron-injection layers and hole-blocking layers, comprises at least one compound of the formula (I).

An electron-transport layer is taken to mean any desired organic layer, arranged between cathode and an emitting layer, which has electron-transporting properties.

An electron-injection layer is taken to mean any desired organic layer, arranged between cathode and an emitting layer, which has electron-injecting properties and is directly adjacent to the cathode.

A hole-blocking layer is taken to mean any desired organic layer which is located between emitting layer and cathode and has hole-blocking properties. A hole-blocking layer in accordance with the present application is preferably located between an emitting layer and an electron-transporting layer, particularly preferably directly adjacent to an emitting layer on the cathode side. Materials of the hole-blocking layer are typically distinguished by a low HOMO.

Apart from cathode, anode and emitting layer, the electronic device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N, Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the electronic device is preferably as follows:
 anode
 hole-injection layer
 hole-transport layer
 optionally further hole-transport layers
 emitting layer
 electron-transport layer
 electron-injection layer
 cathode.

It should again be pointed out here that not all the said layers have to be present, and/or that further layers may additionally be present.

The electronic device according to the invention may comprise a plurality of emitting layers. In this case, these emitting layers particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). The compounds according to the invention may alternatively and/or additionally also be present in the electron-transport layer or in another layer. It should be noted that, for the generation of white light, an emitter compound used individually which emits in a broad wavelength range may also be suitable instead of a plurality of emitter compounds emitting in colour.

The compound of the formula (I) is preferably present in the electronic device as matrix material in an emitting layer, particularly preferably in combination with one or more phosphorescent emitter compounds. The emitter compounds are preferably in the form of dopants.

The terms dopant, matrix material and phosphorescent emitter compound here are defined as described above.

Emitter compounds preferably used as matrix material in combination with the compound of the formula (I) are the phosphorescent emitter compounds indicated below.

The emitting layer of the electronic device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compound of the formula (I) is used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used in combination with the compounds according to the invention as matrix components of a mixed-matrix system are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the table above.

The proportion of the matrix material in the emitting layer in the electronic device according to the invention is preferably between 50.0 and 99.9% by vol., particularly preferably between 80.0 and 99.5% by vol. and very particularly preferably between 92.0 and 99.5% by vol. for fluorescent emitting layers and between 85.0 and 97.0% by vol. for phosphorescent emitting layers. Correspondingly, the proportion of the dopant is preferably between 0.1 and 50.0% by vol., particularly preferably between 0.5 and 20.0% by vol. and very particularly preferably between 0.5 and 8.0% by vol. for fluorescent emitting layers and between 3.0 and 15.0% by vol. for phosphorescent emitting layers.

In a further preferred embodiment of the invention, the compound of the formula (I) is employed as electron-transport material in an electron-transport layer or electron-injection layer or hole-blocking layer.

Materials which are preferably present in the above-mentioned functional layers of the electronic device according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of phosphorescent emitters are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

The compounds shown in the following table are particularly suitable phosphorescent dopants:

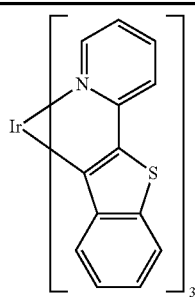

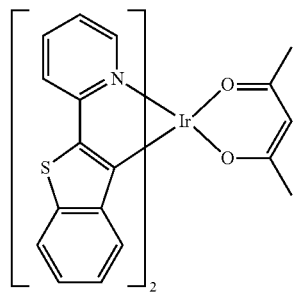

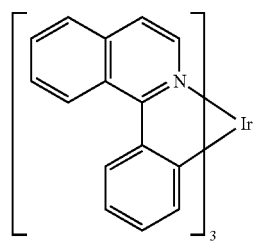

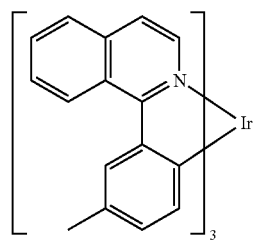

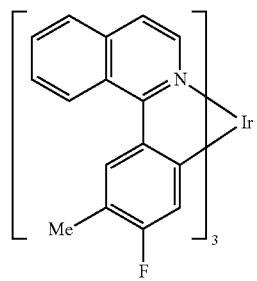

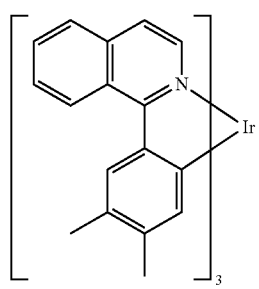

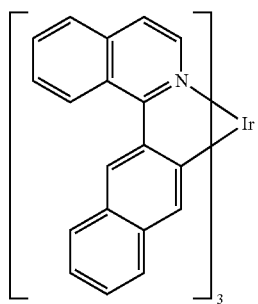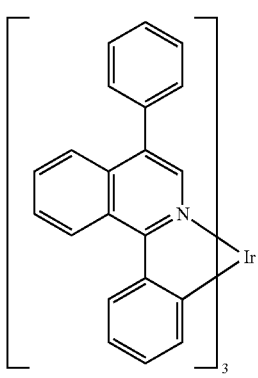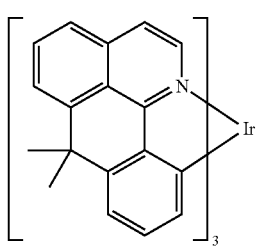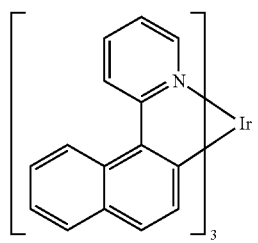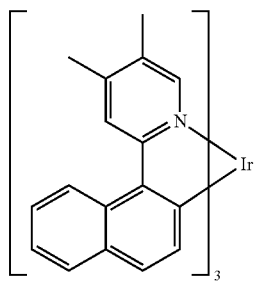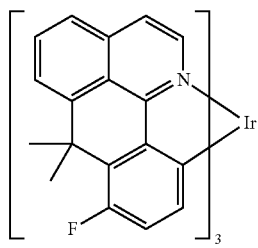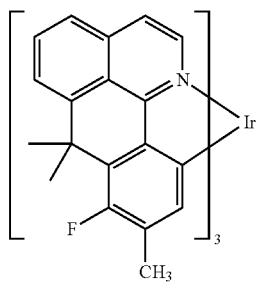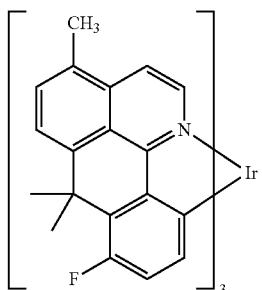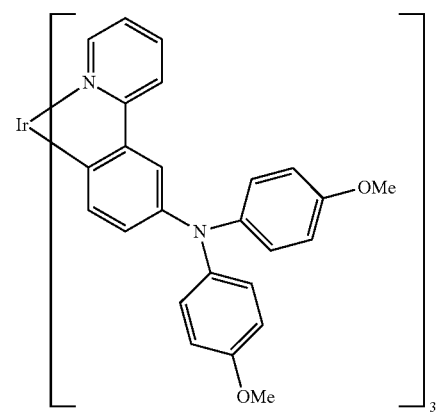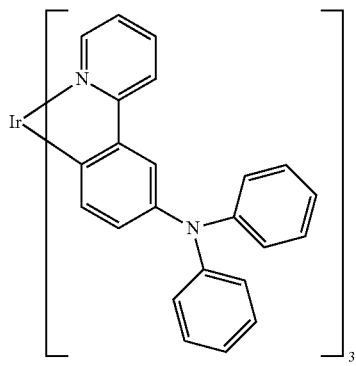

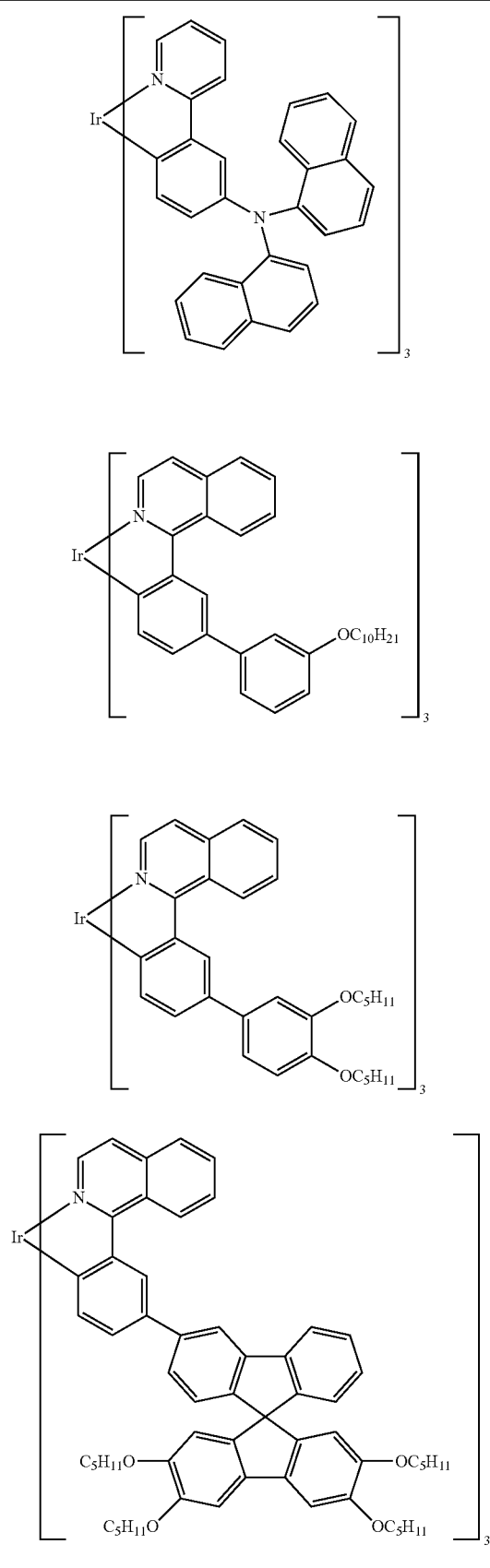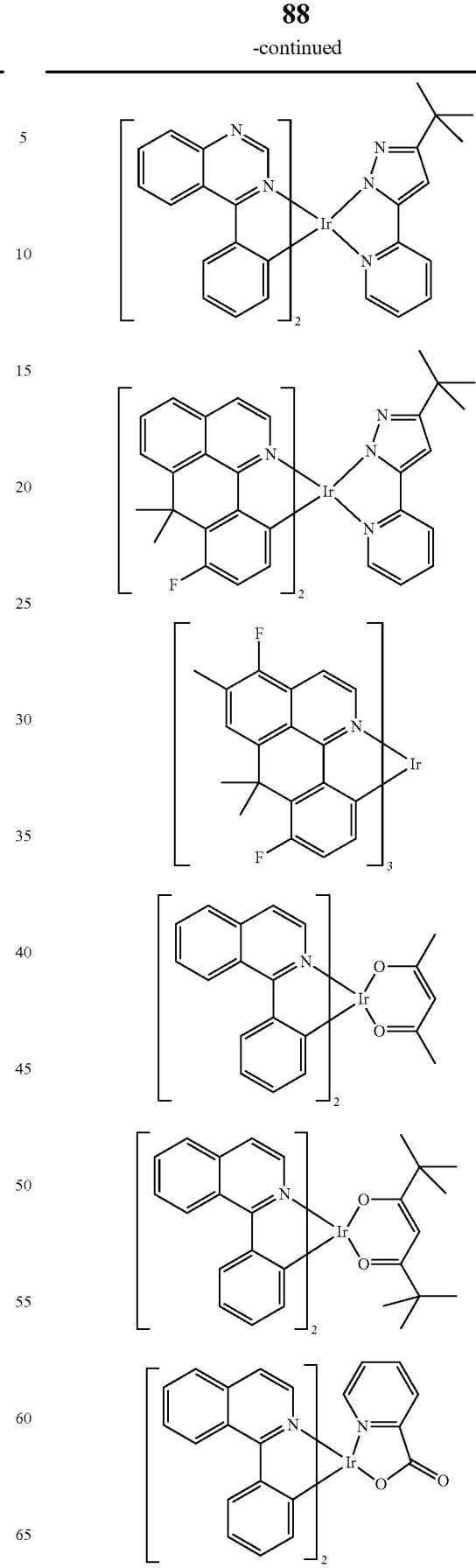

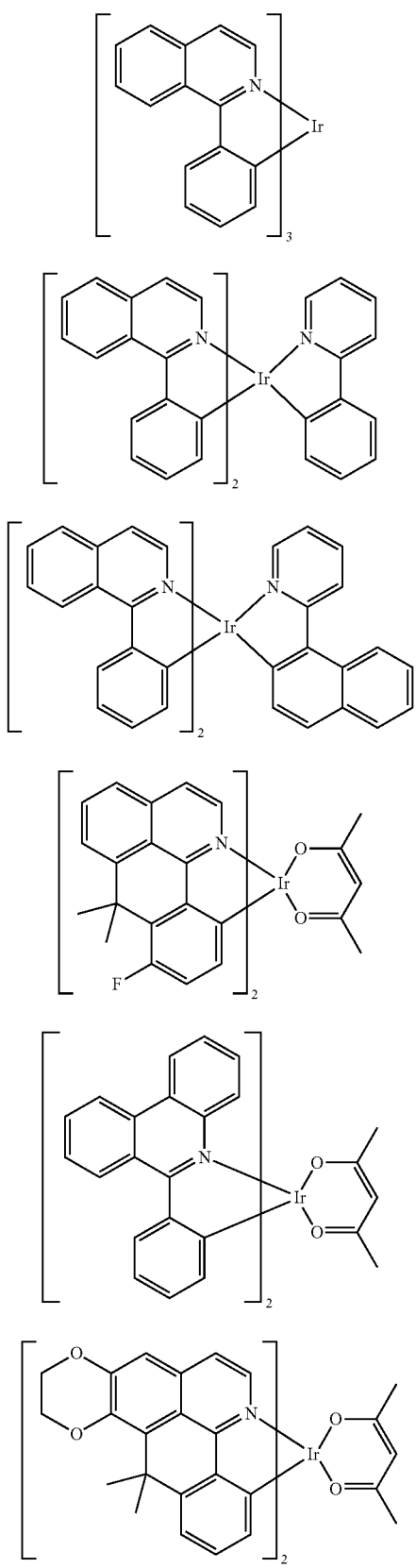

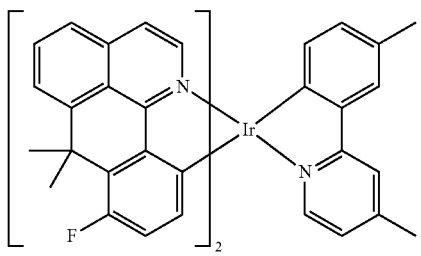
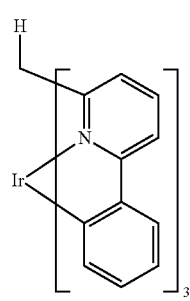
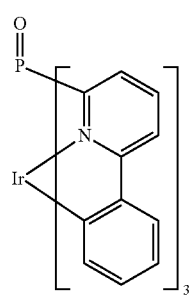
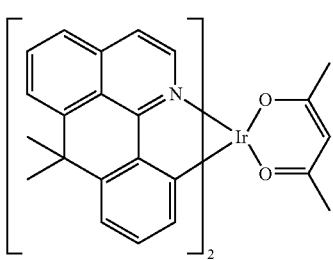
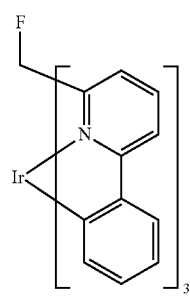
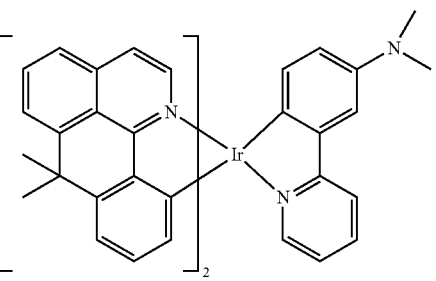
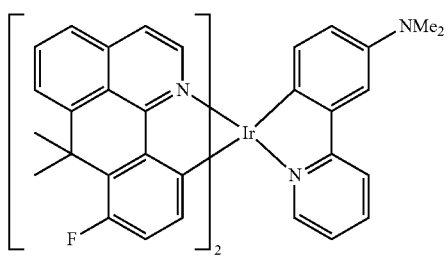
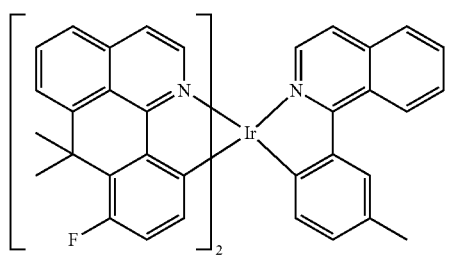
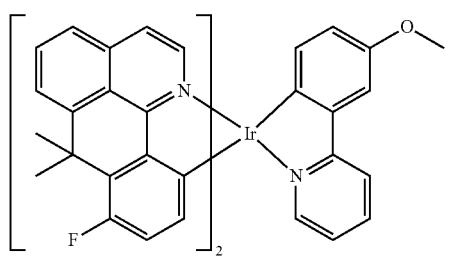
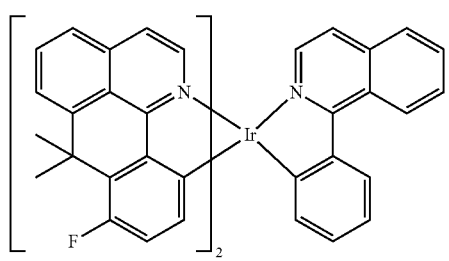
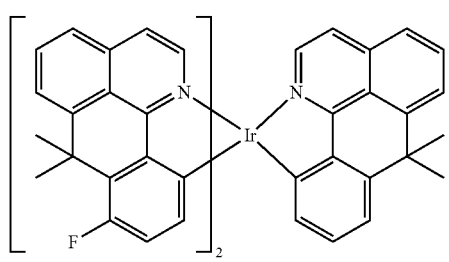

93
-continued
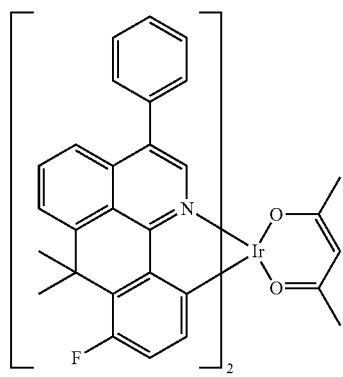
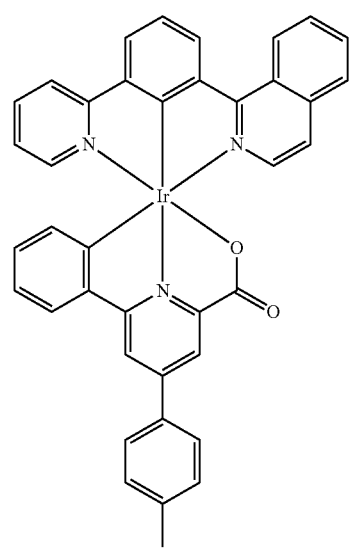
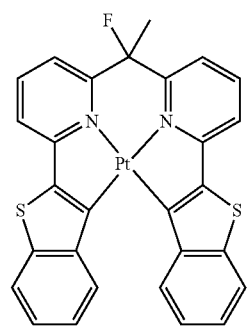
94
-continued
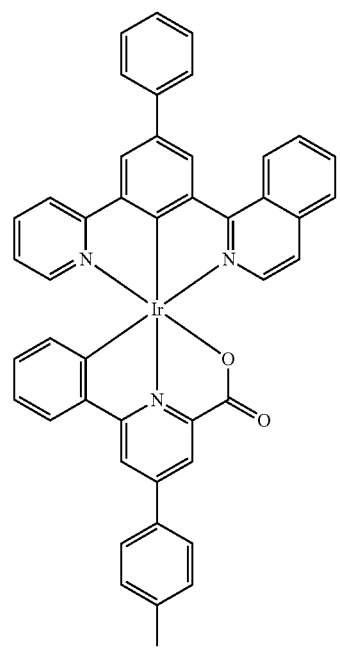
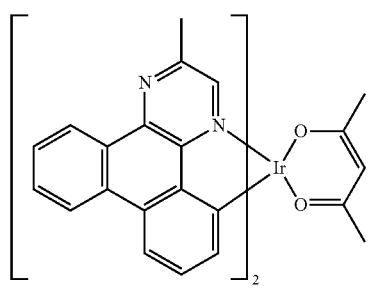
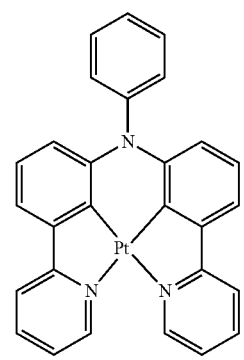
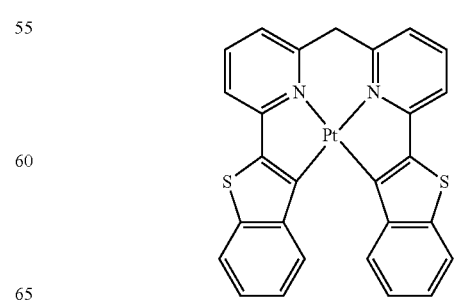

| 95 -continued | 96 -continued |
|---|---|
| 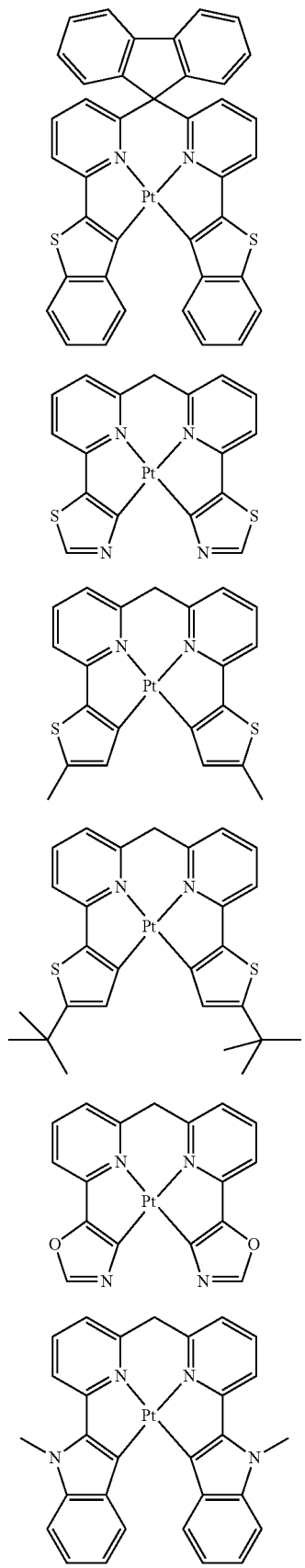 | 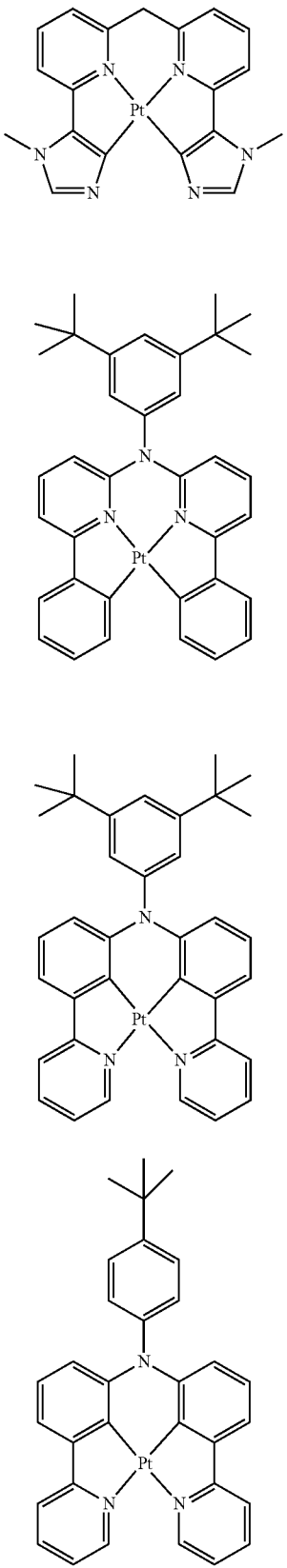 |

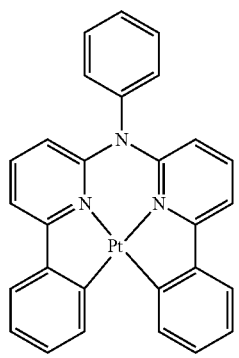
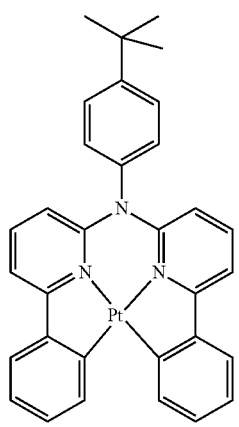
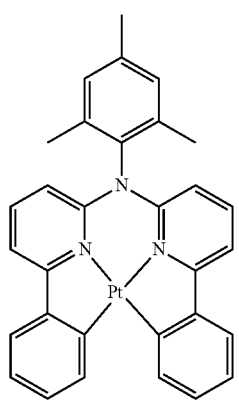
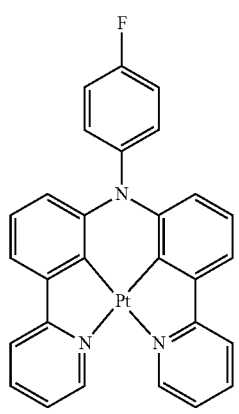
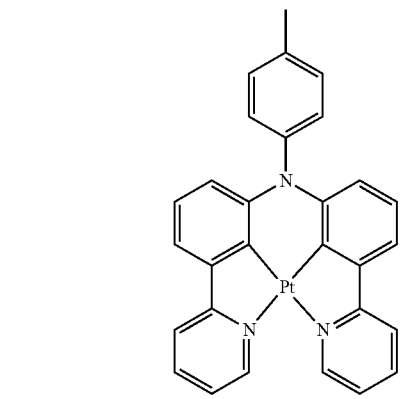
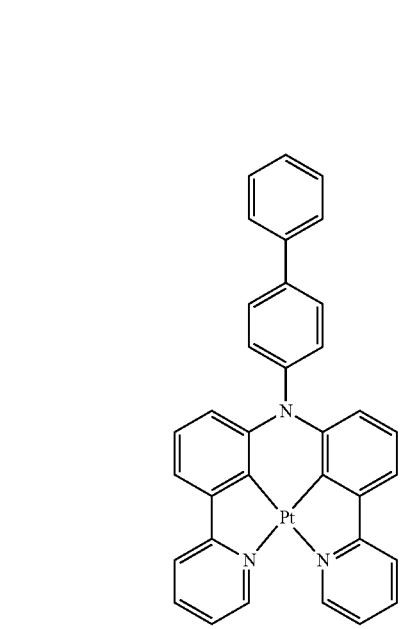
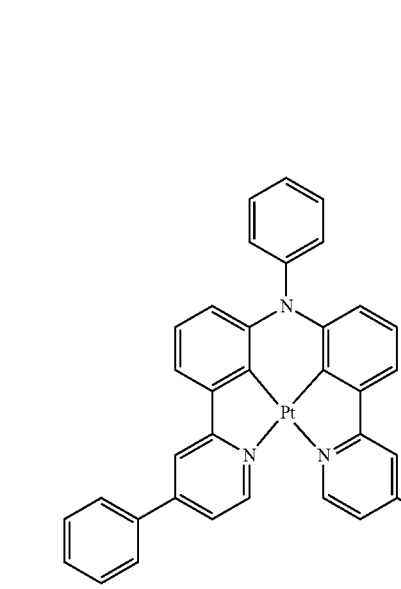

| 99 -continued | 100 -continued |
|---|---|
| 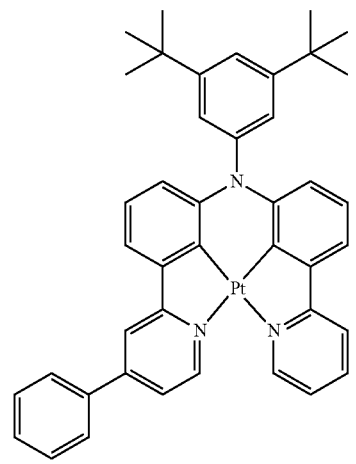 | 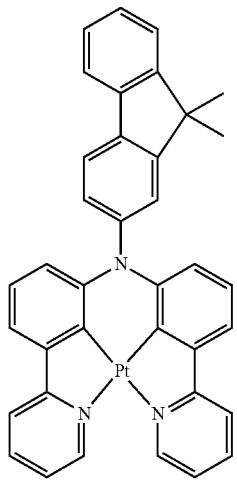 |
| 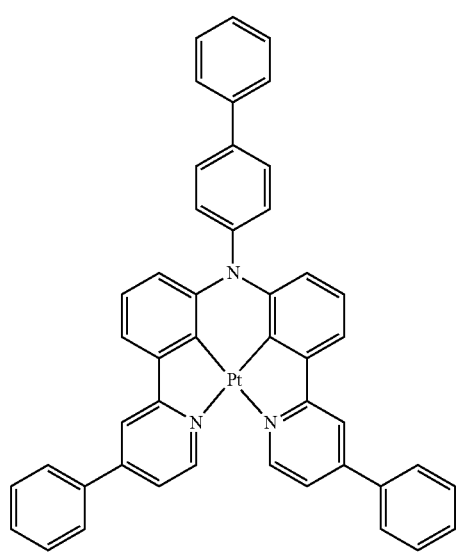 | 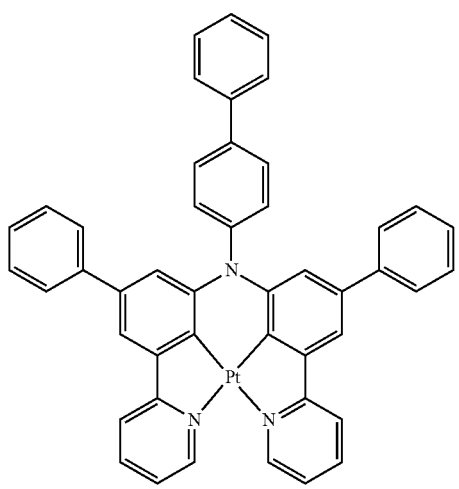 |
| 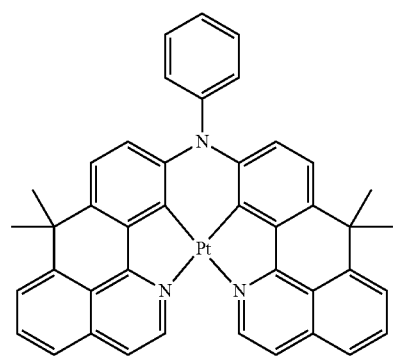 | 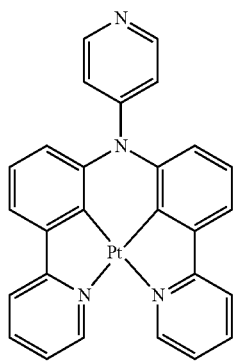 |

101
-continued
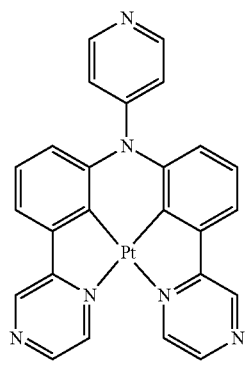
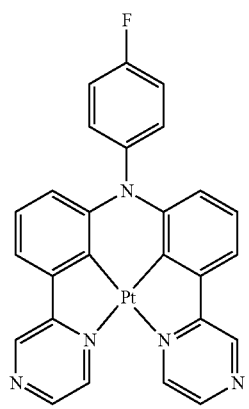
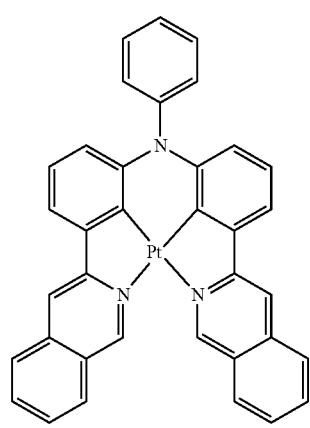
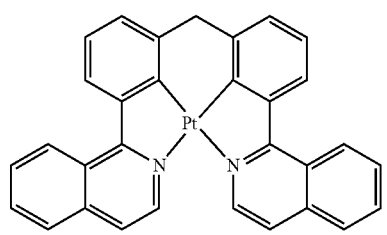
102
-continued
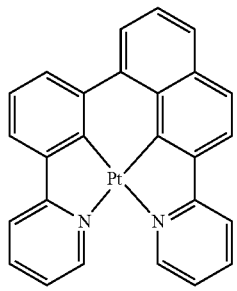
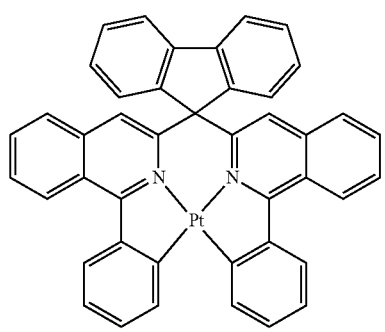
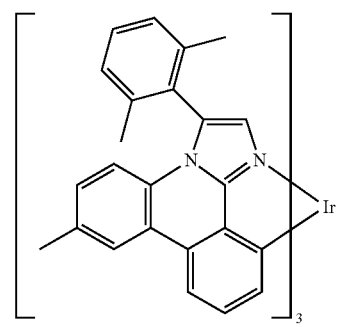
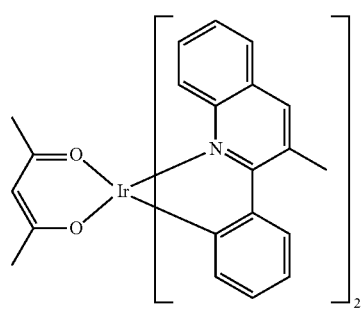
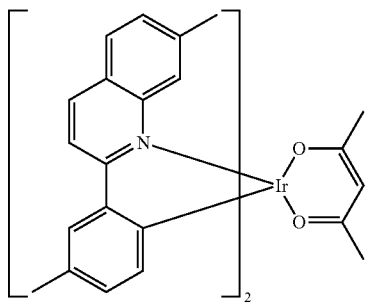

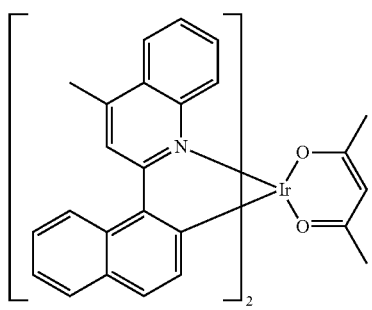
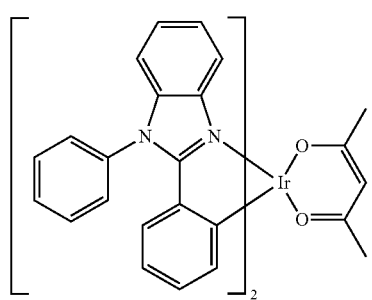
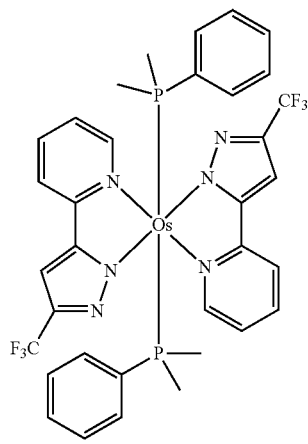
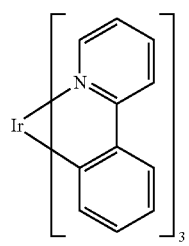
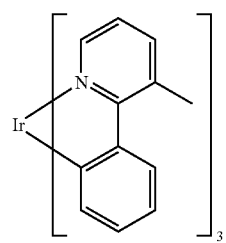
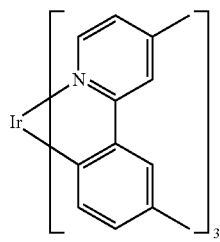
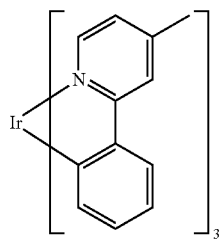
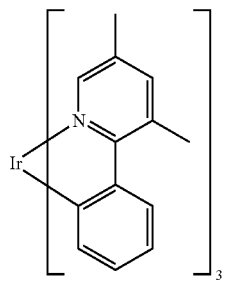
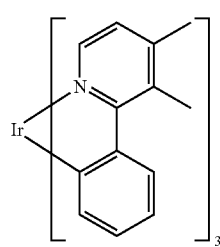
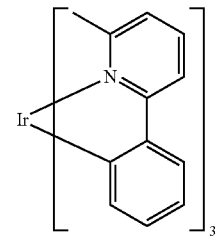
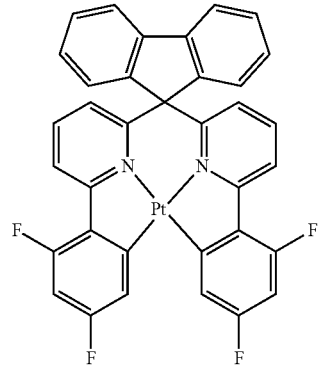

105
-continued
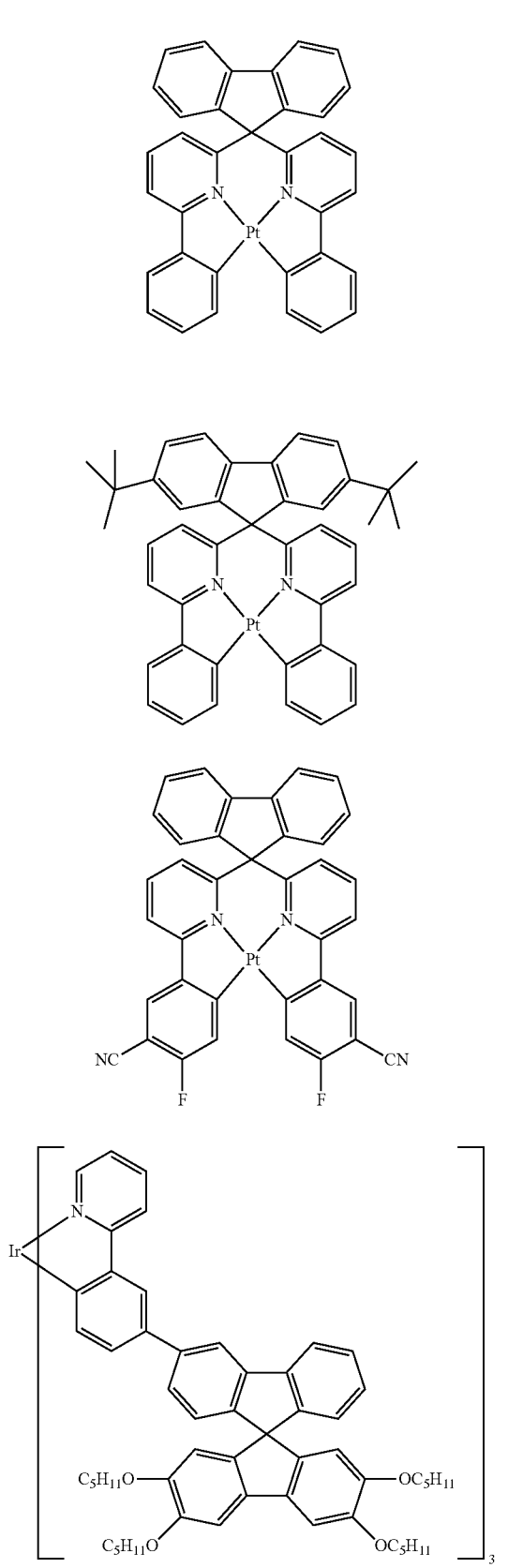
106
-continued
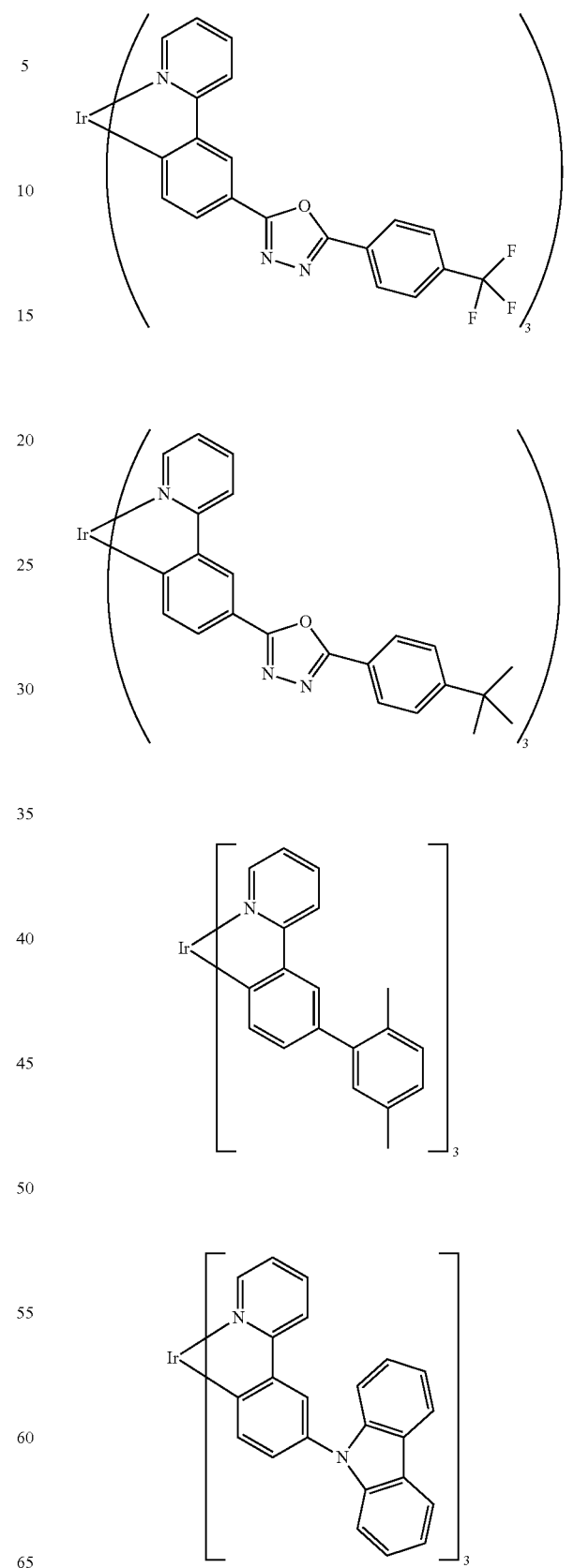

107
-continued
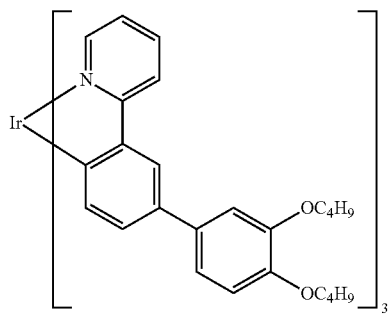
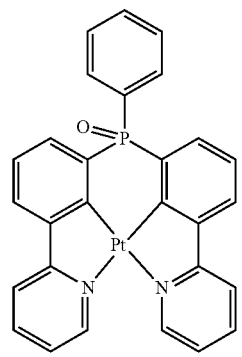
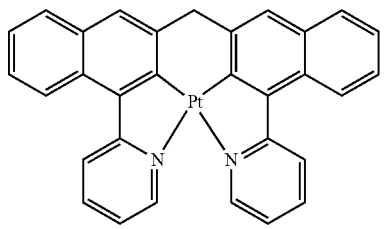
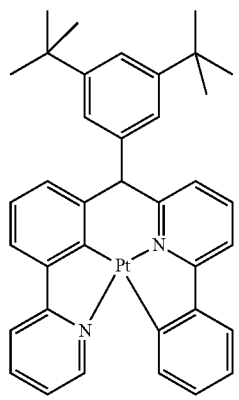
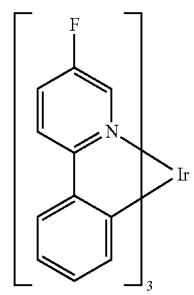
108
-continued
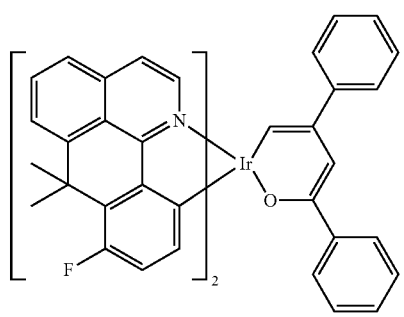
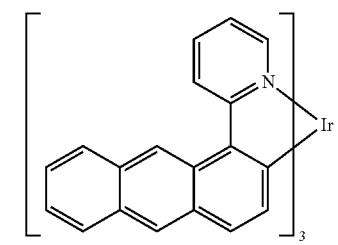
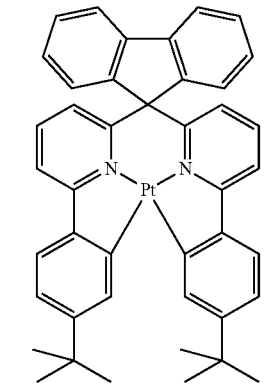
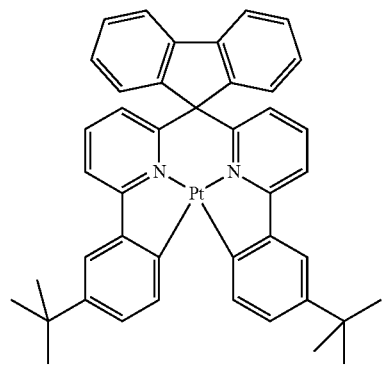

109
-continued
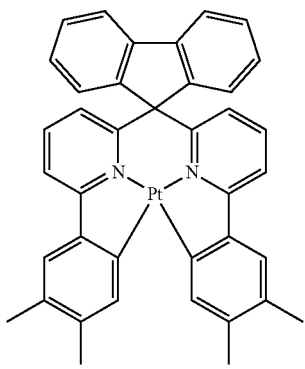
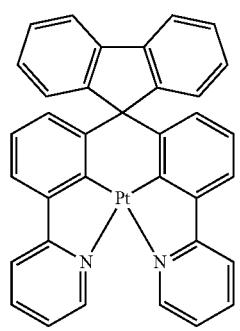
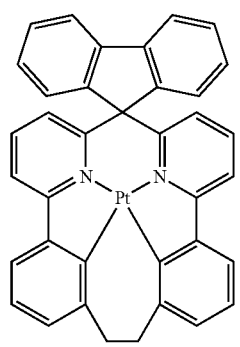
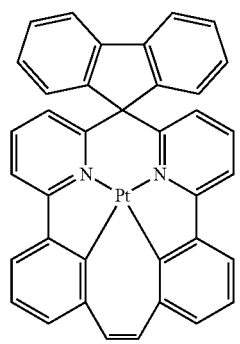
110
-continued
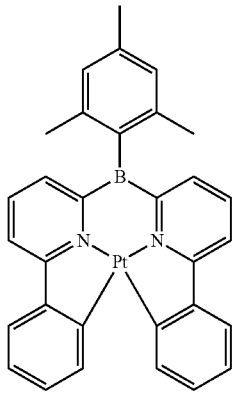
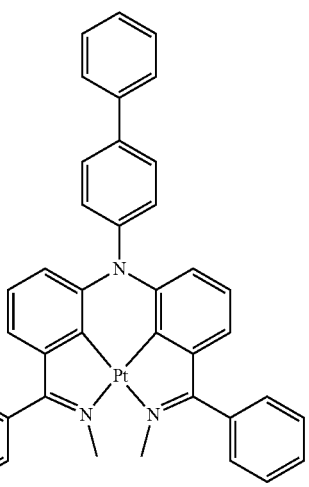
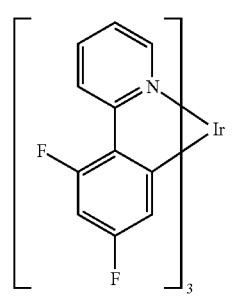

111
-continued
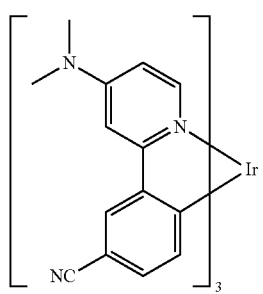
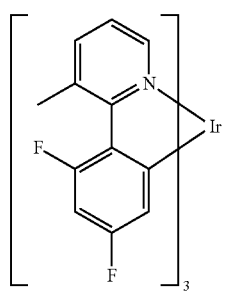
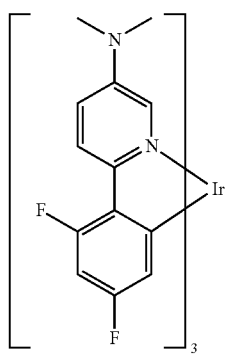
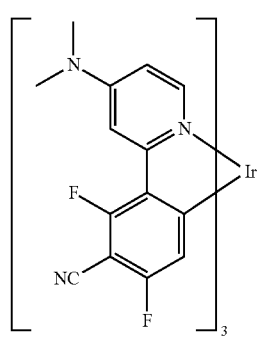
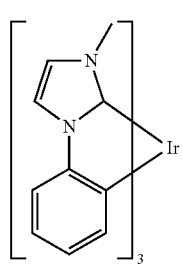
112
-continued
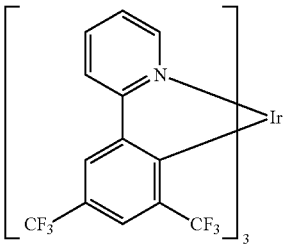
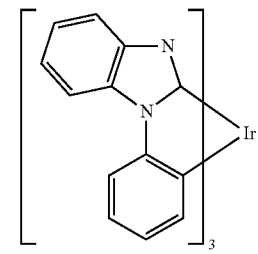
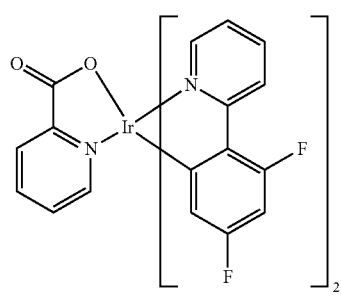
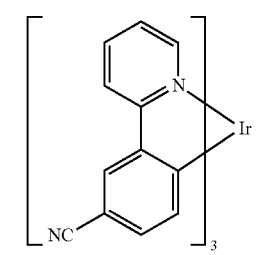
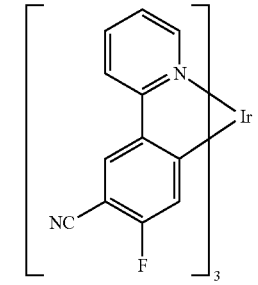
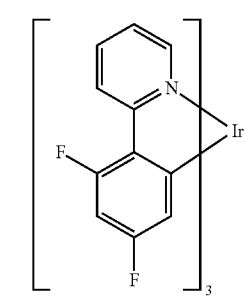

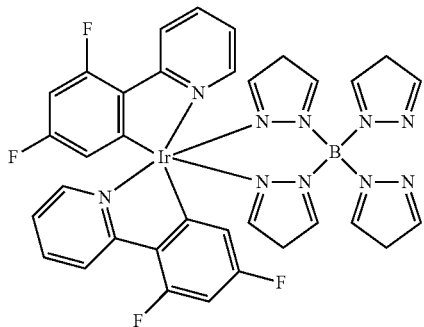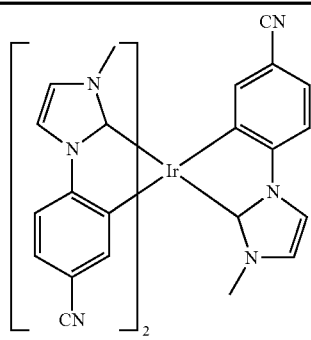
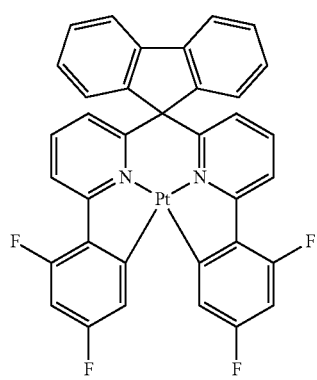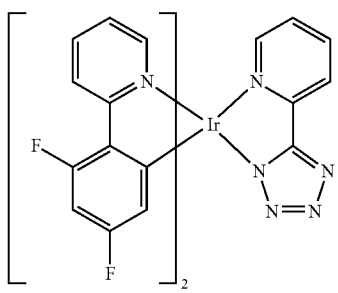
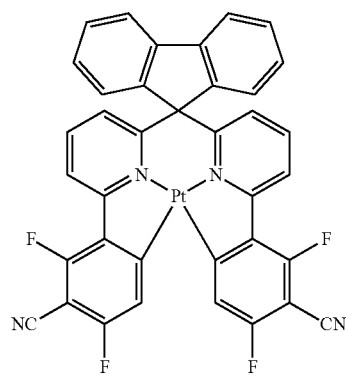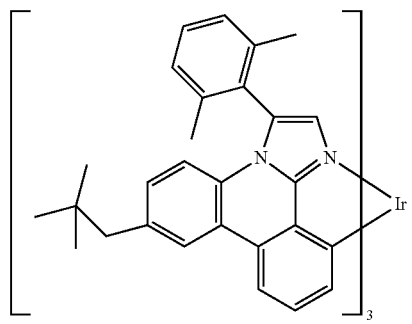
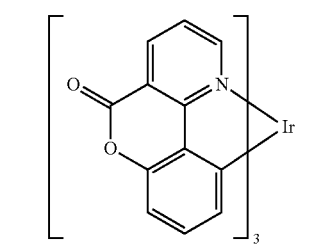
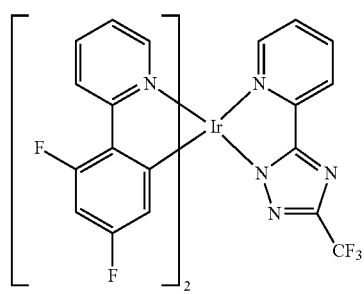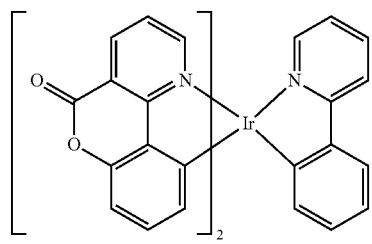

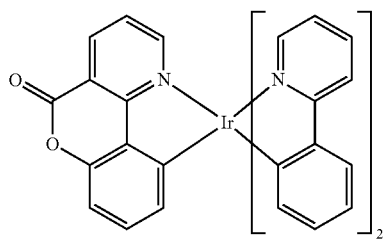

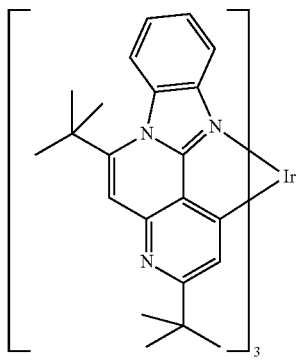

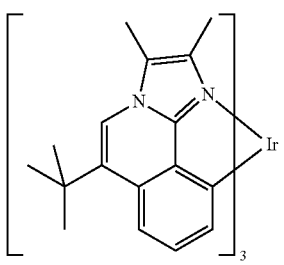

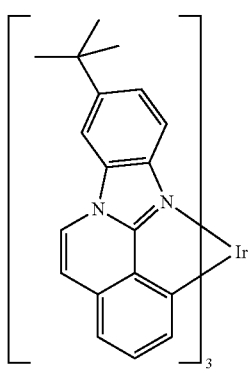

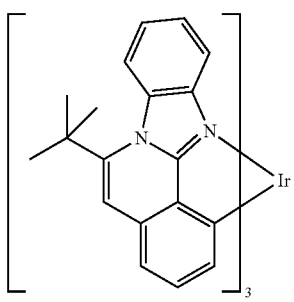

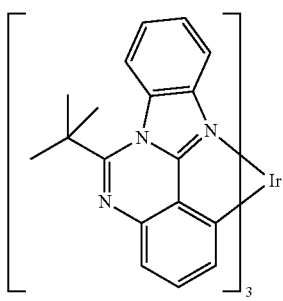

Preferred fluorescent emitters are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter compounds are indenofluorenamines or indenofluorenediamines, for example in accordance with WO 2006/108497 or WO 2006/122630, benzoindenofluorenamines or benzoindenofluorene-diamines, for example in accordance with WO 2008/006449, and dibenzo-indenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and the as yet unpublished EP 12004426.8. Preference is likewise given to the benzoindenofluorenamines disclosed in the as yet unpublished EP 12006239.3.

Suitable matrix materials, preferably for fluorescent emitters, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitters, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Suitable charge-transport materials, as can be used in the hole-injection or hole-transport layer or in the electron-transport layer of the organic electro-luminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer, besides the compounds according to the invention, are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, provided with contacts and finally sealed, since the lifetime of the devices according to the invention is shortened in the presence of water and/or air.

In a preferred embodiment, the electronic device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an electronic device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an electronic device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an electronic device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

The following working examples serve to explain the invention. They are not intended to be interpreted as restrictive.
A) Synthesis of the Compounds According to the Invention The following syntheses are carried out, unless indicated otherwise, in dried solvents under a protective-gas atmosphere. The compounds according to the invention can be prepared by means of synthetic methods known to the person skilled in the art.

I) Syntheses of Precursors

Example 1

2-Chloro-4,6-diphenylpyrimidine

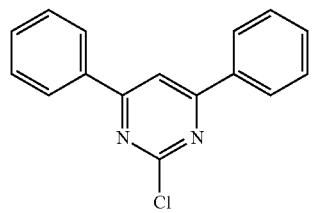 [SMILES: Clc1nc(-c2ccccc2)cc(-c2ccccc2)n1]

75 g (0.41 mmol) of 1,3,5-trichloropyrimidine, 100 g (0.82 mol) of phenyl-boronic acid and 625 ml of 4M NaHCO$_3$ solution are suspended in 2.5 l of ethylene glycol dimethyl ether. 2.3 g (10.23 mmol) of Pd(OAc)$_2$ and 10.35 g (34 mmol) of P(o-Tol)$_3$ are added to this suspension, and the reaction mixture is heated under reflux for 16 h. The mixture is subsequently partitioned between ethyl acetate and water, the organic phase is washed three times with water and dried over Na$_2$SO$_4$ and evaporated in a rotary evaporator. The residue remaining is recrystallised from heptane/toluene. The yield is 43 g (0.15 mol, 38%).

Example 2

4-(2-Bromophenyl)-2,6-diphenylpyrimidine

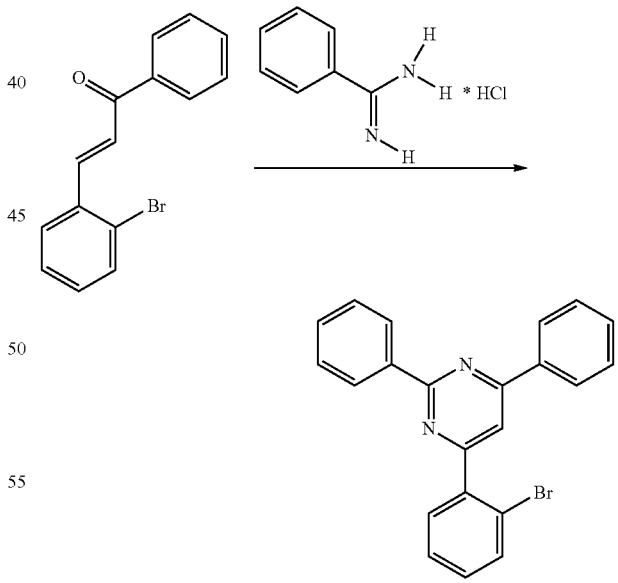

23 g (409 mmol) of potassium hydroxide are dissolved in 500 ml of ethanol, 40 g (255 mmol) of benzamide hydrochloride and 129 g (452 mmol) of 3-(bromophenyl)-1-phenyl-2-propen-1-one, dissolved in 500 ml of ethanol, are added at room temperature, and the mixture is stirred under reflux for 3 h. After cooling to room temperature, the precipitated solid is filtered off with suction, washed with a little ethanol and dried, leaving 55 g (129 mmol), 50%, of the product in the form of colourless crystals.

Example 3

2,4-Bisbiphenyl-3-yl-6-chloro-1,3,5-triazine

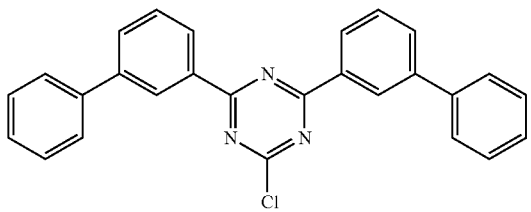 [SMILES: Clc1nc(-c2cccc(-c3ccccc3)c2)nc(-c2cccc(-c3ccccc3)c2)n1]

5.2 g of magnesium (0.215 mol) are initially introduced in a 500 ml four-necked flask, and a solution of 50 g of bromobiphenyl (214 mmol) in 200 ml of THF is slowly added dropwise. The reaction mixture is heated at the boil for 1.5 h and subsequently cooled to room temperature. Cyanogen chloride (17.2 g, 93 mmol) in 150 ml of THF is initially introduced in a second flask and cooled to 0° C. The cooled Grignard reagent is then added dropwise at this temperature, and the mixture is stirred at RT for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from EtOH. The yield is 32.8 g (78 mmol, 84%).

Example 4

2-Chloro-4,6-bis-[1,1';3',1"]terphenyl-5'-yl-1,3,5-triazine

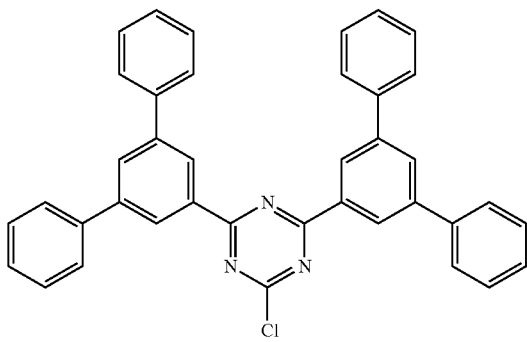 [SMILES: Clc1nc(-c2cc(-c3ccccc3)cc(-c3ccccc3)c2)nc(-c2cc(-c3ccccc3)cc(-c3ccccc3)c2)n1]

3.93 g of magnesium (162 mmol) are initially introduced in a 500 ml four-necked flask, and a solution of 50 g of 5'-bromo-[1,1';3',1"]terphenyl (162 mmol) in 150 ml of THF is slowly added dropwise. The reaction mixture is heated at the boil for 1.5 h and subsequently cooled to room temperature. Cyanogen chloride (13 g, 70 mmol) in 150 ml of THF is initially introduced in a second flask and cooled to 0° C. The cooled Grignard reagent is added dropwise at this temperature, and the mixture is stirred at RT for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from EtOH, The yield is 27.8 g (49 mol, 70%).

Example 5

2-Chloro-4,6-bis-(3-([3,1';5,1"]terphen-1-yl)phen-1-yl)-1,3,5-triazine

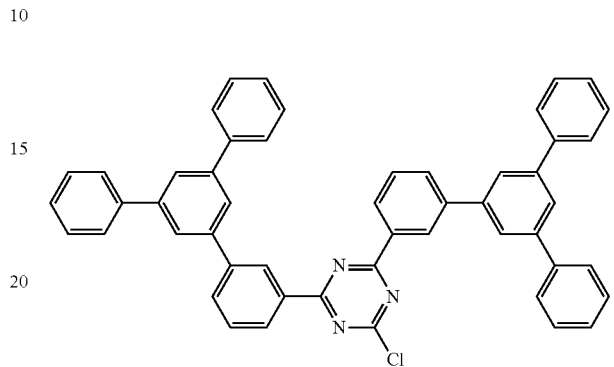

2.0 g of magnesium (81 mmol) are initially introduced in a 500 ml four-necked flask, and a solution of 31.2 g of 5'-(3-bromophenyl)-[1,1';3',1"]terphenyl (81 mmol) in 100 ml of THF is slowly added dropwise. The reaction mixture is heated at the boil for 1.5 h and subsequently cooled to room temperature. Cyanogen chloride (6.4 g, 35 mmol) in 50 ml of THF is initially introduced in a second flask and cooled to 0° C. The cooled Grignard reagent is added dropwise at this temperature, and the mixture is stirred at room temperature for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from toluene. The yield is 6.8 g (9.4 mmol, 28%).

Example 6

3-Bromo-9-[1,1';3',1"]terphenyl-5'-yl-9H-carbazole

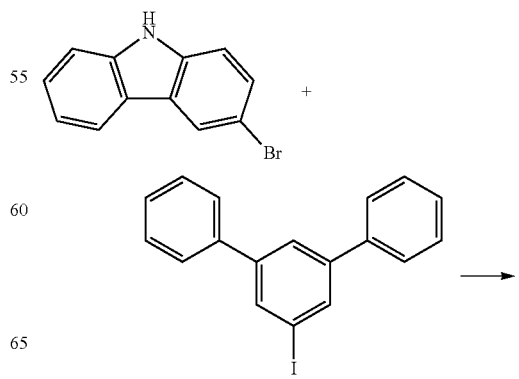

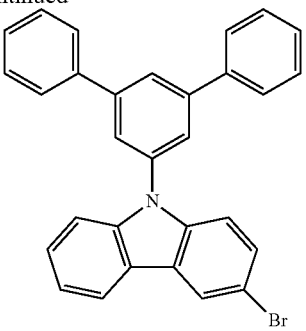

10 g (41 mmol) of 3-bromo-9H-carbazole (CAS 86-74-8) and 16 g (45 mmol, 1.1 eq.) of 5'-iodo-[1,1';3',1"]terphenyl are dissolved in 250 ml of p-xylene together with 9.2 g (160 mmol, 4 eq.) of potassium hydroxide, 300 mg (1.6 mmol, 0.04 eq.) of 1,10-phenanthroline and 160 mg (1.6 mmol, 0.04 eq.) of copper(I) iodide and heated under reflux. When the reaction is complete, the mixture is extracted three times with water, and the organic phase is dried over sodium sulfate, the solvent is removed in vacuo, and the solid obtained is purified by means of column chromatography (ethyl acetate/heptane), giving 17 g (36 mmol, 88%) of the desired product.

The following compounds can be obtained analogously:

| Example | Yield |
|---------|-------|
| 6a | 94% |
| 6b | 91% |
| 6c | 96% |

Example 7

9-(9,9-Dimethyl-9H-fluoren-2yl)-9H-carbazole-3-boronic acid

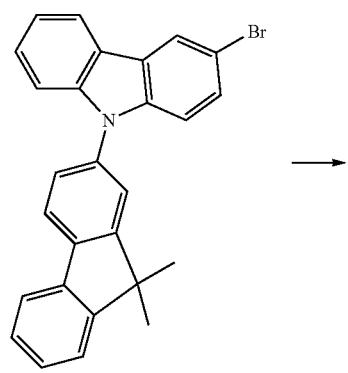

22.3 g (51 mmol) of 3-bromo-9-(9,9-dimethyl-9H-fluoren-2-yl)-9H-carbazole are dissolved in 600 ml of dry THF and cooled to −78° C. At this temperature, 26.2 ml (65.7 mmol/2.5 M in hexane) of n-BuLi are added over the course of about 5 min., and the mixture is subsequently stirred at −78° C. for a further 2.5 h. At this temperature, 7.3 ml (65.7 mmol) of trimethyl borate are added as rapidly as possible, and the reaction is allowed to come slowly to RT (about 18 h). The reaction solution is washed with water, and the precipitated solid and the organic phase are dried azeotropically with toluene. The crude product is washed by stirring with toluene/methylene chloride at about 40° C. and filtered off with suction, giving 17.5 g (85%) of the product as a white solid.

The following compounds can be obtained analogously:

| | Starting material | Product | Yield |
|---|---|---|---|
| 7a | | | 79% |
| 7b | | | 81% |

Example 8

3-(5-Bromobiphenyl-3-yl)-9-phenyl-9H-carbazole

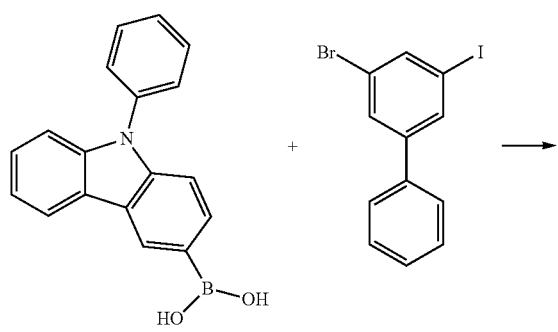

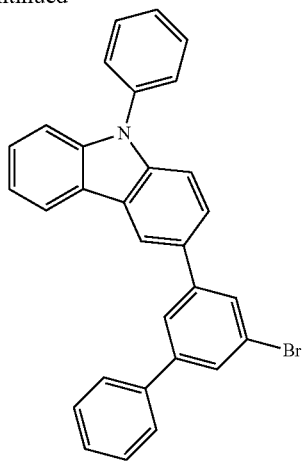

15.5 g (43.3 mmol) of 3-bromo-5-iodobiphenyl and 13.7 g (48 mmol) of (9-phenyl-9H-carbazol-3-yl)boronic acid are dissolved in 80 ml of toluene and degassed. 281 ml of a degassed 2M K$_2$CO$_3$ solution and 2.5 g (2.2 mmol) of Pd(OAc)$_2$ are added. The reaction mixture is subsequently stirred at 80° C. for 48 h under a protective-gas atmosphere. The cooled solution is diluted with toluene, washed a number of times with water, dried and evaporated. The product is purified by column chromatography on silica gel with toluene/heptane (1:2). The purity is 98%. Yield: 17.6 g (37 mmol), 78% of theory.

The following compounds can be obtained analogously;

| | Starting material 1 | Starting material 2 | Product |
|---|---|---|---|
| 8a | 854952-60-6 | 136649-44-0 | |
| 8b | 854952-58-2 | 900806-53-3 | |

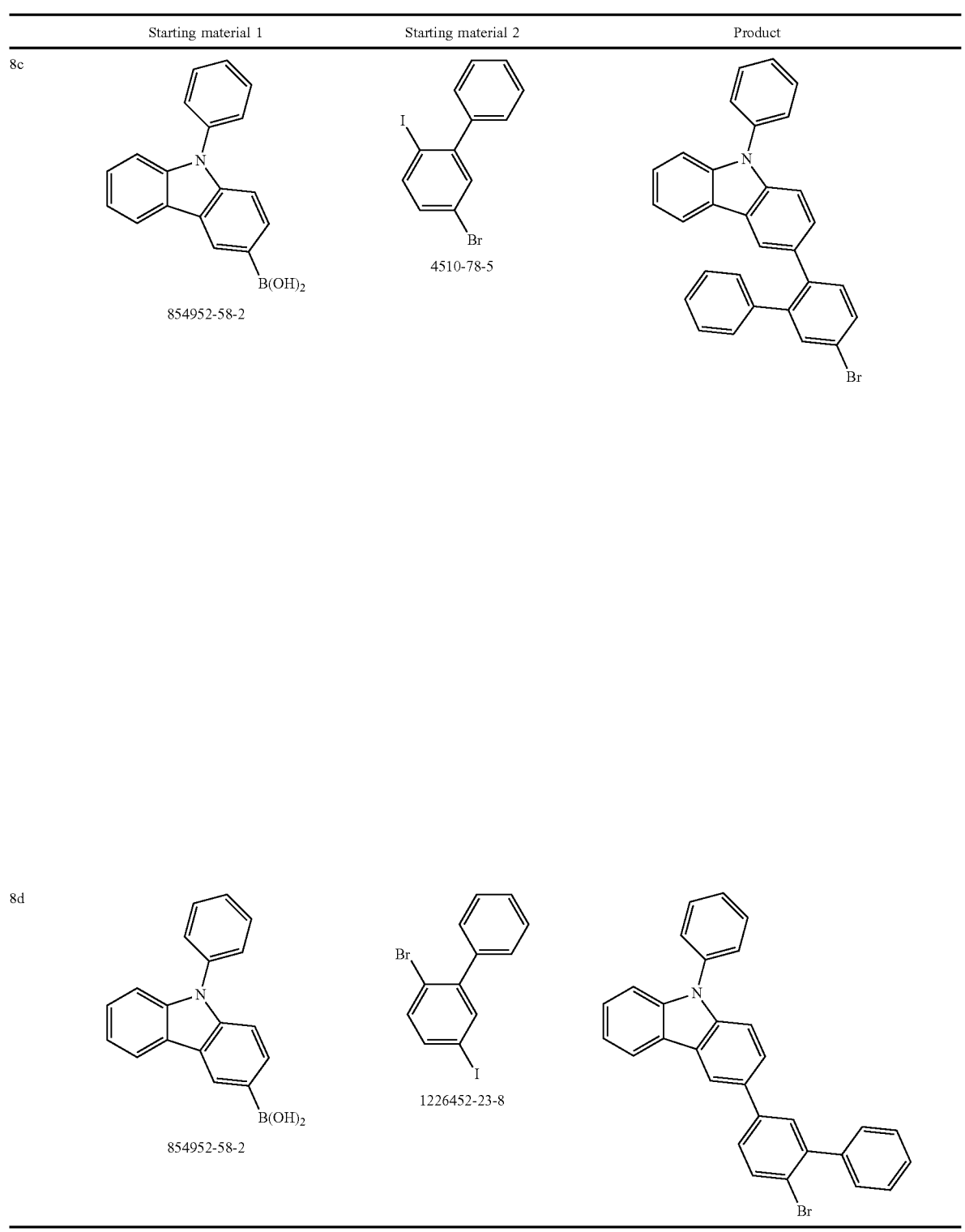
| Yield | |
|---|---|
| 8a | 70% |
| 8b | 69% |
| 8c | 68% |
| 8d | 83% |

Example 9

3-(5-Boronobiphenyl-3-yl)-9-phenyl-9H-carbazole

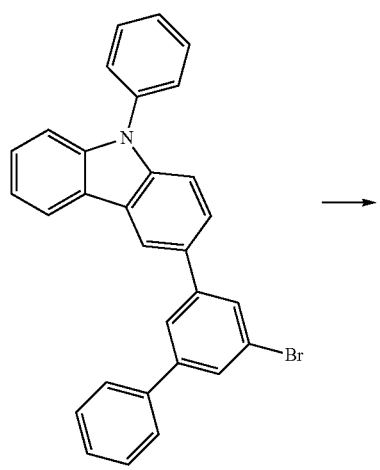 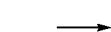 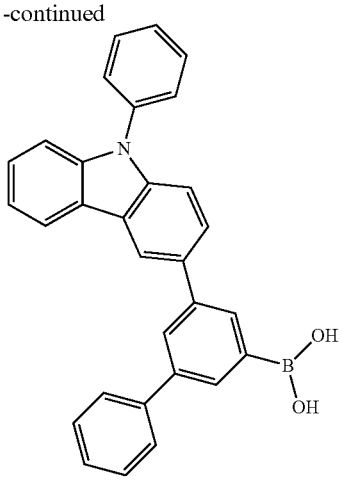

110 ml (276 mmol) of n-butyllithium (2.5 M in hexane) are added dropwise to a solution, cooled to −78° C., of 128 g (270 mmol) of 3-(5-bromobiphenyl-3-yl)-9-phenyl-9H-carbazole in 1500 ml of diethyl ether. The reaction mixture is stirred at −78° C. for 30 min. The mixture is allowed to come to room temperature, is re-cooled to −78° C., and a mixture of 40 ml (351 mmol) of trimethyl borate in 50 ml of diethyl ether is then added rapidly. After warming to −10° C., the mixture is hydrolysed using 135 ml of 2 N hydrochloric acid. The organic phase is separated off, washed with water, dried over sodium sulfate and evaporated to dryness. The residue is taken up in 300 ml of n-heptane, the colourless solid is filtered off with suction, washed with n-heptane and dried in vacuo. Yield: 112 g (256 mmol), 95% of theory.

The following compounds can be obtained analogously:

| | Starting material | Product | Yield |
|---|---|---|---|
| 9a | | | 64% |

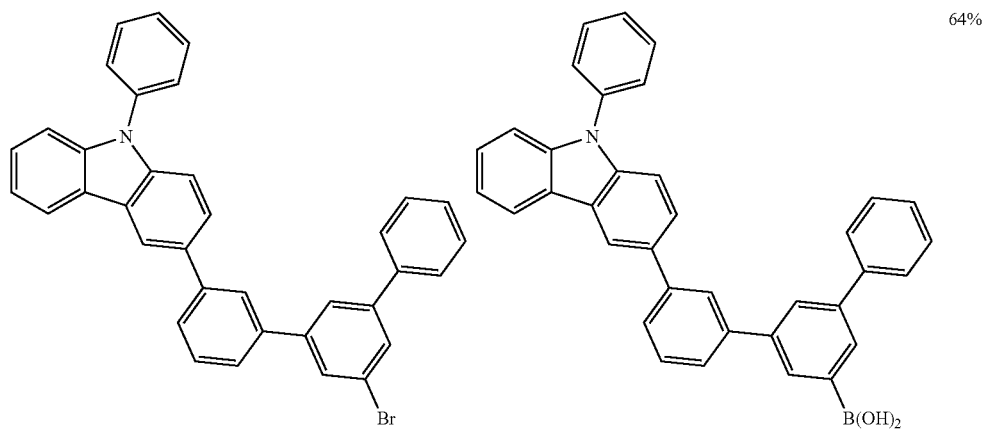

-continued
| | Starting material | Product | Yield |
|---|---|---|---|
| 9b | 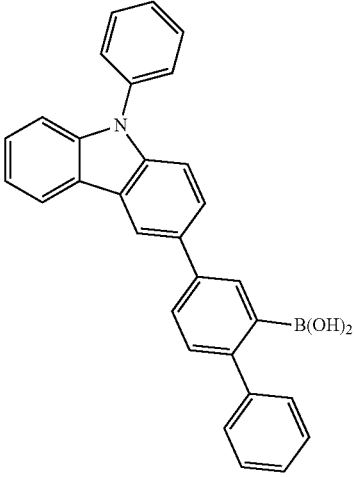 [SMILES: OB(O)c1cc(-c2ccc3c(c2)c2ccccc2n3-c2ccccc2)ccc1-c1ccccc1] | | 60% |
| 9c | | | 63% |
| 9d | | | 69% |

| Starting material | Product | Yield |
|---|---|---|
| 9e 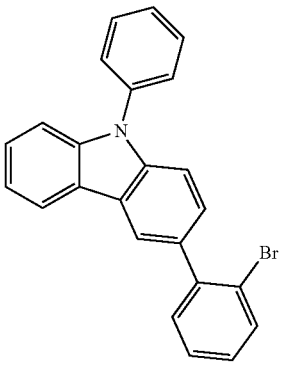 1190100-35-6 | 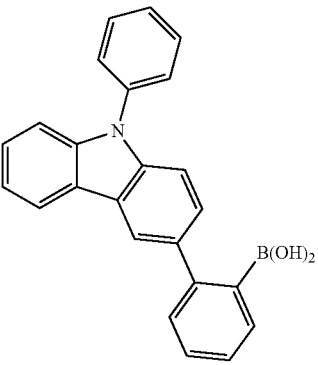 [SMILES: OB(O)c1ccccc1-c1ccc2c(c1)c1ccccc1n2-c1ccccc1] | 59% |
| 9f 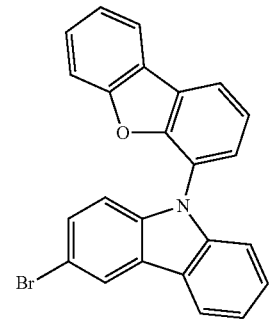 1345970-20-8 | 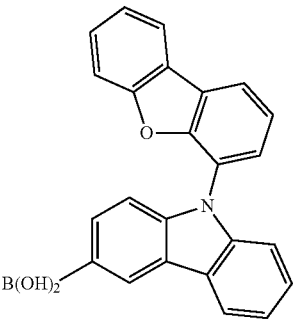 [SMILES: OB(O)c1ccc2c(c1)c1ccccc1n2-c1cccc2c1oc1ccccc12] | 83% |

Example 10e

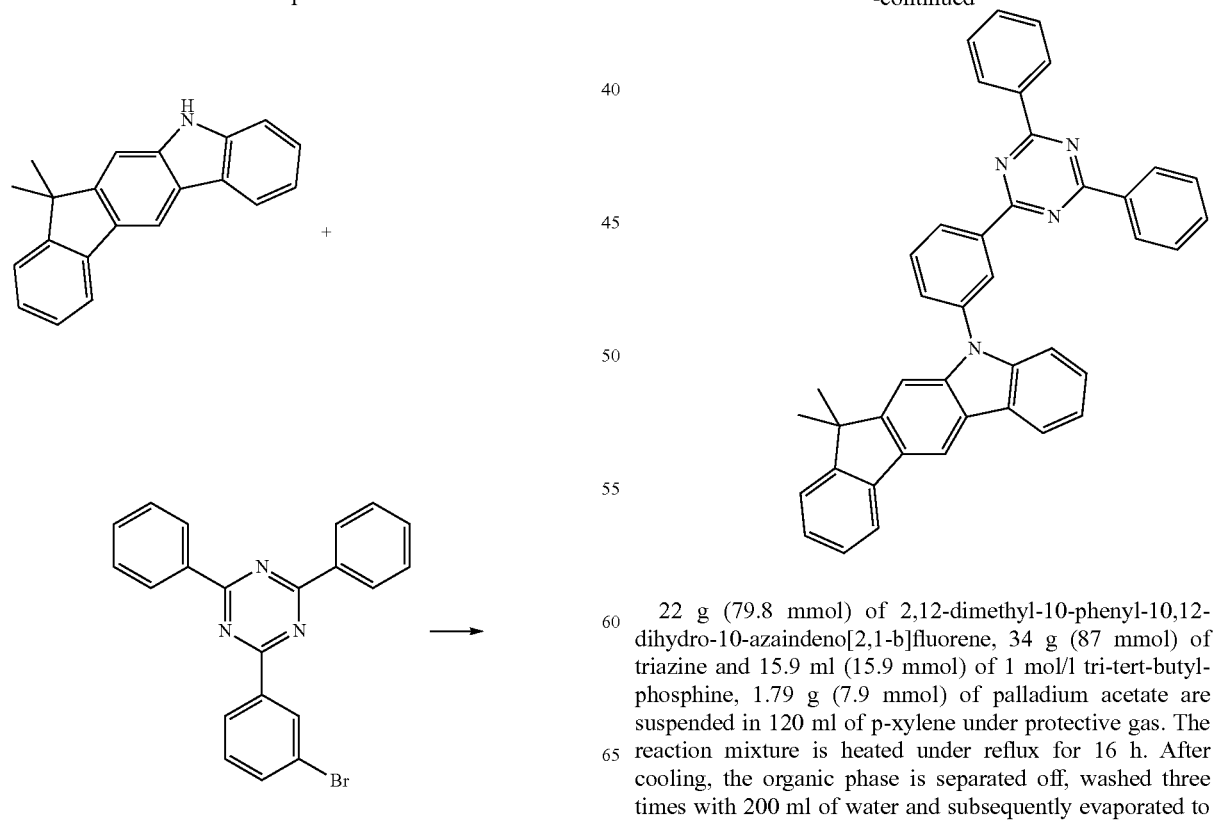

22 g (79.8 mmol) of 2,12-dimethyl-10-phenyl-10,12-dihydro-10-azaindeno[2,1-b]fluorene, 34 g (87 mmol) of triazine and 15.9 ml (15.9 mmol) of 1 mol/l tri-tert-butyl-phosphine, 1.79 g (7.9 mmol) of palladium acetate are suspended in 120 ml of p-xylene under protective gas. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum. The purity is 99.9%. Yield: 38 g (64 mmol), 80% of theory.

The following compounds are obtained analogously:

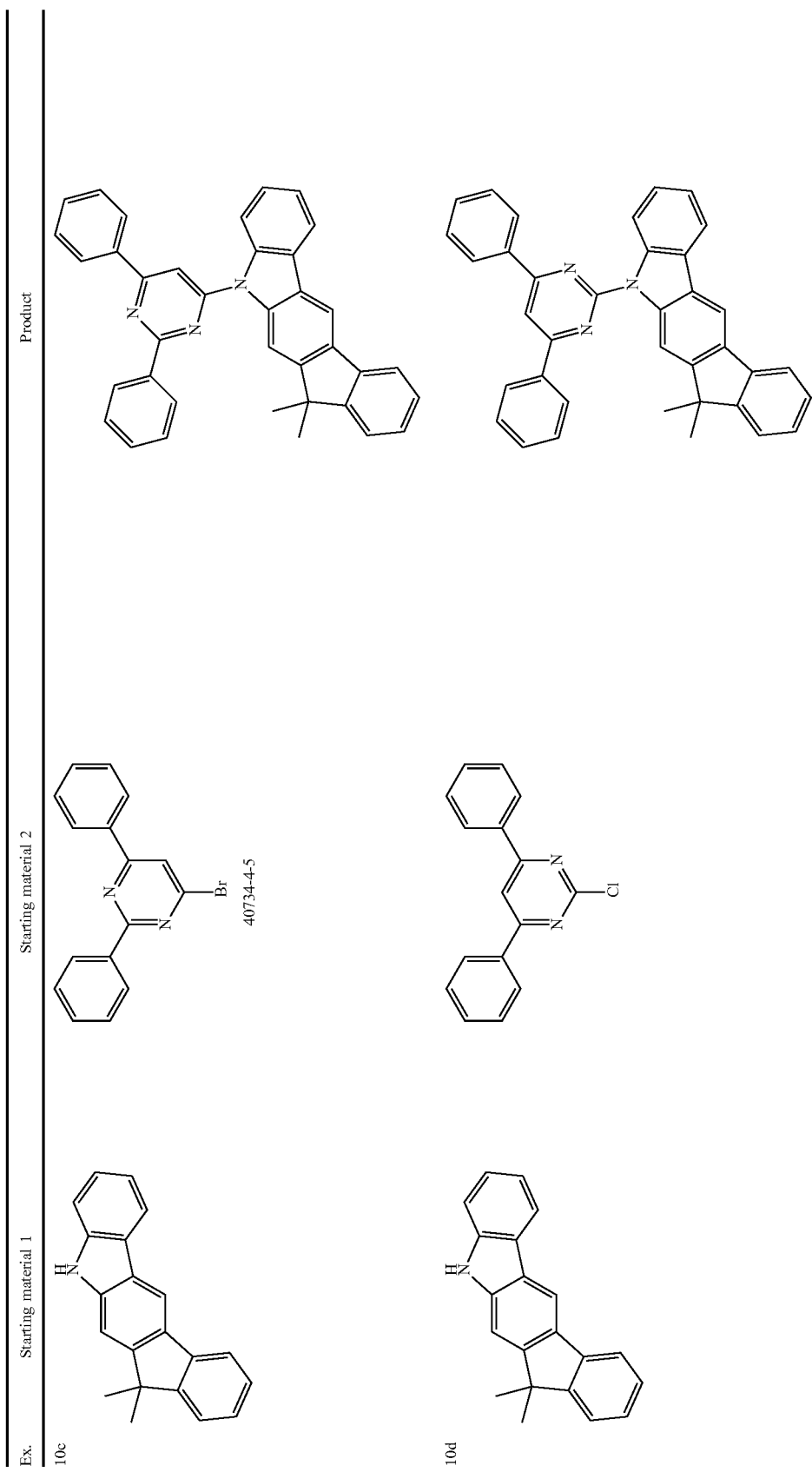

-continued
| Ex. | Starting material 1 | Starting material 2 | Product |
|---|---|---|---|
| 10f | 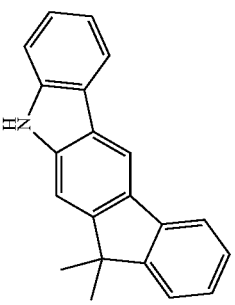 | 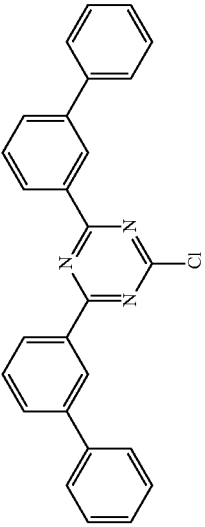 | 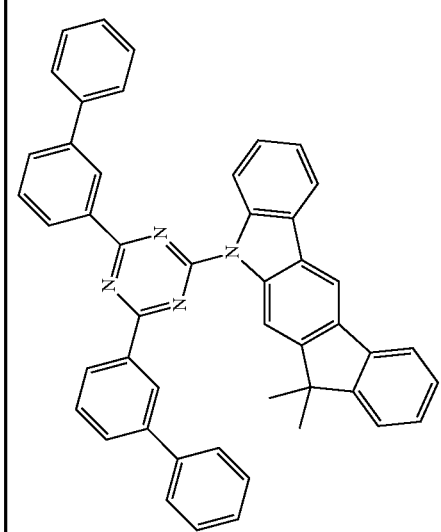 |
| 10g | 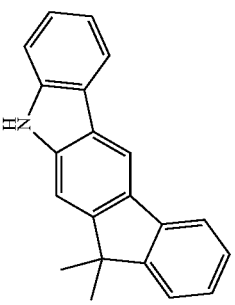 | 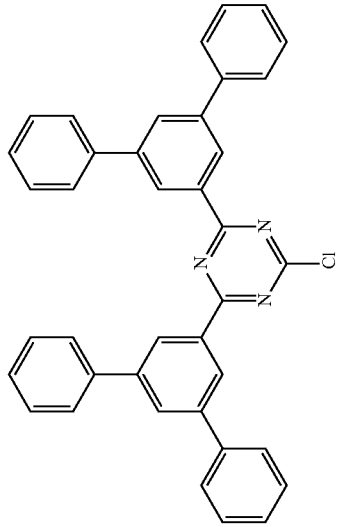 | 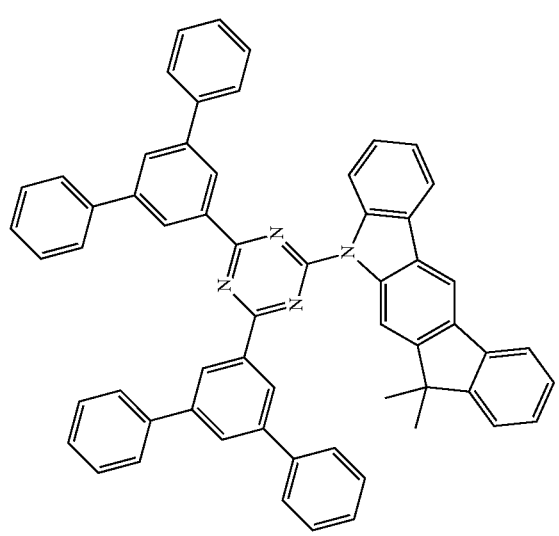 |

-continued

| Ex. | Starting material 1 | Starting material 2 | Product |
|---|---|---|---|
| 10h | | 23449-08-3 | |
| 10i | | | |

| Ex. | Yield |
|-----|-------|
| 10c | 81% |
| 10d | 76% |
| 10f | 72% |
| 10g | 70% |
| 10h | 85% |
| 10i | 80% |

Example 11e

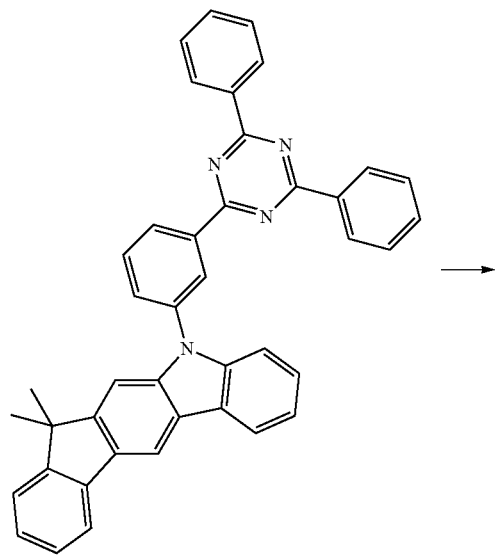 → 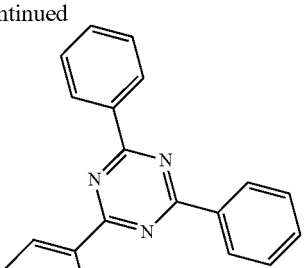

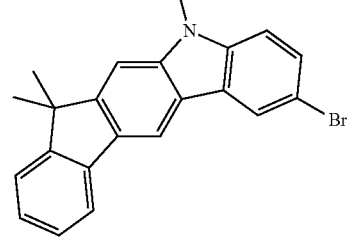

23 g (40.18 mmol) of the starting material are suspended in 800 ml of aceto-nitrile, and 7.15 g (40.18 mmol) of N-bromosuccinimide are added in portions at −20° C. at such a rate that the reaction temperature does not rise above −20° C. The mixture is stirred for a further 18 h while the temperature is allowed to come to RT. The reaction mixture is subsequently evaporated in a rotary evaporator, dissolved in dichloromethane and washed with water. The mixture is dried, evaporated and subsequently recrystallised from toluene to a purity of 99.3%, giving 20.8 g (80%) of the product as a white solid.

The following compounds are obtained analogously:

| Ex. | Starting material | Product |
|-----|-------------------|---------|
| 11c | 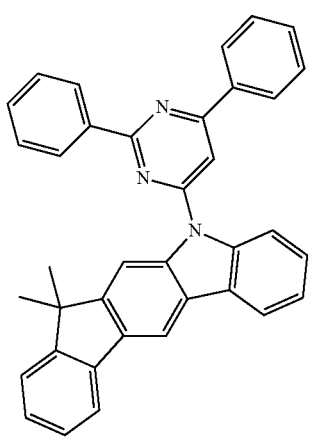 [SMILES: CC1(C)c2ccccc2-c2cc3c4ccccc4n(-c4cc(-c5ccccc5)nc(-c5ccccc5)n4)c3cc21] | 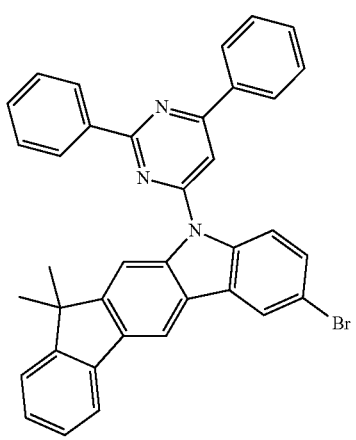 [SMILES: CC1(C)c2ccccc2-c2cc3c4cc(Br)ccc4n(-c4cc(-c5ccccc5)nc(-c5ccccc5)n4)c3cc21] |

-continued
| Ex. | Starting material | Product |
|---|---|---|
| 11d | 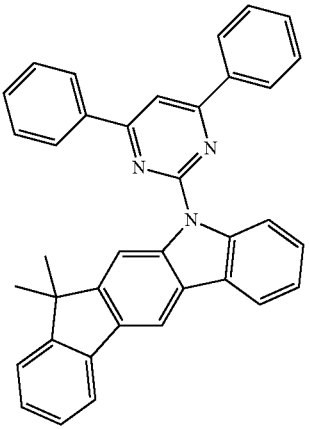 [SMILES: CC1(C)c2ccccc2-c2cc3c4ccccc4n(-c4nc(-c5ccccc5)cc(-c5ccccc5)n4)c3cc21] | 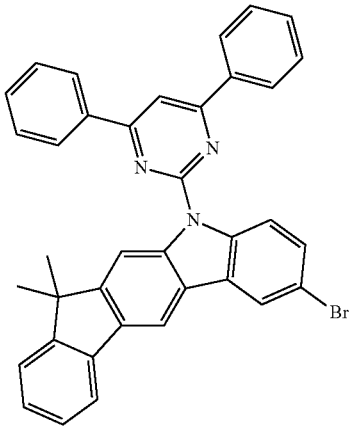 [SMILES: CC1(C)c2ccccc2-c2cc3c4cc(Br)ccc4n(-c4nc(-c5ccccc5)cc(-c5ccccc5)n4)c3cc21] |
| 11f | 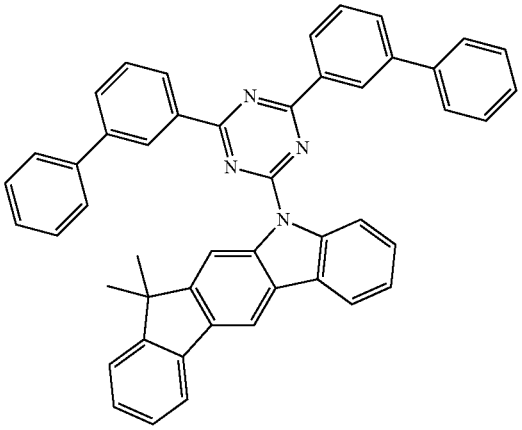 [SMILES: CC1(C)c2ccccc2-c2cc3c4ccccc4n(-c4nc(-c5cccc(-c6ccccc6)c5)nc(-c5cccc(-c6ccccc6)c5)n4)c3cc21] | 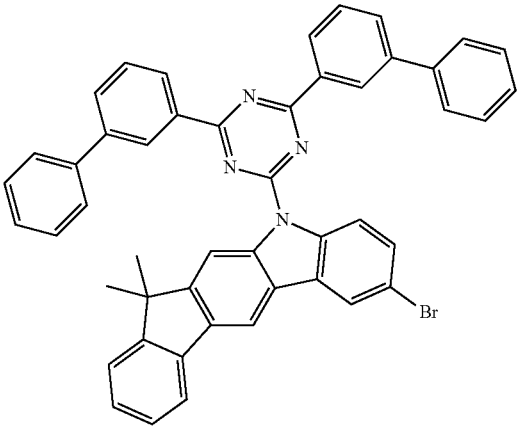 [SMILES: CC1(C)c2ccccc2-c2cc3c4cc(Br)ccc4n(-c4nc(-c5cccc(-c6ccccc6)c5)nc(-c5cccc(-c6ccccc6)c5)n4)c3cc21] |
| 11g | 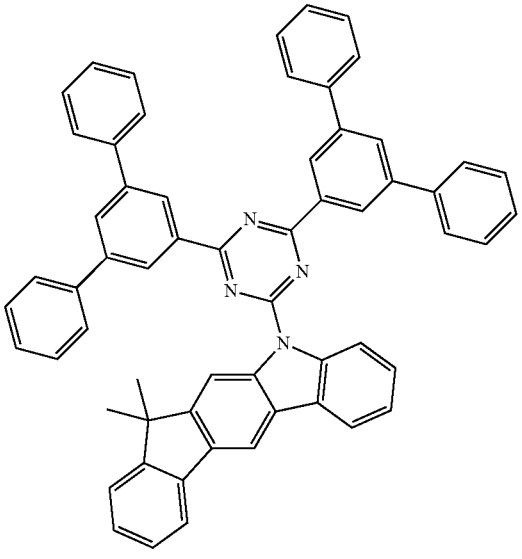 [SMILES: CC1(C)c2ccccc2-c2cc3c4ccccc4n(-c4nc(-c5cc(-c6ccccc6)cc(-c6ccccc6)c5)nc(-c5cc(-c6ccccc6)cc(-c6ccccc6)c5)n4)c3cc21] | 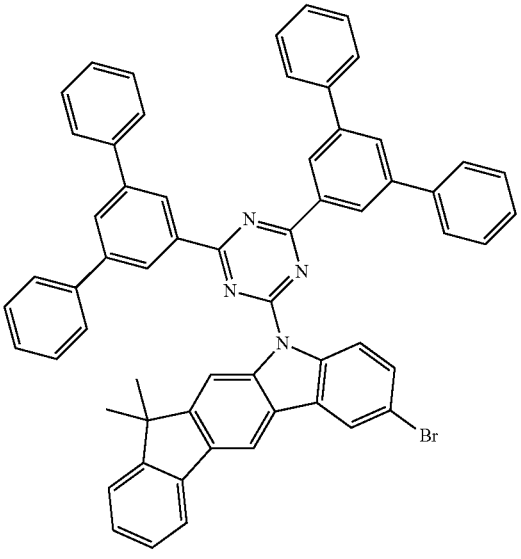 [SMILES: CC1(C)c2ccccc2-c2cc3c4cc(Br)ccc4n(-c4nc(-c5cc(-c6ccccc6)cc(-c6ccccc6)c5)nc(-c5cc(-c6ccccc6)cc(-c6ccccc6)c5)n4)c3cc21] |

| Ex. | Starting material | Product |
|---|---|---|
| 11h | | |
| 11i | | |
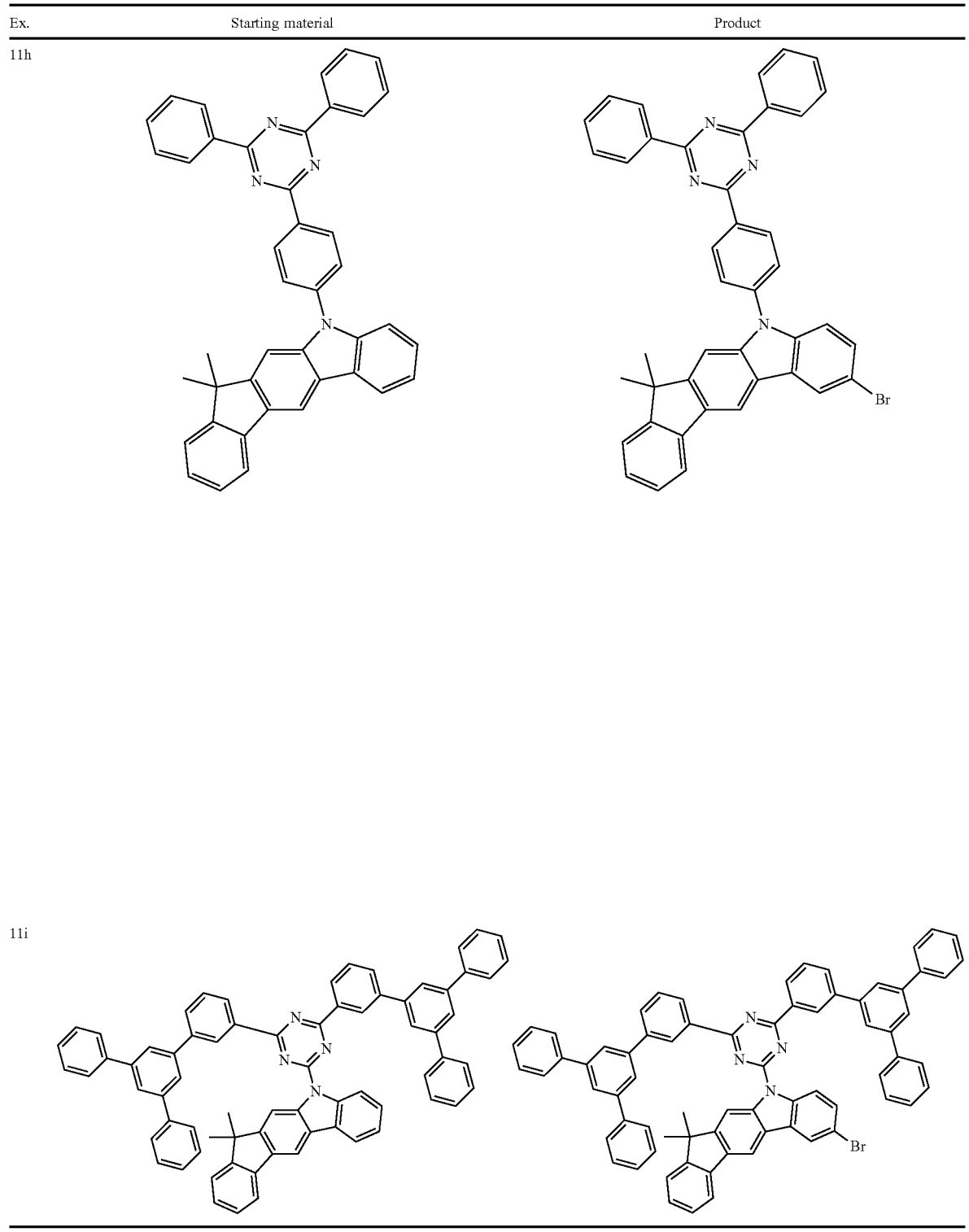
| Ex. | Yield |
|---|---|
| 11c | 81% |
| 11d | 76% |
| 11f | 72% |
| 11g | 70% |
-continued
| Ex. | Yield |
|---|---|
| 11h | 85% |
| 11i | 80% |

II) Synthesis of Compounds According to the Invention

Example 12f

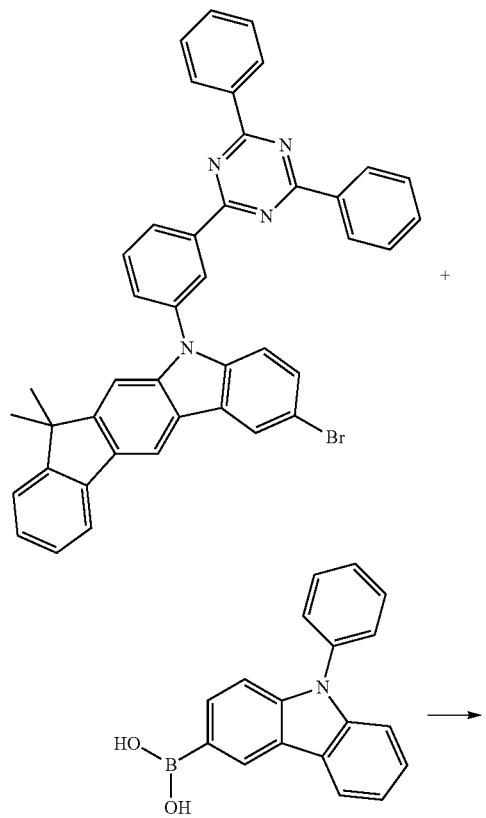

+

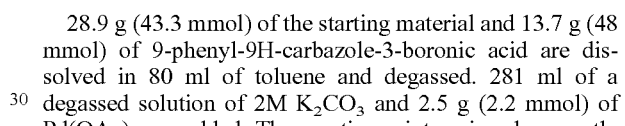

→

28.9 g (43.3 mmol) of the starting material and 13.7 g (48 mmol) of 9-phenyl-9H-carbazole-3-boronic acid are dissolved in 80 ml of toluene and degassed. 281 ml of a degassed solution of 2M $K_2CO_3$ and 2.5 g (2.2 mmol) of Pd(OAc)$_2$ are added. The reaction mixture is subsequently stirred at 80° C. for 48 h under a protective-gas atmosphere. The cooled solution is replenished with toluene, washed a number of times with water, dried and evaporated. The product is purified by column chromatography on silica gel with toluene/heptane (1:2) and finally sublimed in a high vacuum (p=5×10$^{-7}$ mbar). The purity is 99.9%. Yield: 28 g (31 mmol), 80% of theory.

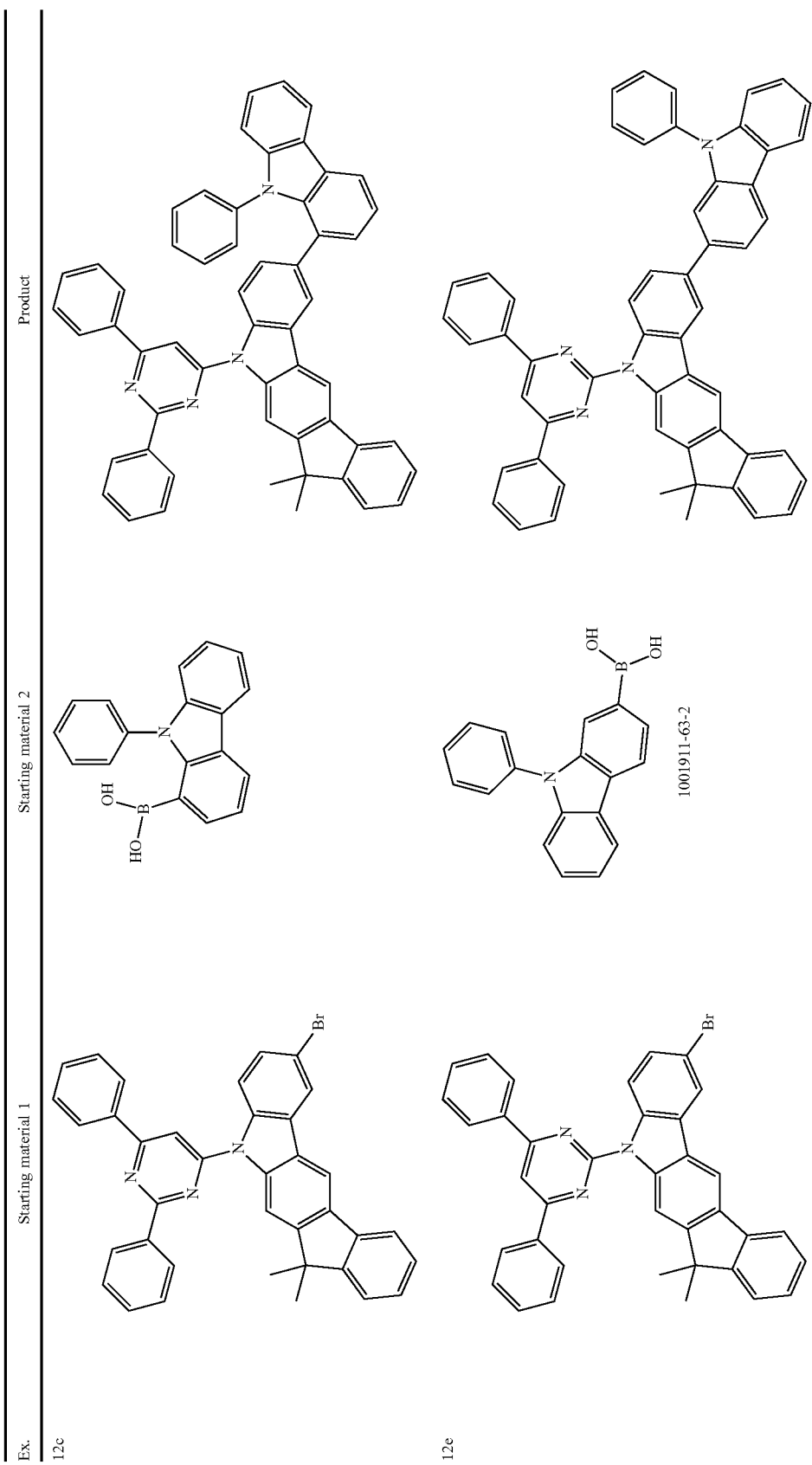

| Ex. | Starting material 1 | Starting material 2 | Product |
|---|---|---|---|
| 12g | 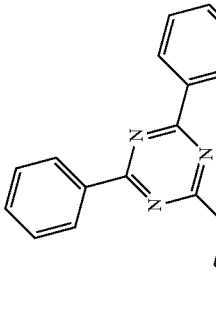 | 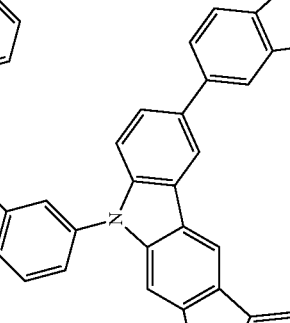
1001911-63-2 |  |

| Ex. | Starting material 1 | Starting material 2 | Product |
|---|---|---|---|
| 12h | 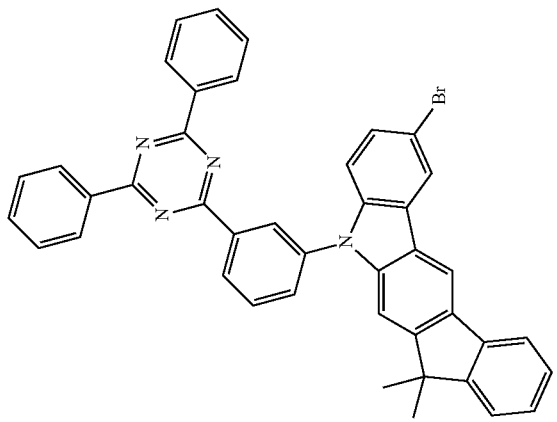 | 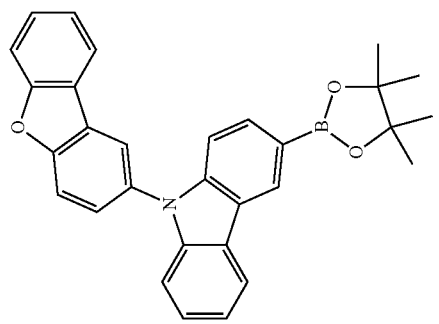
1338488-91-7 | 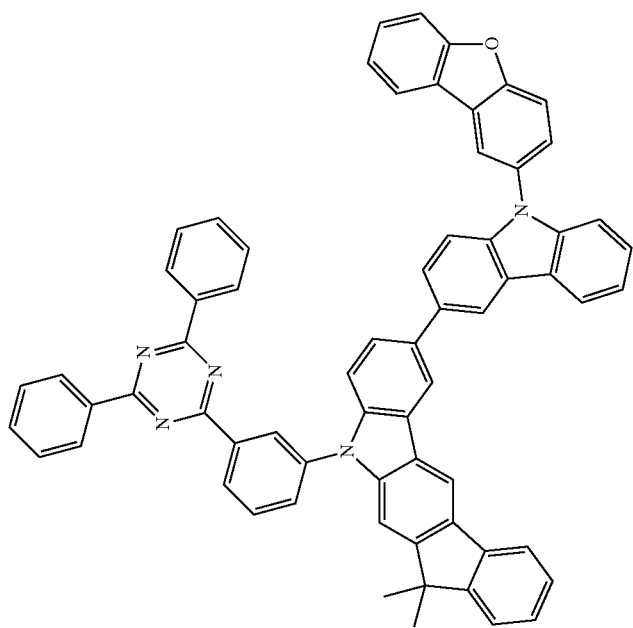 |

| Ex. | Starting material 1 | Starting material 2 | Product |
|---|---|---|---|
| 12j | (structure with triazine, phenyl, carbazole-fluorene, Br) | (dicarbazole with B(OH)₂, N-phenyl) 918137-86-7 | (coupled product) |

| Ex. | Starting material 1 | Starting material 2 | Product |
|---|---|---|---|
| 12i | 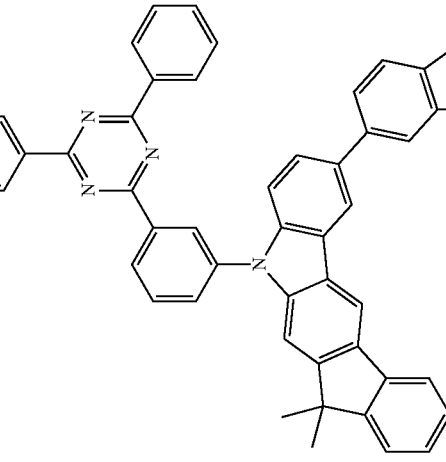 | 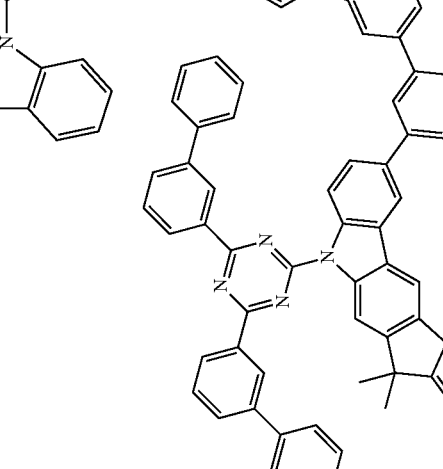 | 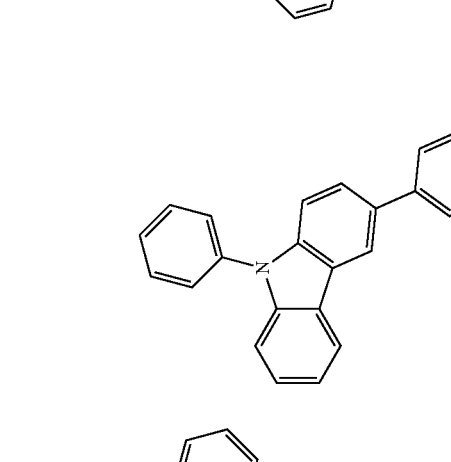 |
| 12k | 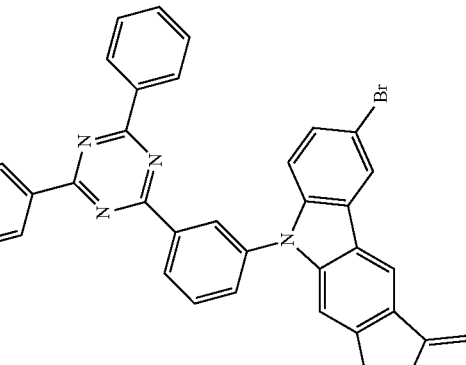 | 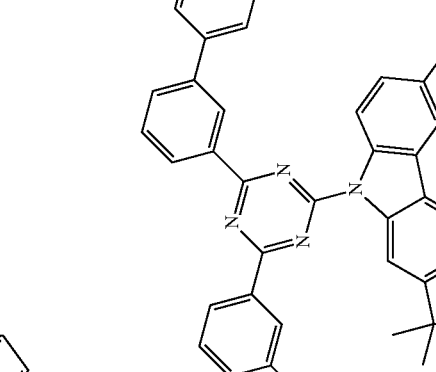  854952-60-6 | 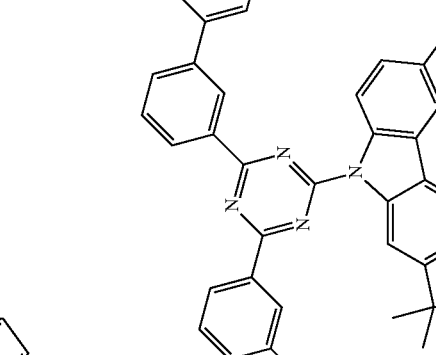 |

| Ex. | Starting material 1 | Starting material 2 | Product |
|---|---|---|---|
| 121 | | | |

| Ex. | Starting material 1 | Starting material 2 | Product |
|---|---|---|---|
| 12m | | | |

-continued

| Ex. | Starting material 1 | Starting material 2 | Product |
|---|---|---|---|
| 12o | | | |

| Ex. | Starting material 1 | Starting material 2 | Product |
|---|---|---|---|
| 12u | 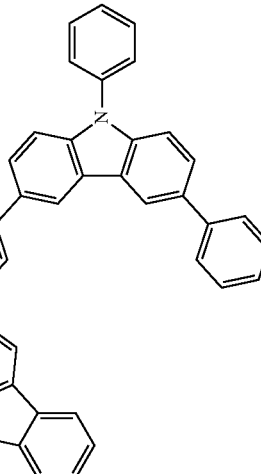 | 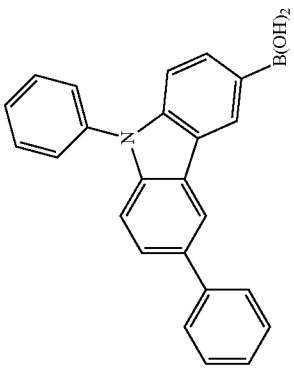
1133058-06-6 | 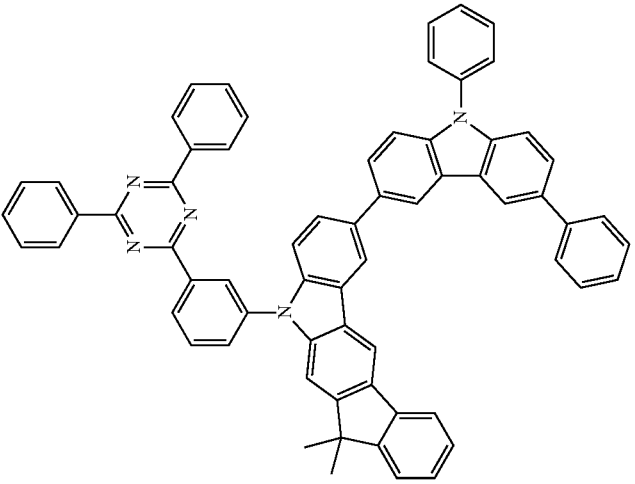 |

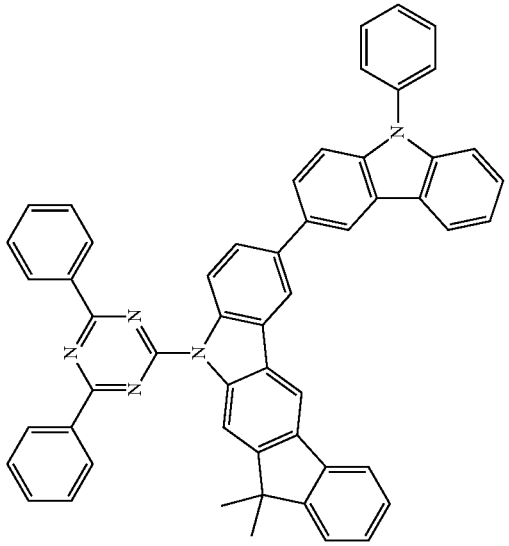

| Ex. | Yield |
|---|---|
| 12c | 81% |
| 12e | 76% |
| 12g | 79% |
| 12h | 82% |
| 12j | 80% |
| 12i | 76% |
| 12k | 72% |
| 12l | 70% |
| 12m | 85% |
| 12o | 80% |
| 12u | 79% |
| 12v | 83% |
| 12w | 78% |

B) Use of the Compounds According to the Invention in OLEDs

The data for various OLEDs are presented in Examples V1 to E9 below (see Tables 1 and 2). Examples V1 to V7 are comparative examples, Examples E1 to E9 are examples according to the invention.

The OLEDs are produced as follows:

Cleaned glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as SdT1:TEG1 (90%:10%) here means that material SdT1 is present in the layer in a proportion by volume of 90% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a current density of 1000 cd/m$^2$, and the CIE 1931 x and y colour coordinates are calculated therefrom. The term U10 in Table 2 denotes the voltage required for a current density of 10 mA/cm$^2$. CE10 and PE10 denote the current and power efficiency respectively which are achieved at 10 mA/cm$^2$. Finally, EQE10 denotes the external quantum efficiency at an operating current density of 10 mA/cm$^2$.

The lifetime LT is defined as the time after which the luminous density has dropped to a certain proportion L1 from the initial luminous density on operation at constant current. An expression of L0;j0=4000 cd/m$^2$ and L1 =80% in Table 2 means that the lifetime indicated in column LT corresponds to the time after which the initial luminous density has dropped from 4000 cd/m$^2$ to 3200 cd/m$^2$. Analogously, L0;j0=20 mA/cm$^2$, L1 =70% means that the luminous density drops to 70% of its initial value after time LT on operation at 20 mA/cm$^2$.

The data measured with the various OLEDs produced are summarised in Table 2.

Some of the examples are explained in greater detail below in order to illustrate the advantages of the compounds according to the invention. All materials used are either known as OLED materials from the prior art, or their synthesis and use is described in the present application.

Use of Compounds According to the Invention as Matrix Materials in Phosphorescent OLEDs In all devices measured, very good performance data, in particular lifetime and efficiency, are obtained on use of the compounds according to the invention as matrix materials in the emitting layer in combination with triplet emitters (Examples E1 to E9, compounds 12f, 12g, 12h, 12k, 12m, 12w).

Compared with compound SdT5 in accordance with the prior art, significantly improved efficiency and lifetime are achieved with compound 12w according to the invention (Examples V7, E7). Compound 12w differs from compound SdT5 through the feature that the CR$_2$ group and the NR group of the indenocarbazole are cis and not trans to one another.

On use of compound SdT4, which contains a pyrimidine group on the carbazole, good performance data are obtained. On replacement of the pyrimidine group by a triazine group, as in compound 12f, however, a 75% improved lifetime is obtained (Examples V3, E1).

The presence of a triazine group compared with a pyrimidine group, bonded to the indenocarbazole unit via a linker, therefore surprisingly gives rise to a significant improvement in the performance data.

On use of compound 12w compared with comparative compound SdT3, which carries a phenyl group instead of a triazine group, an improvement in the performance data is obtained (E7, V6). In particular, the lifetime is significantly improved and the efficiency is slightly improved.

The use of a triazine group instead of a phenyl group as substituent on the nitrogen of the indenocarbazole group thus significantly improves the performance data of the OLED comprising the compound.

Furthermore, very good performance data, in particular a very good lifetime and very good efficiency, are obtained with the compounds according to the invention, even at low emitter concentrations, such as, for example, 5% by vol. (Examples E2, E8 and E9).

Low emitter concentrations in the emitting layer are of high interest for OLEDs, since the metals used in the emitters, such as iridium and platinum, are very rare and thus expensive. Furthermore, the complexes frequently have low temperature stability, so that vapour deposition must be carried out slowly. The vapour-deposition times can be reduced if concentrations and thus the amounts of emitter to be applied by vapour deposition are lower.

The performance data with the devices according to the invention are significantly improved compared with the comparative devices, as shown by the following comparisons. With compound 12w, for example, a significantly improved lifetime and slightly improved efficiency are obtained compared with comparative compounds SdT1 and SdT2, in which no carbazole substituent is present or a carbazole substituent is present which is bonded via nitrogen instead of via the aromatic ring (Examples V2, V5, E8). Very good performance data are obtained in this case, in particular, with compound 12f, in which the indenocarbazole unit is connected to the triazine unit via a phenyl ring (Example E2).

In summary, the combination of the indenocarbazole unit with the carbazole group bonded to the aromatic ring thus produces excellent performance data, which represent a significant improvement over compounds in which no carbazole group is present or the carbazole group is bonded via the nitrogen.

On use as matrix materials in phosphorescent OLEDs, the materials according to the invention thus give rise to significant improvements over the prior art in all parameters, especially with respect to lifetime and power efficiency.

TABLE 1

| Ex. | HTL Thickness | IL Thickness | EBL Thickness | EML Thickness | HBL Thickness | ETL Thickness |
|---|---|---|---|---|---|---|
| V1 | SpA1 70 nm | HATCN 5 nm | SpMA1 90 nm | SdT1:TEG1 (90%:10%) 30 nm | SDT1 10 nm | ST2:LiQ (50%:50%) 30 nm |
| V2 | SpA1 70 nm | HATCN 5 nm | SpMA1 90 nm | SdT1:TEG1 (95%:5%) 30 nm | SDT1 10 nm | ST2:LiQ (50%:50%) 30 nm |
| V3 | SpA1 70 nm | HATCN 5 nm | SpMA1 90 nm | SdT4:TEG1 (90%:10%) 30 nm | SDT1 10 nm | ST2:LiQ (50%:50%) 30 nm |
| V4 | SpA1 70 nm | HATCN 5 nm | SpMA1 90 nm | SdT2:TEG1 (90%:10%) 30 nm | SDT1 10 nm | ST2:LiQ (50%:50%) 30 nm |
| V5 | SpA1 70 nm | HATCN 5 nm | SpMA1 90 nm | SdT2:TEG1 (95%:5%) 30 nm | SDT1 10 nm | ST2:LiQ (50%:50%) 30 nm |
| V6 | SpA1 70 nm | HATCN 5 nm | SpMA1 90 nm | SdT3:TEG1 (90%:10%) 30 nm | SDT1 10 nm | ST2:LiQ (50%:50%) 30 nm |
| V7 | SpA1 70 nm | HATCN 5 nm | SpMA1 90 nm | SdT5:TEG1 (90%:10%) 30 nm | SDT1 10 nm | ST2:LiQ (50%:50%) 30 nm |
| E1 | SpA1 70 nm | HATCN 5 nm | SpMA1 90 nm | 12f:TEG1 (90%:10%) 30 nm | SDT1 10 nm | ST2:LiQ (50%:50%) 30 nm |
| E2 | SpA1 70 nm | HATCN 5 nm | SpMA1 90 nm | 12f:TEG1 (95%:5%) 30 nm | SDT1 10 nm | ST2:LiQ (50%:50%) 30 nm |
| E3 | SpA1 70 nm | HATCN 5 nm | SpMA1 90 nm | 12g:TEG1 (90%:10%) 30 nm | SDT1 10 nm | ST2:LiQ (50%:50%) 30 nm |
| E4 | SpA1 70 nm | HATCN 5 nm | SpMA1 90 nm | 12h:TEG1 (90%:10%) 30 nm | SDT1 10 nm | ST2:LiQ (50%:50%) 30 nm |
| E5 | SpA1 70 nm | HATCN 5 nm | SpMA1 90 nm | 12k:TEG1 (90%:10%) 30 nm | SDT1 10 nm | ST2:LiQ (50%:50%) 30 nm |
| E6 | SpA1 70 nm | HATCN 5 nm | SpMA1 90 nm | 12m:TEG1 (90%:10%) 30 nm | SDT1 10 nm | ST2:LiQ (50%:50%) 30 nm |
| E7 | SpA1 70 nm | HATCN 5 nm | SpMA1 90 nm | 12w:TEG1 (90%:10%) 30 nm | SDT1 10 nm | ST2:LiQ (50%:50%) 30 nm |
| E8 | SpA1 70 nm | HATCN 5 nm | SpMA1 90 nm | 12w:TEG1 (95%:5%) 30 nm | SDT1 10 nm | ST2:LiQ (50%:50%) 30 nm |
| E9 | SpA1 90 nm | HATCN 5 nm | SpMA1 130 nm | 12f:TER1 (94%:6%) 40 nm | — | ST2:LiQ (50%:50%) 40 nm |

TABLE 2

Data for the OLEDs

| Ex. | U10 (V) | CE10 (cd/A) | PE10 (lm/W) | EQE10 | CIE x/y | L0; j0 | L1 % | LT (h) |
|---|---|---|---|---|---|---|---|---|
| V1 | 4.8 | 52 | 32 | 13.9% | 0.33/0.62 | 20 mA/cm$^2$ | 80 | 145 |
| V2 | 4.7 | 46 | 31 | 12.4% | 0.34/0.63 | 20 mA/cm$^2$ | 80 | 130 |

TABLE 2-continued
Data for the OLEDs
| Ex. | U10 (V) | CE10 (cd/A) | PE10 (lm/W) | EQE10 | CIE x/y | L0; j0 | L1 % | LT (h) |
|---|---|---|---|---|---|---|---|---|
| V3 | 5.1 | 54 | 33 | 14.8% | 0.34/0.63 | 20 mA/cm$^2$ | 80 | 120 |
| V4 | 4.5 | 44 | 31 | 12.1% | 0.33/0.63 | 20 mA/cm$^2$ | 80 | 125 |
| V5 | 4.6 | 39 | 27 | 10.8% | 0.34/0.63 | 20 mA/cm$^2$ | 80 | 110 |
| V6 | 5.5 | 47 | 27 | 13.0% | 0.34/0.63 | 20 mA/cm$^2$ | 80 | 85 |
| V7 | 4.6 | 37 | 25 | 10.4% | 0.33/0.63 | 20 mA/cm$^2$ | 80 | 120 |
| E1 | 4.2 | 54 | 40 | 14.6% | 0.33/0.62 | 20 mA/cm$^2$ | 80 | 210 |
| E2 | 4.2 | 53 | 39 | 14.3% | 0.34/0.62 | 20 mA/cm$^2$ | 80 | 185 |
| E3 | 4.4 | 48 | 34 | 13.3% | 0.33/0.62 | 20 mA/cm$^2$ | 80 | 235 |
| E4 | 4.6 | 46 | 32 | 12.7% | 0.33/0.62 | 20 mA/cm$^2$ | 80 | 195 |
| E5 | 4.7 | 41 | 27 | 11.3% | 0.32/0.62 | 20 mA/cm$^2$ | 80 | 160 |
| E6 | 4.4 | 50 | 35 | 13.5% | 0.34/0.63 | 20 mA/cm$^2$ | 80 | 220 |
| E7 | 4.7 | 49 | 33 | 13.8% | 0.33/0.63 | 20 mA/cm$^2$ | 80 | 165 |
| E8 | 4.7 | 48 | 32 | 13.4% | 0.34/0.63 | 20 mA/cm$^2$ | 80 | 180 |
| E9 | 4.8 | 12.7 | 8.4 | 13.9% | 0.67/0.33 | 4000 cd/m$^2$ | 80 | 470 |
TABLE 3
Structural formulae of the materials used in the OLEDs
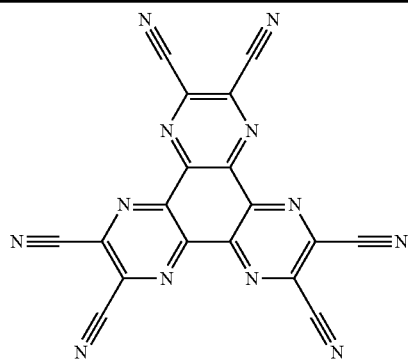
HATCN
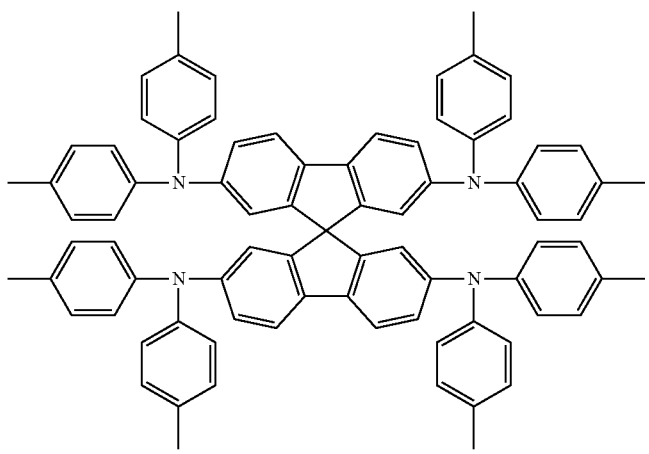
SpA1
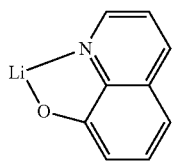
LiQ TABLE 3-continued
Structural formulae of the materials used in the OLEDs
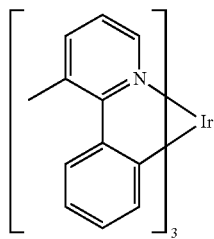
TEG1
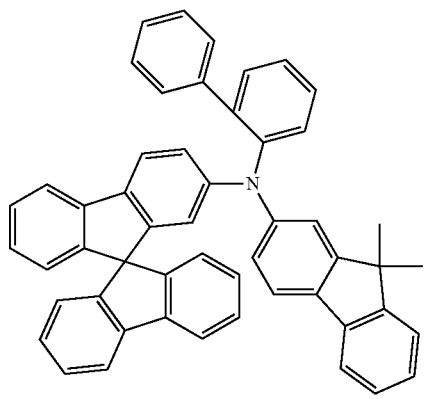 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
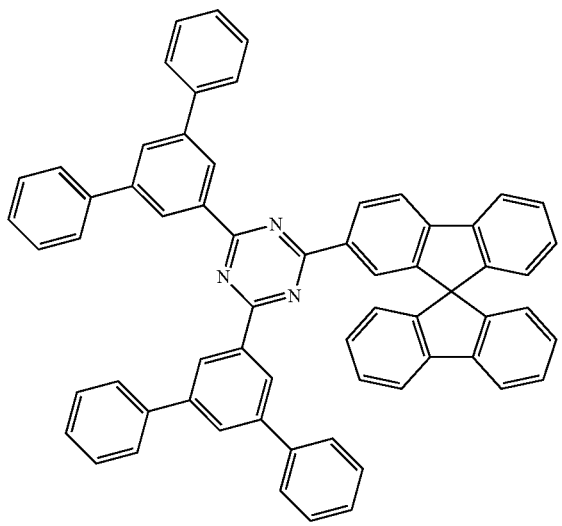 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
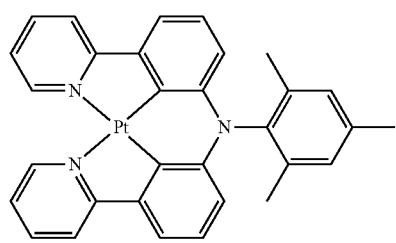
TER1

TABLE 3-continued
Structural formulae of the materials used in the OLEDs
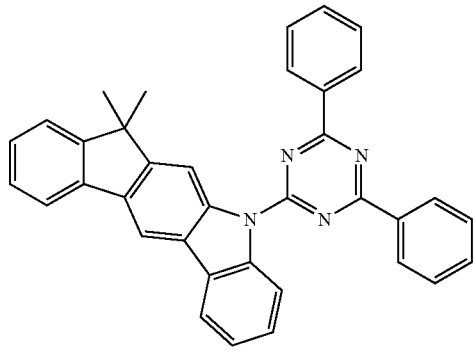 [SMILES: CC1(C)c2ccccc2-c2cc3c4ccccc4n(-c4nc(-c5ccccc5)nc(-c5ccccc5)n4)c3cc21]
SdT1
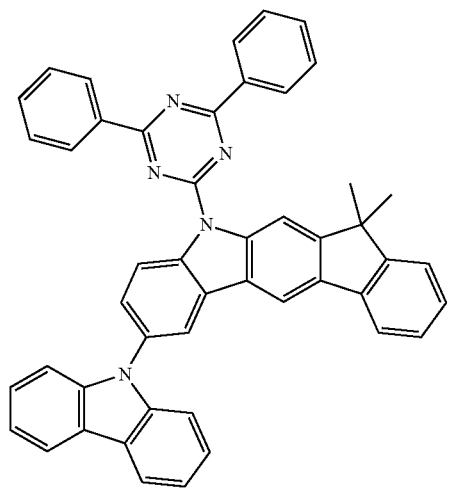 [SMILES: CC1(C)c2ccccc2-c2cc3c4cc(-n5c6ccccc6c6ccccc65)ccc4n(-c4nc(-c5ccccc5)nc(-c5ccccc5)n4)c3cc21]
SdT2
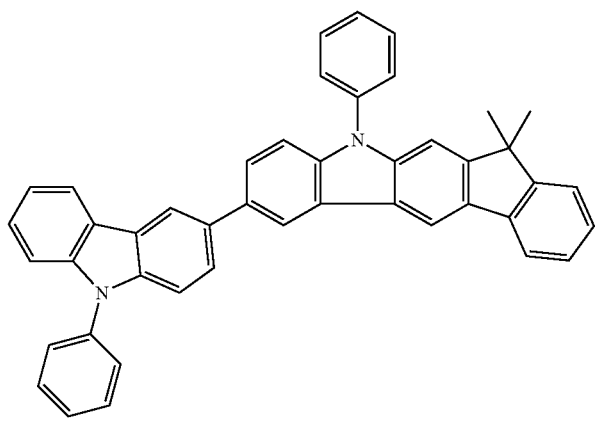 [SMILES: CC1(C)c2ccccc2-c2cc3c4cc(-c5ccc6c(c5)c5ccccc5n6-c5ccccc5)ccc4n(-c4ccccc4)c3cc21]
SdT3

TABLE 3-continued
Structural formulae of the materials used in the OLEDs
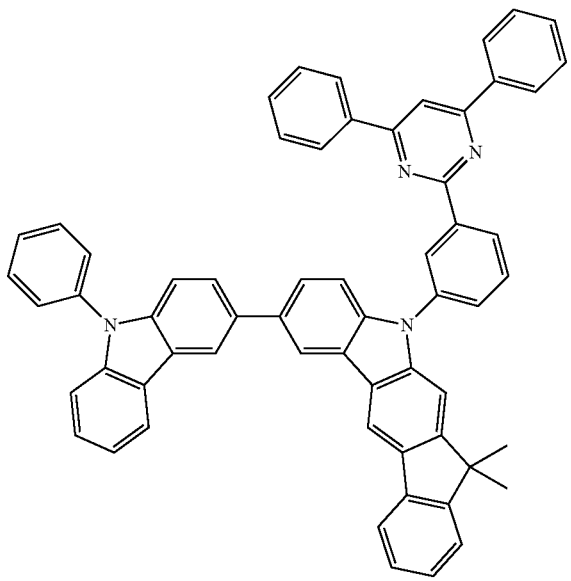 [SMILES: CC1(C)c2ccccc2-c2cc3c4cc(-c5ccc6c(c5)c5ccccc5n6-c5ccccc5)ccc4n(-c4cccc(-c5nc(-c6ccccc6)cc(-c6ccccc6)n5)c4)c3cc21]
SdT4
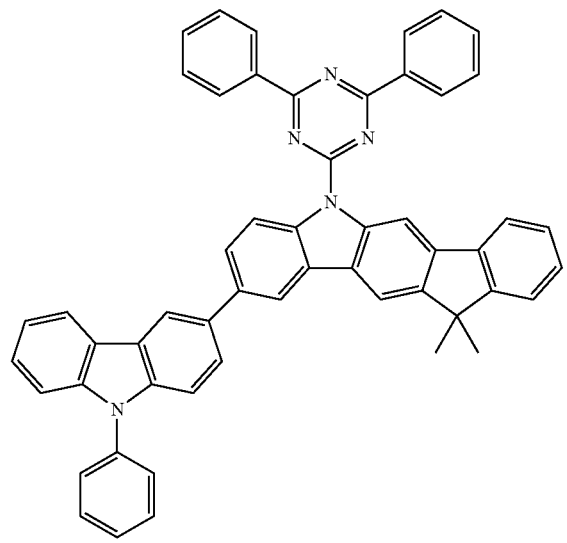 [SMILES: CC1(C)c2ccccc2-c2cc3c(cc21)c1cc(-c2ccc4c(c2)c2ccccc2n4-c2ccccc2)ccc1n3-c1nc(-c2ccccc2)nc(-c2ccccc2)n1]
SdT5

TABLE 3-continued
Structural formulae of the materials used in the OLEDs
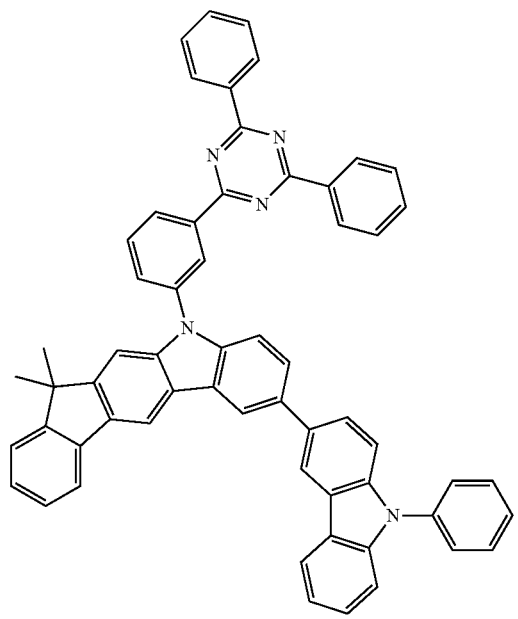 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21]
12f
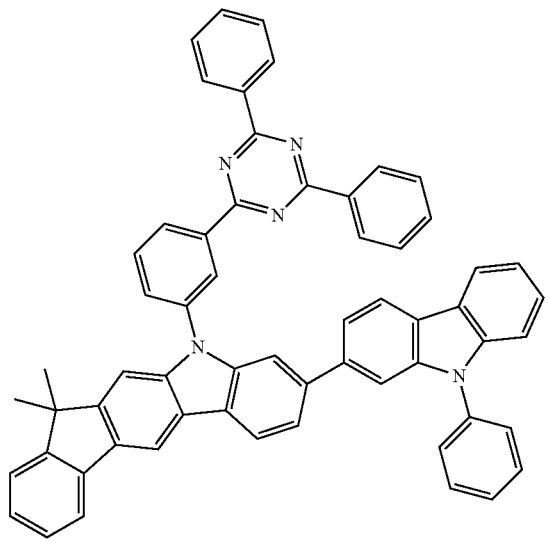 [SMILES: CC1(C)c2ccccc2-c2cc3c4ccc(-c5ccc6c7ccccc7n(-c7ccccc7)c6c5)cc4n(-c4cccc(-c5nc(-c6ccccc6)nc(-c6ccccc6)n5)c4)c3cc21]
12g TABLE 3-continued
Structural formulae of the materials used in the OLEDs
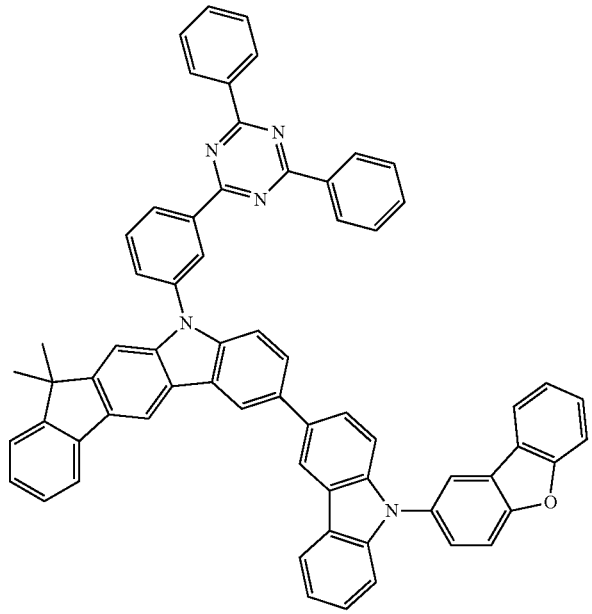 [SMILES: CC1(C)c2ccccc2-c2cc3c4cc(-c5ccc6c(c5)c5ccccc5n6-c5ccc6oc7ccccc7c6c5)ccc4n(-c4cccc(-c5nc(-c6ccccc6)nc(-c6ccccc6)n5)c4)c3cc21]
12h
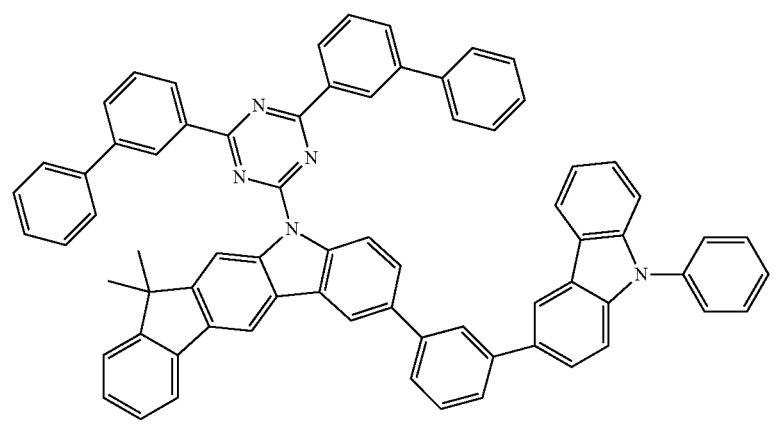 [SMILES: CC1(C)c2ccccc2-c2cc3c4cc(-c5cccc(-c6ccc7c(c6)c6ccccc6n7-c6ccccc6)c5)ccc4n(-c4nc(-c5cccc(-c6ccccc6)c5)nc(-c5cccc(-c6ccccc6)c5)n4)c3cc21]
12k TABLE 3-continued
Structural formulae of the materials used in the OLEDs
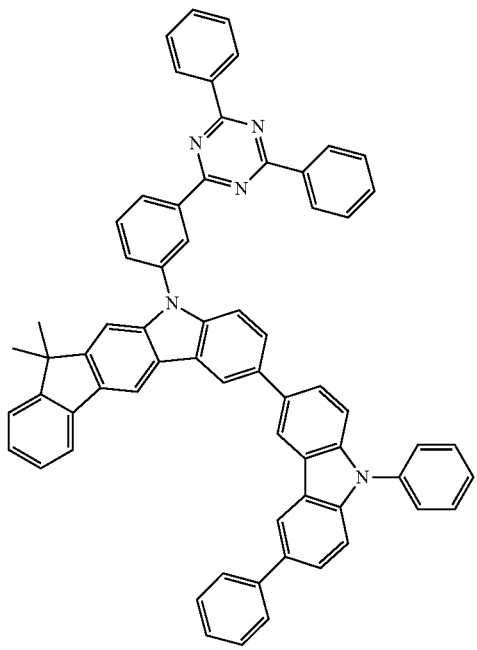 [SMILES: CC1(C)c2ccccc2-c2cc3c4cc(-c5ccc6c(c5)c5cc(-c7ccccc7)ccc5n6-c5ccccc5)ccc4n(-c4cccc(-c5nc(-c6ccccc6)nc(-c6ccccc6)n5)c4)c3cc21]
12m
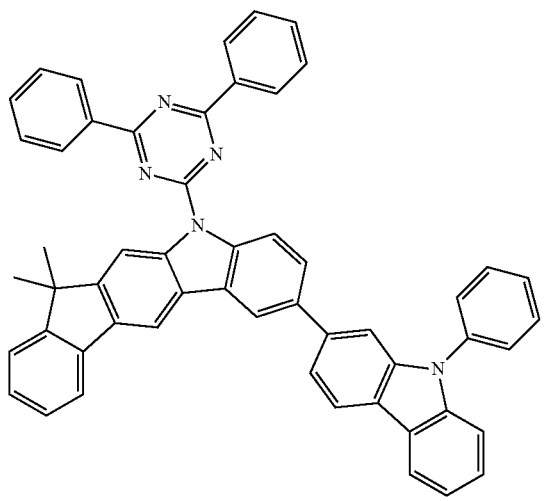 [SMILES: CC1(C)c2ccccc2-c2cc3c4cc(-c5ccc6c7ccccc7n(-c7ccccc7)c6c5)ccc4n(-c4nc(-c5ccccc5)nc(-c5ccccc5)n4)c3cc21]
12w

The invention claimed is:
1. A compound of a formula (I)

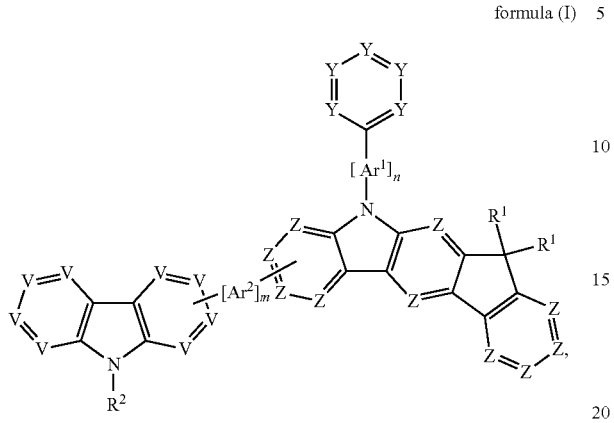

formula (I)

where:
Y is equal to N or $CR^1$ where the group of the formula (Y):

as constituent of the formula (I) conforms to the following formula (Y-1),

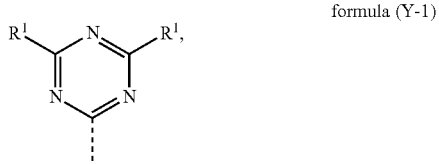

formula (Y-1)

where the dashed line denotes the bond to the remainder of the compound;
Z is equal to $CR^1$ or N;
V is equal to $CR^2$ or N;
$Ar^1$ is an aromatic or heteroaromatic ring system having 6 to 40 aromatic ring atoms, which is optionally substituted by one or more radicals $R^1$;
$Ar^2$ is an aromatic or heteroaromatic ring system having 6 to 40 aromatic ring atoms, which is optionally substituted by one or more radicals $R^1$;
$R^1$ is on each occurrence, identically or differently, H, D, F, Br, Cl, I, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by
—$R^3C=CR^3$—, —C≡C—, $Si(R^3)_2$, C=O, C=$NR^3$, —C(=O)O—, —C(=O)$NR^3$—, $NR^3$, $P(=O)(R^3)$, —O—, —S—, SO or $SO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$, where two or more radicals $R^1$ is optionally linked to one another and may form a ring;
$R^2$ is on each occurrence, identically or differently, H, D, F, Br, Cl, I, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by
—$R^3C=CR^3$—, —C≡C—, $Si(R^3)_2$, C=O, C=$NR^3$, —C(=O)O—, —C(=O)$NR^3$—, $NR^3$, $P(=O)(R^3)$, —O—, —S—, SO or $SO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$;
$R^3$ is on each occurrence, identically or differently, H, D, F, Br, Cl, I, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups is optionally replaced by
—$R^4C=CR^4$—, —C≡C—, $Si(R^4)_2$, C=O, C=$NR^4$, —C(=O)O—, —C(=O)$NR^4$—, $NR^4$, $P(=O)(R^4)$, —O—, —S—, SO or $SO_2$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which is optionally substituted by one or more radicals $R^4$, where two or more radicals $R^3$ is optionally linked to one another and may form a ring;
$R^4$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents $R^4$ here is optionally linked to one another and may form a ring;
n is equal to 1; and
m is equal to 0 or 1.
2. The compound according to claim 1, wherein the index m is equal to 0.
3. The compound according to claim 1, wherein Z is equal to $CR^1$.
4. The compound according to claim 1, wherein V is equal to $CR^2$.
5. The compound according to claim 1, wherein the index m is equal to 0, Z is equal to $CR^1$, V is equal to $CR^2$.
6. The compound according to claim 1, wherein $Ar^1$ represents a group of the following formula ($Ar^1$—I)

formula ($Ar^1$-I)

--[-$Ar^3$-]$_k$--, where the dashed lines represent the bonds to the indeno-carbazole group and the six-membered ring containing the groups Y, $Ar^3$ is on each occurrence, identically or differently, an aryl or heteroaryl group having 6 to 18 aromatic ring atoms, which is optionally substituted by one or more radicals $R^1$, where $R^1$ is defined as in claim 1; and k is 1, 2, 3 or 4, where the index k is selected so that the number of aromatic ring atoms in the entire group $Ar^1$ does not exceed the number 40.

7. An oligomer, polymer or dendrimer containing one or more compounds according to claim 1, where the bond(s) to the polymer, oligomer or dendrimer is optionally localized at any position in formula (I) which are substituted by $R^1$ or $R^2$.

8. A formulation comprising at least one compound according to claim 1 and at least one solvent.

9. A formulation comprising at least one polymer, oligomer or dendrimer according to claim 7 and at least one solvent.

10. An electronic device selected from organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs), which comprises at least one compound according to claim 1.

11. An organic electroluminescent device which comprises an anode, a cathode and at least one emitting layer, where at least one layer of the device, selected from emitting layers, electron-transport layers, electron-injection layers and hole-blocking layers, comprises at least one compound according to claim 1.

12. The device according to claim 11, wherein the compound is present in an emitting layer in combination with one or more phosphorescent emitter compounds.

13. A process for the preparation of the compound according to claim 1 which comprises reacting an indenocarbazole compound with an aromatic or heteroaromatic ring system which contains an electron-deficient heteroaryl group, where the aromatic or heteroaromatic ring system is coupled to the nitrogen atom of the indeno-carbazole.

\* \* \* \* \*